United States Patent
Monzyk et al.

(10) Patent No.: US 7,498,275 B2
(45) Date of Patent: *Mar. 3, 2009

(54) ARTIFICIAL PULMONARY CAPILLARY

(75) Inventors: Bruce F. Monzyk, Delaware, OH (US); Eric C. Burckle, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 450 days.

This patent is subject to a terminal disclaimer.

(21) Appl. No.: 10/485,476

(22) PCT Filed: Aug. 1, 2002

(86) PCT No.: PCT/US02/24587

§ 371 (c)(1),
(2), (4) Date: Jul. 26, 2004

(87) PCT Pub. No.: WO03/011359

PCT Pub. Date: Feb. 13, 2003

(65) Prior Publication Data

US 2004/0243051 A1    Dec. 2, 2004

Related U.S. Application Data

(60) Provisional application No. 60/358,448, filed on Feb. 20, 2002, provisional application No. 60/388,977, filed on Jun. 14, 2002.

(51) Int. Cl.
*A61M 37/00* (2006.01)
*A61M 1/00* (2006.01)
*C10B 25/00* (2006.01)

(52) U.S. Cl. .................. 442/45; 604/4.01; 604/6.08; 604/6.14; 422/44; 422/46; 422/47; 422/48; 202/244; 202/254

(58) Field of Classification Search ............. 422/44–48; 204/252, 244, 254; 604/4.01–6.16, 7–10, 604/23–25; 210/748–766
See application file for complete search history.

(56) References Cited

U.S. PATENT DOCUMENTS

| | | | | |
|---|---|---|---|---|
| 3,533,408 A | * | 10/1970 | Paoli | 604/66 |
| 3,910,780 A | * | 10/1975 | Henley et al. | 96/12 |
| 3,958,941 A | * | 5/1976 | Regan | 422/80 |
| 3,960,657 A | * | 6/1976 | Bowley | 435/2 |
| 4,011,149 A | * | 3/1977 | Nozik | 205/340 |
| 4,140,591 A | | 2/1979 | Fong et al. | |
| 4,205,042 A | * | 5/1980 | Lobdell et al. | 422/47 |
| 4,521,499 A | | 6/1985 | Switzer | |
| 4,595,568 A | | 6/1986 | Van Damme et al. | |
| 4,643,817 A | * | 2/1987 | Appleby | 204/242 |

(Continued)

*Primary Examiner*—Leslie Deak
*Assistant Examiner*—Phil Wiest
(74) *Attorney, Agent, or Firm*—Richard M. Klein; Fay Sharpe LLP

(57) ABSTRACT

The present invention is directed to a photolytic cell, and to a photolytic artificial lung incorporating such a cell. The photolytic artificial lung converts water to oxygen for blood absorption, regulates pH, the removes carbon dioxide, and co-produces electrical power. The photolytic artificial lung includes a photolytic cell where all of the chemical reactions occur. Additionally, the present invention relates to photolytically sensitive materials for oxygen generation. These materials are useful for gas-free artificial lung and/or pulmonary capillary fabrication. The photolytic cell disclosed herein can also be used to direct chemical reactions in organs other than the lung.

20 Claims, 19 Drawing Sheets

U.S. PATENT DOCUMENTS

| | | |
|---|---|---|
| 4,790,916 A | 12/1988 | Murphy et al. |
| 4,791,910 A * | 12/1988 | Ishida et al. ................. 126/570 |
| 4,952,511 A | 8/1990 | Radmer |
| 4,968,483 A * | 11/1990 | Muller et al. .................. 422/45 |
| 4,970,166 A | 11/1990 | Mori |
| 5,052,382 A | 10/1991 | Wainwright |
| 5,086,620 A | 2/1992 | Spears |
| 5,151,252 A * | 9/1992 | Mass ....................... 422/186.3 |
| 5,174,877 A * | 12/1992 | Cooper et al. ............... 204/193 |
| 5,460,705 A * | 10/1995 | Murphy et al. .............. 204/252 |
| 5,501,801 A * | 3/1996 | Zhang et al. ................. 210/748 |
| 5,614,378 A * | 3/1997 | Yang et al. ..................... 435/41 |
| 5,718,878 A * | 2/1998 | Zhang ........................ 423/610 |
| 5,779,912 A * | 7/1998 | Gonzalez-Martin et al. . 210/748 |
| 6,136,186 A * | 10/2000 | Gonzalez-Martin et al. ....................... 210/198.1 |
| 6,183,695 B1 * | 2/2001 | Godec et al. ................... 422/79 |
| 6,248,087 B1 * | 6/2001 | Spears et al. ............... 604/6.14 |
| 6,293,159 B1 * | 9/2001 | Kriesel et al. ............ 73/861.47 |
| 6,335,112 B1 * | 1/2002 | Asukabe et al. ................ 429/30 |
| 6,551,490 B2 * | 4/2003 | Andrews et al. ............ 205/626 |
| 6,866,755 B2 * | 3/2005 | Monzyk et al. .............. 204/252 |
| 2001/0022952 A1 * | 9/2001 | Rau et al. ..................... 422/169 |
| 2005/0025680 A1 * | 2/2005 | Monzyk et al. .............. 422/186 |

* cited by examiner

KEY ARRANGEMENT PATTERNS OF MATERIALS OF CONSTRUCTION FOR PAL/PDEC ARCHITECTURE

| M | MO | M | MO | M | MO | M |
|---|----|---|----|---|----|---|
| MO | hv | MO | B | MO | hv | MO |
| M | MO | M | MO | M | MO | M |
| MO | B | MO | hv | MO | B | MO |
| M | MO | M | MO | M | MO | M |
| MO | hv | MO | B | MO | hv | MO |
| M | MO | M | MO | M | MO | M |
| MO | B | MO | hv | MO | B | MO |
| M | MO | M | MO | M | MO | M |
| MO | hv | MO | B | MO | hv | MO |
| M | MO | M | MO | M | MO | M |
| MO | B | MO | hv | MO | B | MO |
| M | MO | M | MO | M | MO | M | hv = Uv/Vislight
MO = metal oxide photo-sensitive material
B = whole blood
M = electrical conduction, normally a metal

FIGURE 16

ARTIFICIAL PULMONARY CAPILLARY

The present application claims priority to U.S. patent application Ser. No. 09/920,385, filed on Aug. 1, 2001; U.S. Provisional Application Ser. No. 60/358,448, filed on Feb. 20, 2002; and U.S. Provisional Application Ser. No. 60/388,977, filed on Jun. 14, 2002.

FIELD OF THE INVENTION

The present invention is principally directed to a photolytic cell (or module) that utilizes light energy to achieve physiological gas exchange in fluids. The photolytic cell can be used to provide oxygen generation, such as in the blood stream of a patient. The present invention is also directed to a photolytic artificial lung ("PAL") and/or an artificial pulmonary capillary incorporating such a cell. In a further embodiment, the invention relates to the use of mesoporous materials in the photolytic cell to enhance gas exchange. The invention finds particular applications in conjunction in the field of artificial organs and the medical arts.

BACKGROUND OF THE INVENTION

The lung is the main organ in the respiratory system. In the lung, venous blood is relieved of carbon dioxide and oxygenated by air drawn through the trachea and bronchi into the alveoli.

In this regard, air travels from the mouth and nasal passage to the pharynx and the trachea. Two main bronchi, one on each side, extend from the trachea. The main bronchi divide into smaller bronchi, one for each of five lobes. These further divide into a great number of smaller bronchioles. Additionally, there are about 50 to 80 terminal bronchioles in each lobe. Each of these divides into two respiratory bronchioles, which in turn divide to form 2 to 11 alveolar ducts. The alveolar sacs and alveoli arise from these ducts. The spaces between the alveolar sacs and alveoli are called atria.

The alveolus is the point at which the blood and inspired air are separated only by a very thin wall or membrane that allows oxygen and nitrogen to diffuse into the blood and carbon dioxide and other gases to pass from the blood into the alveoli. The alveoli contain small pores that serve to connect adjacent alveoli to each other.

The primary purpose of the lung is to bring air and blood into intimate contact so that oxygen can be added to the blood and carbon dioxide can be removed. This is achieved by two pumping systems, one moving a gas and the other a liquid. The blood and air are brought together so closely that approximately one micrometer ($10^{-6}$ meter) of tissue separates them. The volume of the pulmonary capillary circulation is about 150 ml, but this is spread out over a surface area of approximately 750 sq feet. This capillary surface area surrounds 300 million air sacs called alveoli. There blood that is low in oxygen but high in carbon dioxide is in contact with the air that is high in oxygen and low in carbon dioxide for less than one second. This allows for the blood to be replenished with oxygen and for the excess carbon dioxide to be removed.

Hemoglobin, the iron-containing pigment of red blood cells, then carries the oxygen from the lungs to the tissues. In the lungs, hemoglobin combines readily with oxygen, by a process called oxygenation, to form a loose, unstable compound called oxyhemoglobin. In the tissues, where oxygen tension is low and carbon dioxide tension is high, oxyhemoglobin liberates its oxygen in exchange for carbon dioxide. The carbon dioxide then becomes carried by the blood serum to the lungs, where the whole oxygenation process begins again.

There have been numerous efforts in the past 40 years to achieve artificial lung function. Unfortunately, no new innovative respiratory assist therapy has been developed for patients with severe, life-threatening lung disease. This is largely due to inadequate knowledge of pulmonary pathophysiology, a lack of emerging therapies, and insufficient mechanisms for providing intermediate to long-term respiratory support. The lack of adequate technology for respiratory support for the patient with deteriorating lung function, in particular, has had profound effects on the quality of life for this increasingly large segment of the population.

The number of deaths annually from all lung disease is estimated to be approximately 250,000 (150,000 related to acute, potentially reversible respiratory failure and 100,000 related to chronic irreversible respiratory failure) with an estimated economic burden of disease in the range of 72 billion dollars per year. Furthermore, the emotional toll of progressive respiratory failure is profound, particularly as it affects children and adolescents with progressive pulmonary disease. The impact of this public health problem can be conceived in terms of the direct costs for intensive, sub-acute, and long-term health care services, and the indirect costs associated with lost wages and productivity for the patient and the patient's family, and the increased need for support services.

While the death rates for cardiovascular disease, cancer, and all other major diseases have recently decreased significantly, the rate of death related to chronic pulmonary lung disease (CPLD) has increased by 54%. Lung disease also represents one of the leading causes of infant mortality, accounting for 48% of all deaths under the age of one. For these patients, respiratory assistance during pulmonary failure has been achieved by employing ventilator therapy, despite the enormous cost and morbidity associated with this modality.

Furthermore, it is well accepted that closed, positive-pressure, mechanical ventilation, applied at moderate levels of intensity, for short periods of time, is a somewhat safe and efficient means for improving gas exchange in patients with acute respiratory failure. However, with prolonged duration of intensive respiratory support, serious adverse effects may occur. These effects, including oxygen toxicity, baromtrauma, altered hormone and enzyme systems, and impaired nutrition, may result in further injury to the failing lungs, or add significantly to the morbidity and mortality for these patients. As a result, alternative methods have been sought for augmenting blood gas exchange, where mechanical ventilation is inadequate or cannot be safely applied.

In view of the above and other reasons, there has been great interest in developing an artificial means for accomplishing physiological gas exchange directly to the circulating blood and bypassing the diseased lungs. While previous efforts have provided some measure of success, they have been limited in their usefulness or hindered by excessive cost.

One approach to artificial lung function has been by gas sparging or diffusion of gas across the membrane surface of hollow fibers placed within the blood supply. Previous efforts have achieved some success, and have taught much to pulmonary physiologists, but gas sparging or diffusion has yet achieved the degree of gas exchanges optimally desired.

Furthermore, other methods and artificial lung systems have been developed from introducing gaseous oxygen by air sparging. However, gas sparging is very detrimental to biological tissues such as red blood cells. Also, gas sparging attempts to control the differential pressure across thin gas/liquid membranes such as those found in porous-walled hollow fibers.

Another approach to artificial lung function, extracorporeal membrane oxygenation (ECMO), constitutes a mechanism for prolonged pulmonary bypass, which has been developed and optimized over several decades but has limited clinical utility today as a state-of-the-art artificial lung. The ECMO system includes an extra-corporeal pump and membrane system that performs a gas transfer across membranes. Despite the numerous advances in the implementation of ECMO over the years, its core technology is unchanged and continues to face important limitations. The limitations of ECMO include the requirement for a large and complex blood pump and oxygenator system; the necessity for a surgical procedure for cannulation; the need for systemic anticoagulation; a high rate of complications, including bleeding and infection; protein adsorption and platelet adhesion on the surface of oxygenator membranes; labor intensive implementation; and exceedingly high cost. As a result of these limitations, ECMO has become limited in its utility to select cases of neonatal respiratory failure, where reversibility is considered to be highly likely.

The development of the intravenous membrane oxygenation (IVOX) also represented a natural extension in the artificial lung art, since it was capable of performing intracorporeal gas exchange across an array of hollow fiber membranes situated within the inferior vena cava but did not require any form of blood pump. The insertion of the IVOX effectively introduced a large amount of gas transfer surface area (up to 6000 $cm^2$) without alteration of systemic hemodynamics. Unfortunately, as with ECMO, the IVOX system has numerous limitations, including only a moderate rate of achievable gas exchange; difficulty in device deployment; a relatively high rate of adverse events; and a significant rate of device malfunctions, including blood-to-gas leaks due to broken hollow fibers.

A further approach to treat lung disease, is through the use of lung transplants. The improvement of methods to transplant viable lungs into patients is fundamentally the most significant recent advance in the therapy of chronic lung diseases. The most common indications for lung transplantation are emphysema, pulmonary fibrosis, cystic fibrosis, and pulmonary hypertension. Selection conditions emphasize the presence of irreversible disease localized to the respiratory system, and social and psychological conditions supportive of the ability to go through extended pulmonary rehabilitations. In contrast, the absence of these conditions present relative contraindications to this approach. The donor organ should originate in a relatively healthy, infection free individual, under the age of 65. Following these guidelines, success has been achieved in increasing numbers for patients throughout the United States.

Profound limitations in the number of donor organs has made this option unrealistic for the great majority of patients who would benefit the most. While rationing is the standard for all transplantable organs, the need for rationing is particularly acute in the case of the lungs, owing to the following issues: (1) the large discrepancy between donor and recipient numbers (3350 registration for lung transplant in 1999 and only 862 performed); (2) the relatively low yield of usable lungs, with only 5-10% of mulborgan donors yielding lungs acceptable for transplantation; and (3) the absence of effective temporary methods to support blood gas exchange during the waiting period prior to transplantation. The complexity of this problem is increased even further, when considering the inevitable compromise between supplying organs to patients who are the most ill, and who have the most to gain, but for whom outcomes are generally poor, versus relatively healthier patients with no complications, who have less need but for whom outcomes are predictably better. For example, a patient with emphysema is highly likely to achieve a positive outcome from transplantation, but generally will not exhibit improved survival. In contrast, a patient with cystic fibrosis has considerably higher risk of surgery due to the presence of multiorgan involvement of the disease, but for these young patients, successful transplantation optimizes survival.

Therefore, a serious need exists for new technology and therapeutic approaches that have the potential to provide intermediate to long-term respiratory support for patients suffering from severe pulmonary failure. Also, the need for an efficient and inexpensive technology to achieve sustained gas exchange in the blood, thereby bypassing the diseased lungs without resorting to chronic ventilation, remains paramount.

SUMMARY OF THE INVENTION

In one aspect, the present invention is directed to a photolytic cell and, more specifically, to a photolytic artificial lung and/or an artificial pulmonary capillary incorporating such a cell. The photolytic artificial lung and/or the artificial pulmonary capillary are capable of facilitating gas exchange in the blood of a patient while bypassing the alveolar-capillary interface. They may be utilized for lung replacement and/or for oxygenation supplementation of the blood stream. Moreover, they are also particularly useful for treating a number of lung afflictions.

In this regard, the artificial pulmonary capillary and the photolytic artificial lung of the present invention are of similar constitutions. However, the artificial pulmonary capillary is of smaller (i.e. sometimes nearly microscopic) construction. This is discussed in more detail below.

The photolytic artificial lung is a device, internal or external to the body, that utilizes light, such as a laser or lamp, to achieve physiological and therapeutic gas exchange in the blood stream. In such an exchange, oxygen is dissolved into the blood stream while carbon dioxide is removed and pH is controlled. This is due to the use of photochemistry. The photolytic artificial lung oxygenates blood without the deleterious effect on red blood cells associated with direct gas sparing (i.e. blood cell lysis, pH balance difficulties, etc.), while simultaneously controlling blood pH and carbon dioxide content.

More particularly, the photolytic artificial lung includes a photo-electro chemical cell ("photolytic cell" or "photolytic module") that, in part, operates similar to the photosynthesis process that takes place in green plants. The photolytic artificial lung utilizes the photolytic cell to convert light energy in order to simultaneously generate oxygen from water, useful acidity and electrical energy. The photolytic cell also removes carbon dioxide from the blood stream. One or more photolytic cells can be included in the photolytic artificial lung of the present invention depending on the quantity, quality, etc. of desired gas exchange.

The light energy utilized in the present invention is ultraviolet ("UV") light or visible light, with the laser form being the most preferred. However, the light energy can also be broad-band, received by the way of a "light pipe" fiber optic cable or by the way of an attenuated total reflectance (ATR) link.

In the artificial lung, dissolved oxygen is generated from water present in the blood stream by means of the light dependent chemical reactions, photolysis and disproportionation. This is followed by the removal or clearing of carbon dioxide by the reactions of bicarbonate ion protonation and dehydration.

Photolysis is the initiation of a chemical reaction as a result of absorbing one or more quanta of radiation. Here, water is converted into oxygen by a light-activated catalyst, such as a semiconducting metal oxide. The metal oxide is utilized as a photo-absorbent material or a photo-absorption element. It is photolytically irradiated to form, from water present in the fluid or blood stream, hydrogen ions, hydrogen peroxide or other forms of oxygen gas precursor (active oxygen, "AO") and electrons by the absorption of one or more quantra of electromagnetic radiation. The free electrons generated are then electrically conducted away to avoid reversal of the reaction and optionally utilized to drive electrical devices, such as a pump.

For example, it has been found that active oxygen is readily generated in the present invention by the use of the anatase form of titania ($TiO_{2(a)}$) as the light absorbent material. The photo energy of light, such as ultraviolet laser light (about 350 nm), selectively excites $TiO_2$ semiconductor transition (about 350-390 nm band, or about 3.1 eV) with minimal material radiation or transmission. The ultraviolet energy produces charge separation in the anatase form of $TiO_2$, which then produces active oxygen (AO) and free electrons. The free electrons are then subsequently electrically conducted away due to the semi-conducting property of the anatase. Alternatively, other suitable light absorbent materials can also be utilized in the present invention at various wavelengths provided that the energy is sufficient to produce active oxygen.

Disproportionation is a chemical reaction in which a single compound serves as both oxidizing and reducing agent and is thereby converted into a more oxidized and a more reduced derivative. For example, hydrogen peroxide (active oxygen) produced during photolysis can be converted by means of manganese dioxide ($MnO_2$), or other disproportionation catalytic agents and/or processes, into dissolved oxygen (DO) and water. This reaction produces dissolved oxygen (DO) from water and bypasses the harmful gaseous state.

Additionally, in the artificial lung of the present invention, carbon dioxide is removed from the blood stream by the means of the reactions of protonation and dehydration. In essence, the hydrogen ions formed during photolysis react with the bicarbonate ($HCO_3^-$) and carbonate ($CO_3^=$) ions present in the blood stream causing conversion of these ions into carbonic acid. In the presence of carbonic anhydrase, a blood component, the carbonic acid then quickly dissociates into water and carbon dioxide. The carbon dioxide gas is then subsequently vented into the environment.

Alternatively, due to concerns with infection in human lung assistance applications, a novel method and device is also disclosed herein for removing carbon dioxide from the system by molecular absorption. In this embodiment, carbon dioxide is removed from the blood stream by means of a carbon dioxide absorber device (i.e., a sorber), or other similar gaseous removal devices, under sterile conditions.

Consequently, the artificial lung of the present invention produces dissolved oxygen directly from water present in the blood stream, omitting the gaseous state which has previously caused pressure, shear, weight, and bulkiness problems with other blood oxygenation technologies. At the same time, the artificial lung also utilizes the hydrogen ions produced from the water to release the carbon dioxide. Additionally, the reactions occurring in the artificial lung do not involve the generation or use of high temperatures or pressures associated with previous devices and/or processes. The photolytic artificial lung is preferably designed to be self-contained and self-regulated. It requires no external gas supply.

A brief description of the pertinent reactions involved in the embodiment of the present invention utilizing anatase as the light absorbent material (i.e. a photolytic catalyst and $MnO_2$ as the disproportionation catalyst) is provided below:

Photolysis:

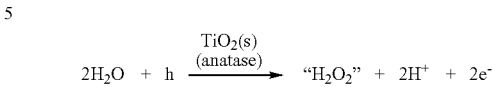

Disproportionation:

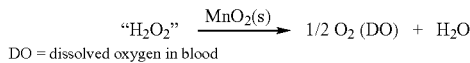

DO = dissolved oxygen in blood

Protonation ($H^+$ ions from photolysis reaction):

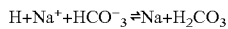

$CO_2$ Gas Generation:

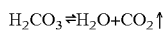

Catalyzed Dehydration (optional):

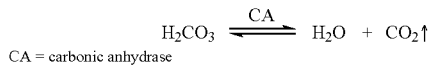

CA = carbonic anhydrase

The above information shows the general chemical reactions involved in the photolytic cell to produce dissolved oxygen. Subsequent to this production, the electrons are conducted away, and the dissolved oxygen diffuses from the film surface to oxygenate hemoglobin present in the blood.

As a result, the primary function of the photolytic artificial lung of the present invention is to provide respiration assistance in patients with lung disease, both in acute as well as chronic conditions. However, other medical applications are also feasible which also require the photochemical reactions of the present invention and/or the convenience of photolytic power. These include, among others, in-body drug level maintenance and release, and the contribution to the function of other organs such as the kidneys and the liver.

In a more particular embodiment, the photolytic artificial lung of the present invention comprises an inlet for receiving blood from the blood stream of a patient. A pump extracts blood from the patient and moves the blood into at least one flow-through photolytic cell via the inlet. The photolytic cell contains a photolytic coating comprising a light-activated photolytic catalyst and a disproportionation catalyst that converts water from the blood into dissolved oxygen, while at the same time removing carbon dioxide as described above. A light supply provides light energy to the photolytic cell. An outlet moves blood out of the photolytic artificial lung and back into a patent.

The photolytic cell is compatible with blood and provides high yields of dissolved oxygen to the blood stream. The resulting photolytic artificial lung is capable of use externally or internally by a patient, as well as in a stationary or portable form. Furthermore, the artificial lung is scalable to allow the photo-activated gas exchanges to be accomplished in a small and wearable extra-corporeal device, or in an intra-corporeal device inserted into a patient's venous blood supply. Examples of such microfabricated devices, such as artificial pulmonary capillaries, are discussed in more detail below.

In a further aspect, the present invention is also directed to a photolytic cell. The photolytic cell includes a transparent substrate or window. An anode (such as a metal film) is adjacent to the transparent window. A photolytic coating containing a light-activated catalyst and a disproportionation catalyst abuts the anode. A cell flow through area is adjacent to the light activated catalyst. A cation exchange membrane borders the cell flow through area. A catholyte abuts the cation exchange membrane. A cathode is present adjacent to the catholyte and is connected to the anode.

In another aspect, the present invention is further directed to a gas absorption or sorption device for collecting and converting a gas, such as carbon dioxide, to a solution or solid. The gas sorption device comprises a coalescence compartment including a gas head space and a coelesor connected thereto, wherein gas accumulates and/or is concentrated in the gas head space. A gas sorber connected to the coalescence compartment allows for the movement of gas from the gas head space to the gas sorber and the gas sorber converts gas to a solution or a solid. The sorber can be disposed or regenerated thereby avoiding the continuous venting of carbon dioxide to the atmosphere.

In an additional aspect, the present invention is further directed to a method for delivering oxygen to an aqueous bicarbonate ion solution. The method comprises moving the solution into a photolytic cell wherein light is utilized by a light-activated catalyst to produce oxygen from water, with a small concomitant pH change to cause a release of carbon dioxide, and moving the oxygenated solution out of the photolytic cell.

In still another aspect, the present invention is yet further directed to a method for oxygenating blood from a patient. The method includes moving deoxygenated blood into a photolytic cell; converting water to dissolved oxygen in the photolytic cell; binding dissolved oxygen to blood hemoglobin; forming carbon dioxide in the photolytic cell; removing carbon dioxide formed in the photolytic cell; and moving oxygenated blood out of the photolytic cell. This process emulates, to a certain degree, selected portions of the natural process by which plants produce oxygen, namely photosynthesis, and the way the lung eliminates carbon dioxide, namely through a pH drop. This method produces dissolved oxygen directly from water, omitting the gaseous state. It can be utilized to achieve therapeutic gas exchange in patients with respiratory failure.

In a further aspect, the present invention relates to the direct photolytic conversion of water to liquid phase oxygen (dissolved oxygen), with commensurate clearance of carbon dioxide. A test flow cell is provided comprising a conductive coating of vacuum-deposited titanium (Ti) metal, adherent $TiO_2$ (anatase), and $MnO_2$, applied as a laminant to a glass substrate. The device was then immersed in Lockes-Ringer solution (synthetic blood serum) and/or blood. Long wavelength (low energy) UV laser light, directed to the transparent glass slide, reproducibly resulted in the generation of $H_2O_2$, an active form of oxygen (active oxygen), which was subsequently converted, by the catalytic action of $MnO_2$, to dissolved oxygen. The absence of light activation provided an entirely null reaction. Based on these results and other, the photolytic cell or module may be used, employing multiple parallel photolytic surfaces to improve system yield and $CO_2$ clearance through selective membrane diffusion of gas phase molecules from the dissolved oxygen enriched fluid following photolytic induction.

In a still further aspect, the present invention relates to the use of mesoporous materials in the photolytic artificial lung. The mesoporous materials are used to provide high-surface area photolytically active coatings to photolytically drive chemical changes, photochemical changes, electricity generation, and/or electrochemical changes in fluid streams adjacent to the coating/material, or in the case of electricity, electrical current driven into wires attached to the coatings directly, or via an electrical conducting intermediate material.

Preferably, the mesoporous materials are self-assembled monolayers on mesoporous supports ("SAMMS"). A particularly useful material from this technology is known as "mesoporous silica." Moreover, molecular sieves, such as zeolites with 3-D pore structure (pore size, about 7-100 Å) including zeolite X, Y and B, and silica and/or silica/titania MCM's (pore size, about 20-80 Å) are also beneficial. Similarly, titania (especially anatase versions) is useful in accordance with the present subject matter. Other useful coatings chemistries are based on zinc oxide, tungstates, etc.

The photolyzed mesoporous coatings consist of a photoactive material which results in the conversion of water into oxygen, especially dissolved oxygen. Additionally, the bicarbonate ion is converted therein by the hydrogen ions into carbon dioxide gas for venting and/or removal.

This embodiment utilizing mesoporous materials represents the next critical technology portion of the photolytic lung (PAL, and more generally, photolytically driven electrochemically conversion, PDEC) technologies—that of organized microscopic architecture of photolytic constructs (OMAPC). The design of the fluid/photo-sensitive coatings/films architecture is critical to controlling the commercial value of the technology by providing small device size (practical ambulatory use, and for implantation into the body), and photolytic conversion efficiency (low cost and low power requirements).

The SAMMS technology, and any other mesoporous material of highly ordered structural support, represents candidates for commercially viable PDEC technologies for at least three reasons;

1. near UV and visible light transparency (silica and metal oxides)
2. high surface area with fluids flowing through them
3. organized structure so that optical light guides can be designed into them.

Consequently, a further embodiment of the invention is directed to the use of mesoporous materials, and the like, to construct (in the case of PAL) artificial pulmonary capillaries. Note that the gross shape of the final device can have any suitable shape to fit the need (e.g. the body lung cavity, a vein, a module to fit into an extra corporeal device, etc.). It's the microstructure and how it relates to controlling the light path to a region adjacent to the fluid (blood) that is the key architecture needed from the mesoporous (and the like) material.

These and other objects and features of the invention will be apparent from the detailed description set forth below.

BRIEF DESCRIPTION OF THE DRAWINGS

The present invention will become more fully understood from the detailed description given below and the accompanying drawings. The description and drawings are given by way of illustration only, and thus do not limit the present invention.

FIG. 2A shows a general illustration of the photolytic artificial lung connected externally to a patient. FIG. 2B shows an interior view of the components of one embodiment of the photolytic artificial lung. FIG. 2C also shows an inside view of an alternative embodiment of the photolytic artificial lung, and FIG. 2D illustrates the chemical reactions occurring therein.

FIG. 16 illustrates the pattern of materials for the construction of a device containing microfabricated, artificial pulmonary capillaries.

DETAILED DESCRIPTION OF THE PREFERRED EMBODIMENTS

Figure 1:
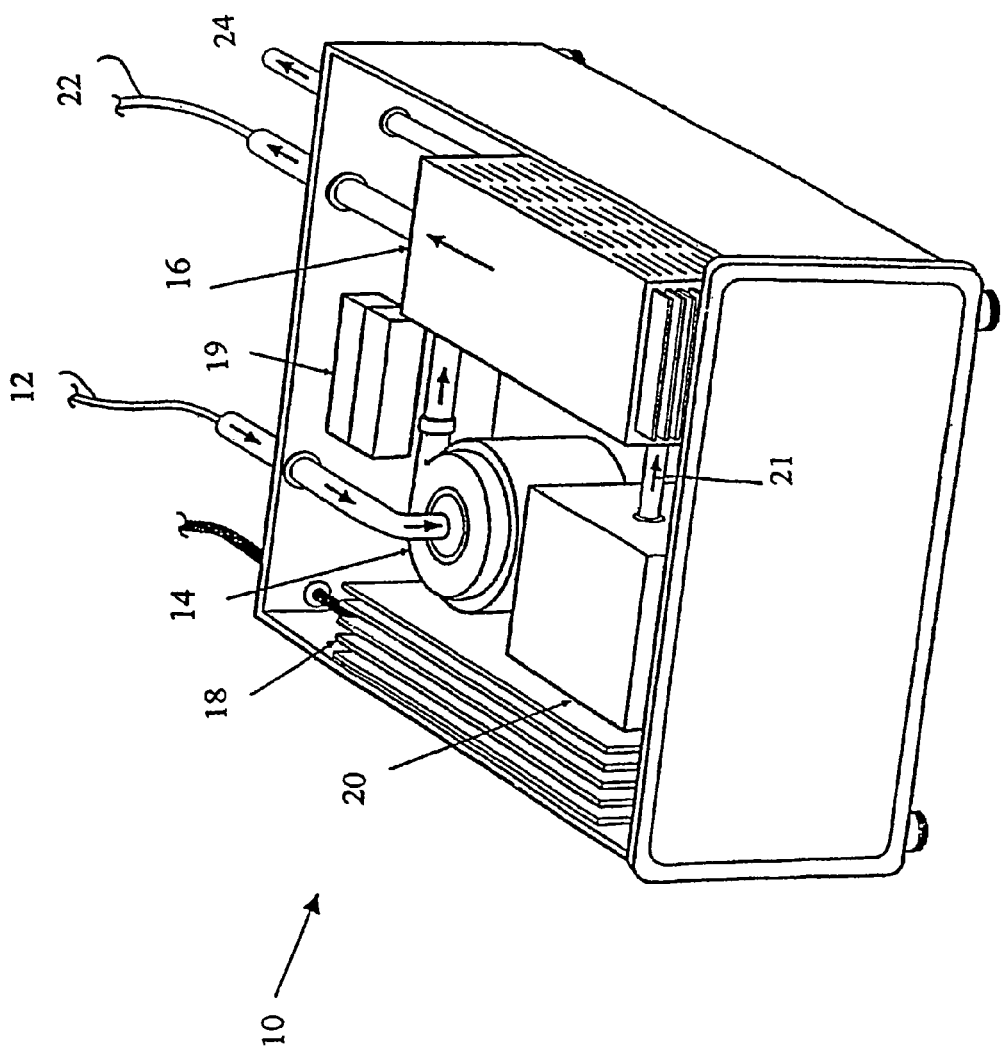
FIG. 1 shows a perspective view of an embodiment of a photolytic artificial lung designed for external or extra-corporeal usage.

The present invention is directed to a photolytic artificial lung having among other components, a photolytic cell. The photolytic cell is the fundamental functional unit of the invention. It acts as a general purpose oxygen generator, carbon dioxide remover and a pH controller. The photolytic cell includes a photochemically active material for use in producing various chemical reactions that enable the exchange of oxygen and carbon dioxide in the blood stream. By optimizing a relative balance between light activation, photolytic cell surface area and blood flow, it is designed to maximize efficient gas transfer. The photolytic cell, when used as a photolytic artificial lung application for lung replacement/supplementation, will oxygenate blood without the deleterious effect on red blood cells associated with direct gas sparing while simultaneously controlling blood pH and carbon dioxide contact.

Moreover, many devices other than an artificial lung can be derived and implemented based upon the photolytic cell. For example, the photolytic cell can be utilized to perform numerous operations including chemical processes, fermentation systems, regulation of drug levels, and replacement or assistance of one or more organ functions. Consequently, as a result of the somewhat similar photo-electrochemical transformations involved, the photolytic cell component of the invention can have additional applications outside of the artificial organ field.

In the preferred embodiment, the present invention is directed to the use of the photolytic cell in a novel respiratory assist device and process i.e., a photolytical artificial lung. The photolytic artificial lung includes one or more photolytic cells having photochemically active material and associated components for the production of oxygen, the regulation of pH, the removal of carbon dioxide, and the co-production of electrical power. The electrical power can be used to produce additional chemical changes or reactions. Optionally, the invention may include a photolytic chamber to house or hold a sufficient number of stacked or assembled photolytic cells to perform the rate of gas exchange desired.

The technology of the present invention is based in part, on the photo-initiated electrochemical transformation that mimics, to some degree, the natural process of photosynthesis. In photosynthesis, energy derived from sunlight is used to drive key metabolic reactions that fuel the growth of plants along with the production of oxygen.

The present photolytic artificial lung combines aspects of photosynthesis and the operations of the lung. In the lung, oxygen is transferred from the air to the blood as dissolved oxygen that is available for binding to hemoglobin (Hb) for transport to body tissues, and carbon dioxide is released from the blood into the air. The equilibrium shifts from the binding of dissolved oxygen to Hb and release of carbon dioxide are driven by gas pressure differences and carbonic anhydrous catalysis.

In the present invention, the photolytic artificial lung uses light energy to produce dissolved oxygen from water. A concomitant small pH change causes a release of carbon dioxide from whole blood or serum. In the preferred embodiment, chemical materials formed in the chemical processes from the photolytic artificial lung are insoluble solids thereby preventing blood contamination.

As mentioned above, the present invention applies physical principles derived from nature to create a device driven by photolytic chemistry. The preferred examples thus far, have focused on the creation of prototype "alveolar" surfaces, whose chemical activity is determined by the interaction of light with a highly absorbant surface, such as a $TiO_2$ surface. The principal function of this device is the generation of oxygen from water via a sequence of light-regulated chemical reactions (photolysis for charge separation and disproportionation to produce oxygen), followed by chemical exhalation of the by-product carbon dioxide (protonation and dehydration). Efficient and biocompatible photo-transducing materials are possible, and their output can be linked with flowing blood, thus creating a photolytic unit, functionally similar to the human alveolus. The examples generated to date were designed to optimize the material attributes of the photolytic surface in order to maximize quantum yield and the production of dissolved oxygen relative to flow, thus maximizing gas exchange per unit area of blood contact.

Accordingly, the present invention emulates the natural process by which plants produce dissolved oxygen (DO) directly from water, thus omitting the gaseous state. Adhering to this basic principle of nature, a method has been developed, which significantly increases the amount of dissolved oxygen (DO) in liquids through light activation of a cascade of chemical reactions. This technology can be used to first create an extracorporeal device, then a highly miniaturized, intracorporeal device, capable of achieving physiological gas exchange in patients. The approach involves the combination of several well-characterized photochemical reactions in an original manner. It is recognized that any lung supplementation technology must accomplish physiological gas exchange, without altering pH balance or induce blood cell lysis. Here, oxygen is photolytically generated from water at a catalyst center, using photolytic energy under mild conditions of pressure, temperature and pH, while releasing hydrogen ions. Hydrogen ions, which are released into solutions of bicarbonate ion, present in the serum, cause conversion of these ions into carbonic acid, which spontaneously dissociates into water and $CO_2$ in the presence of carbonic anhydrase, a natural component of blood.

The initial model, used a semi-conducting metal oxide as the photo-absorption element, the anatase form of titania, or $TiO_2$. Photolysis of this oxide results in the generation of active oxygen, in a manner, which is considerably more long lasting than photosynthetic pigments (i.e. the chlorophiles). Importantly, the light energy associated with activation by a 354 nm UV laser light selectively excites the $TiO_2$ semiconductor electronic transition (350-389 nm band, or about 3.2 eV) with minimal wasted radiation or transmission. Special dopants may adjust this wavelength, in order to reduce the energy requirement and even to allow activation within the range of visible light. UV energy produces charge separation in the anatase, which then produces active oxygen and free electrons, the latter being electrically conducted away. Diffusion layers are minimized through the use of electron conductance to and from the photolytic site (as is done in natural photosynthesis) by photolytic transparency and by electrochemical conduction. The active oxygen is then converted to dissolve oxygen through the use of a disproportionation catalyst such as $MnO_2$. Importantly, applicants have demonstrated the ability of this device to efficiently generate both fluid phase oxygen (i.e. dissolved oxygen) and gas phase oxygen (i.e. $PO_2$).

Taken from a broad perspective, the present invention includes the following system components: 1) a sensitive and complex aqueous phase, 2) photolytic energy to provide "charge separation" in a thin film, 3) electrical energy, produced from the electrons of the "charge separation" photolytic reaction, 4) chemical reactions driven by the photochemistry, from the therapeutic component of the device, i.e. DO generation, and 5) degassing at low pressure, as in the case of the removal of $CO_2$ from the blood. Testing has demonstrated that these components can perform on a microscopic scale to achieve "alveolar-type" gas exchange. These results provide a compelling rationale to move to the next step, the selection of coating/thin film inorganic materials to provide acceptable quantum yields and DO generation efficiency. Although apparently complex, component arrays such as these, are becoming increasingly common, with the appearance of "lab on a chip", "combinatorial chemistry", and "micro-technology chemical manufacturing" type devices. Such devices are derived from the evolving science of micro-fabrication (μFAB), and employ simple, yet robust, approaches used in the manufacture of integrated circuits for the semiconductor industry. Such μFAB techniques can be used to produce the composite, high surface area, photolytically-driven thin film coatings ("constructs") for the technology, as applied to the artificial lung device.

The invention can also use mesoporous, amorphous, microporous, crystalline, heterogeneous, or homogenous materials and coatings, and the like, alone or in combination to provide high-surface area active coatings to photolytically drive chemical changes, photochemical changes, electricity generation, and/or electrochemical changes in fluid streams, preferably adjacent to the coating/material, or, in the case of electricity, electrical current driven into wires attached to the coating directly, or via a electrical conducting intermediate material. The said fluid can be liquid or gas or sol gel or conducting solid or porous solid. The preferred fluid is aqueous solution, the most preferred medium is human blood or blood serum.

The preferred mesoporous material is SAMMS (self-assembled monolayers on mesoporous supports). A particularly useful coating/film/material from this technology appears to be that type known as "mesoporous silica". Titania (especially anatase versions) has been found useful for the invention. Other useful coating chemistries are based on zinc oxide and tungstates. The preferred application is for an artificial lung where the photolyzed mesoporous coating consists of a photoactive material which results in the conversion of water into oxygen, $O_2$, especially dissolved oxygen (DO), and the bicarbonate ion is converted by the hydrogen ions so generated into $CO_2$ gas for venting.

Photolytic chemistry forms a natural and efficient mechanism for converting omnipresent light energy into useful chemical reactions. The invention applies these fundamental chemical concepts to solve a pressing clinical problem, the creation of a photolytically-driven artificial lung and/or artificially created pulmonary capillaries. The achievement of this technology will, on one hand, have great utility as a respiratory support device for patients severely impaired by chronic pulmonary disease, and, on the other hand, can comprise the basis for a novel technological platform from which numerous applications may emerge.

Preferably, the photolytic artificial lung of the instant invention comprises a blood inlet cannula, a pump, at least one photolytic cell, a light source that irradiates the photolytic cells, an oxygenated blood outlet cannula and a carbon dioxide vent and/or absorption device. A power source and/or batteries can be present to power the pump or light source. One or more in-line sensors and processors can be present to monitor and optimize the flow through the system, the amount of oxygen and/or carbon dioxide generation, the presence of toxins, etc. Desaturated blood circulating through the device will be pumped through the photolytic cells where light activation will result in dissolved oxygen generation and ultimate carbon dioxide removal.

More particularly, FIG. 1 shows an embodiment of a photolytic artificial lung 10 developed as an extra-corporeal respiratory assist system. The artificial lung 10 includes a blood inlet 12 that cannulates blood from the patent into the artificial lung 10. The blood inlet 12 is connected to a pump 14 that draws blood from the patient into the artificial lung 10. The pump 14 directs desaturated blood through one or more photolytic cells 16 where light activation (for example, laser at 350-390 nm) results in oxygen generation and ultimate carbon dioxide removal via a carbon dioxide sorption device 24 or external ventilation. A power supply 18 or optional battery 19 activates the light source 20. The light source 20 emits light photos 21 which irradiate the photolytic cells 16. In turn, the photolytic cells 16 photochemically initiate a series of chemical reactions that produce oxygen and remove carbon dioxide from the blood. Oxygenated blood travels from the artificial lung 10 back to the patient by way of a blood outlet 22. Consequently, the artificial lung 10 takes blood from the venous circulation of a patient and returns it to the arterial circulation.

The present photolytic artificial lung omits the gaseous state that causes problems which have limited other blood oxygenation technologies, while consuming carbon dioxide. It also eliminates the need for an external oxygen source and minimizes the risk of inflammation produced by hollow fiber technology.

Also, the present photolytic artificial lung does not require the careful control of temperature or pressure. As briefly mentioned above, all materials for use in the present photolytic artificial lung remain as insoluble solids to prevent blood contamination. Blood contact with the coatings is minimized. Diffusion layers, which can decrease oxygenation rates, are minimized using electrical conduction of electrons and cations to and from the photolytic site, as is done in photosynthesis, by incorporating thin films having good photolytic transparency, and electrical and electrochemical conduction.

The wave length, beam size, pulse duration, frequency and fluency of the light source are adjusted to produce maximum and/or efficient gas exchange. Similarly, pump rate, flow-through capacity, etc. of the photolytic cells are also so adjusted. This is accomplished by sensors and regulators which also monitor reaction chemistry, toxins, etc. The sensors and regulators have the capacity to auto-regulate various parameters of the system in response to the conditions monitored by the sensors.

Most preferably, the photolytic artificial lung is designed to provide at least about 150 ml of dissolved oxygen per minute at 5 L/min of blood flow through the system for a human patient. Also, the components utilized for the photoactivated gas exchange are biocompatable.

Figure 18:
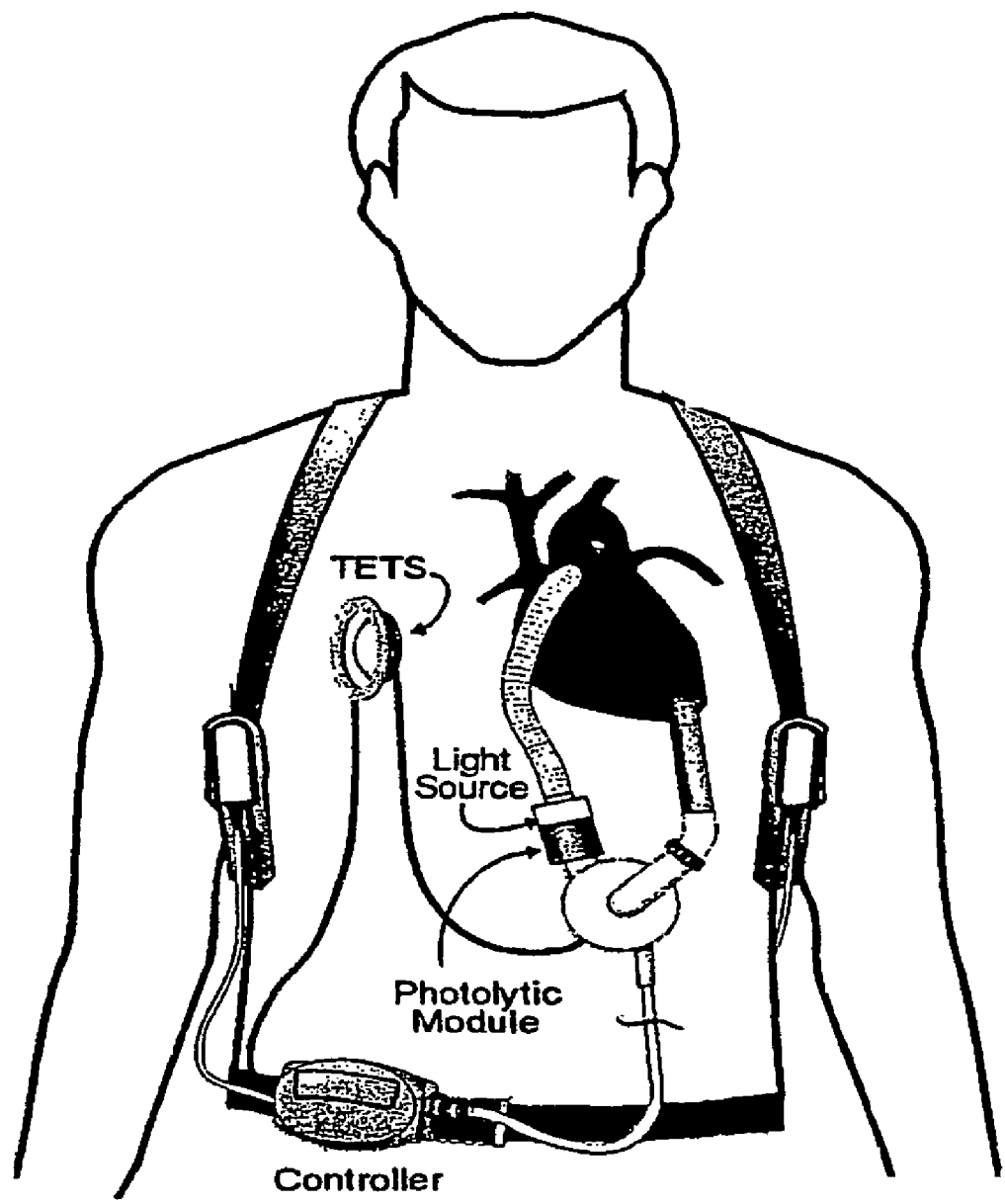
FIG. 18 illustrates a totally implantable heart-lung device utilizing the photolytic cell (module) of the present invention in series with an implantable ventricular assist device with a common power source and controls.

The photolytic artificial lung can be designed so that it is an extra corporeal device or an intra-corporeal device. For example, the photolytic artificial lung can be designed as a miniaturized, implantable unit. Such a unit is configured to be implantable and it uses a transcutaneous energy transmission system and/or an internal light source for energy conversion. See, for example, FIG. 18.

Figure 2A:
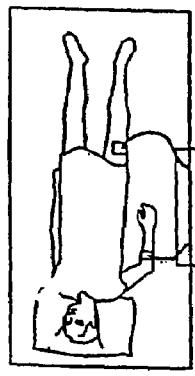
FIGS. 2A-2D illustrate the various embodiments of the photolytic artificial lung set forth in FIG. 1.
Figure 2B:
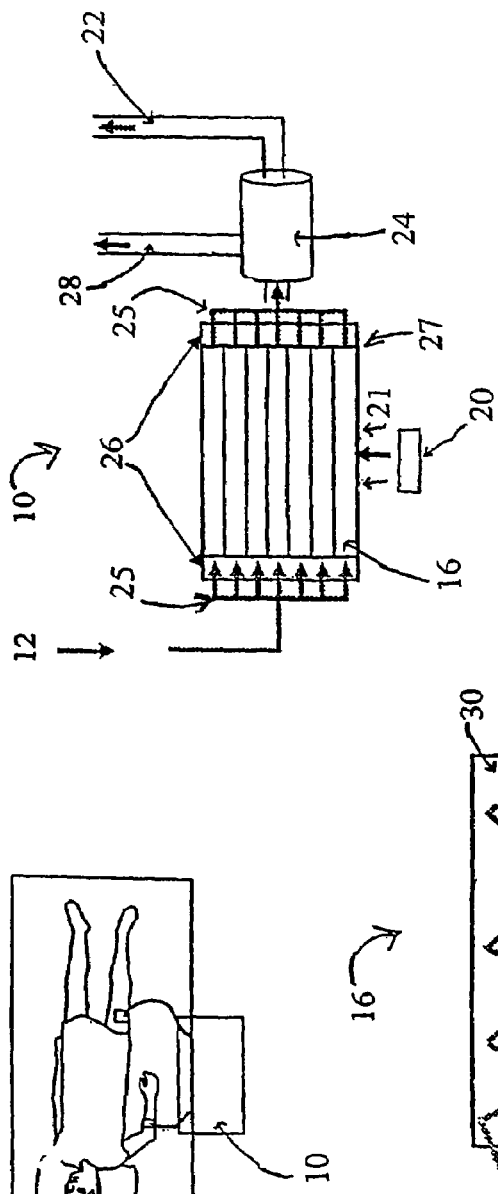
Figure 2C:
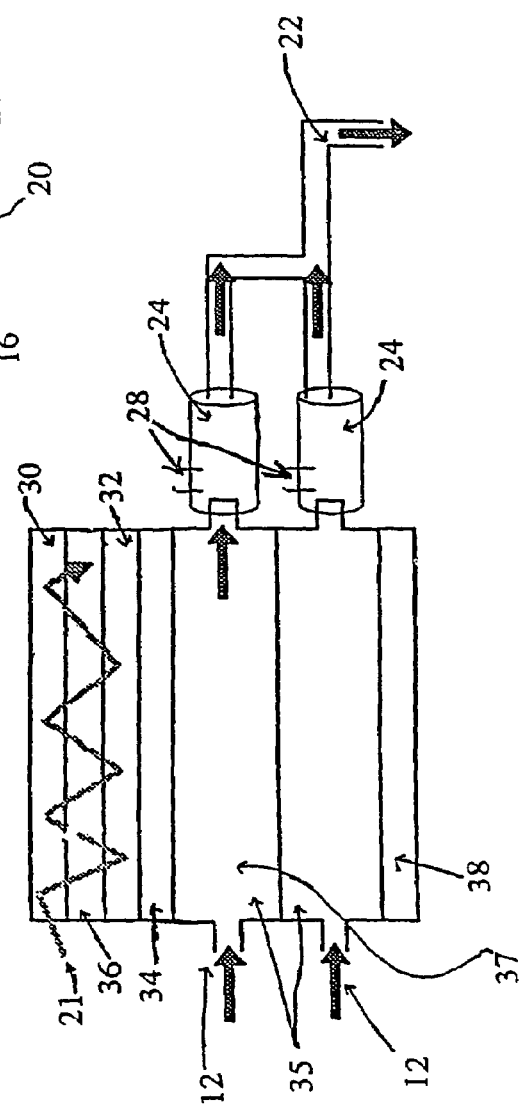
Figure 2D:
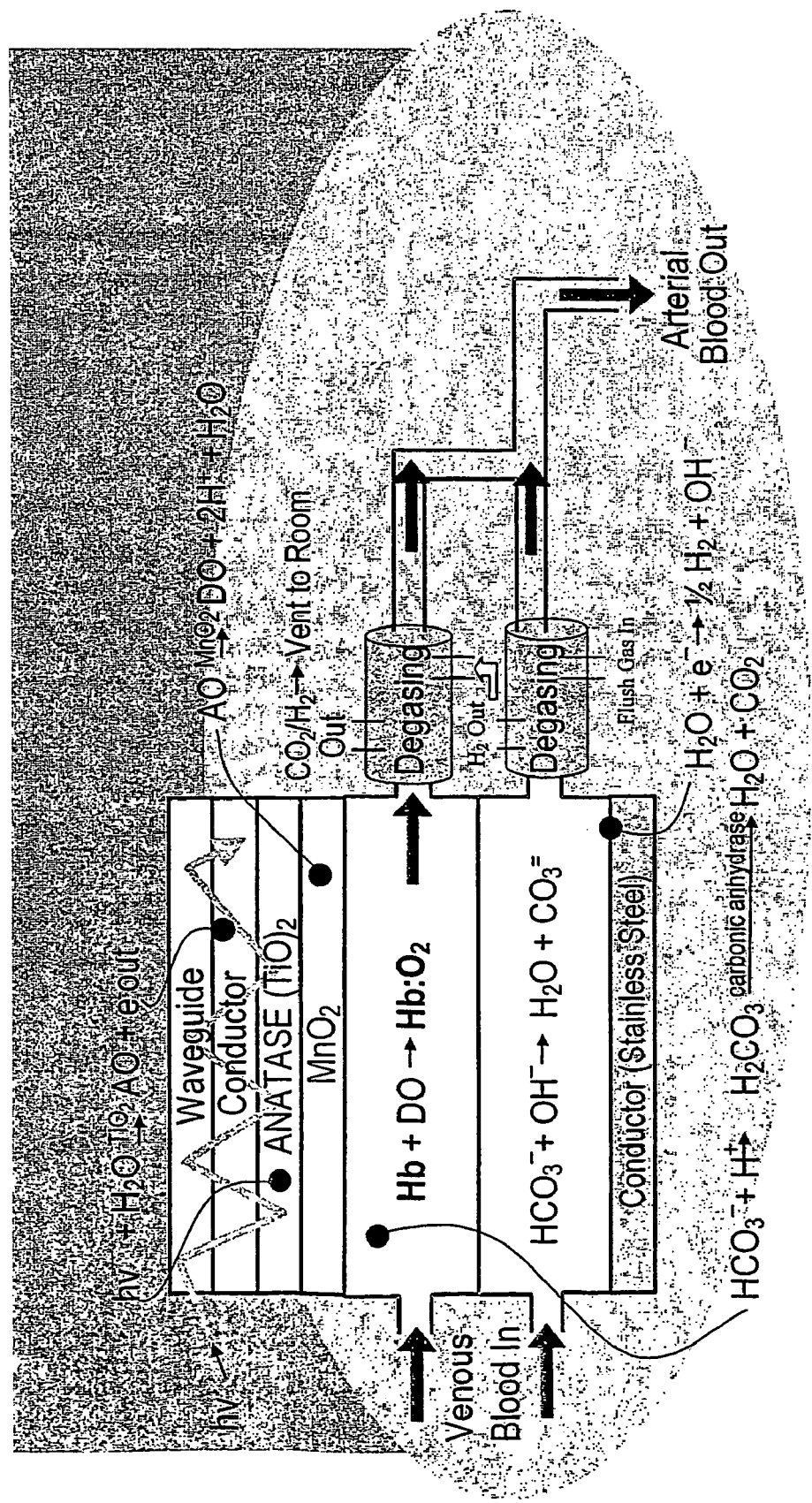

FIG. 2A shows a simple representation of a patient attached to a photolytic artificial lung 10 as an extra-corporal device. FIGS. 2B and 2C are enlargement views showing the components of various embodiments of the photolytic artificial lung 10. FIG. 2D shows the chemical transformations which occur in each compartment of the various embodiments of the artificial lung.

The photolytic artificial lung 10 pumps venous blood from the patient to the photolytic artificial lung 10 through a blood inlet 12. The venous blood enters by means of a flow distributor 25 into one or more photolytic cell(s) 16. The photolytic cell(s) may be optionally arranged to form a stack of photolysis cells 27. The amount of blood entering and leaving the photolytic cell(s) 16 is controlled by flow distributor 25. See FIG. 2B.

A light source 20 irradiates the photolytic cell(s) 16, thereby initiating the photochemical reactions within the photolytic cell(s) 16 that ultimately form dissolved oxygen that binds to blood hemoglobin (Hb). Excess carbon dioxide and hydrogen formed from the chemical reactions in the photolytic cell(s) 16 enter one or more gas sorption devices 24 for storage and/or eventual venting through a venting outlet 28. Once the blood has been oxygenated, and the carbon dioxide removed, the blood returns to the artery of a patient by way of blood outlet 22. Among the components of the photolytic artificial lung not illustrated in this embodiment is the blood pump, power supply, control electronics and sensory technology for monitoring reaction chemistry, the amount of oxygen, carbon dioxide, etc. generated the presence of potential toxins, etc.

The main component of the photolytic artificial lung is the photolytic cell 16. See, for example, FIG. 2C. Light energy 21 from a light source 20 enters the photolytic cell 16 through a transparent substrate or window 30 and activates a layer of light-activated catalyst 32. As discussed in more detail below, an example of such a light activated catalyst is anatase ($TiO_2$). Depending on the catalyst 32 used, the light-activated catalyst 32 converts water into intermediate active oxygen, hydrogen ions and excess electrons, or directly converts water into dissolved oxygen. An optional second catalyst, i.e. a disproportionation catalyst, 34 can be used to convert the intermediate active oxygen to dissolved oxygen, $O_2$. An example of such a second catalyst is manganese dioxide ($MnO_2$). Excess electrons are formed during the conversion of water to dissolved oxygen and are conducted out from the catalyst 32 to an anode conductor layer 36 such as gold or titanium metal film. In chamber 37, the dissolved oxygen binds to hemoglobin (Hb) in the blood and the oxygenated blood returns to the patient via an arterial blood outlet 22.

Additionally, in chamber 37, bicarbonate ions which are also present in the deoxygenated blood react with the hydrogen ions generated above to form carbonic acid. The carbonic acid is then converted to water and carbon dioxide by carbonic anhydrase. The water formed reacts with electrons at the cathode 38 to form hydrogen gas ($H_2$) and hydroxyl groups. The hemoglobin also releases carbon dioxide when the oxygen binds to the hemoglobin. The excess carbon dioxide and hydrogen created from the reactions occurring in the photolytic cell 16 enter one or more gas sorption devices 24 for storage or venting.

Figure 3:
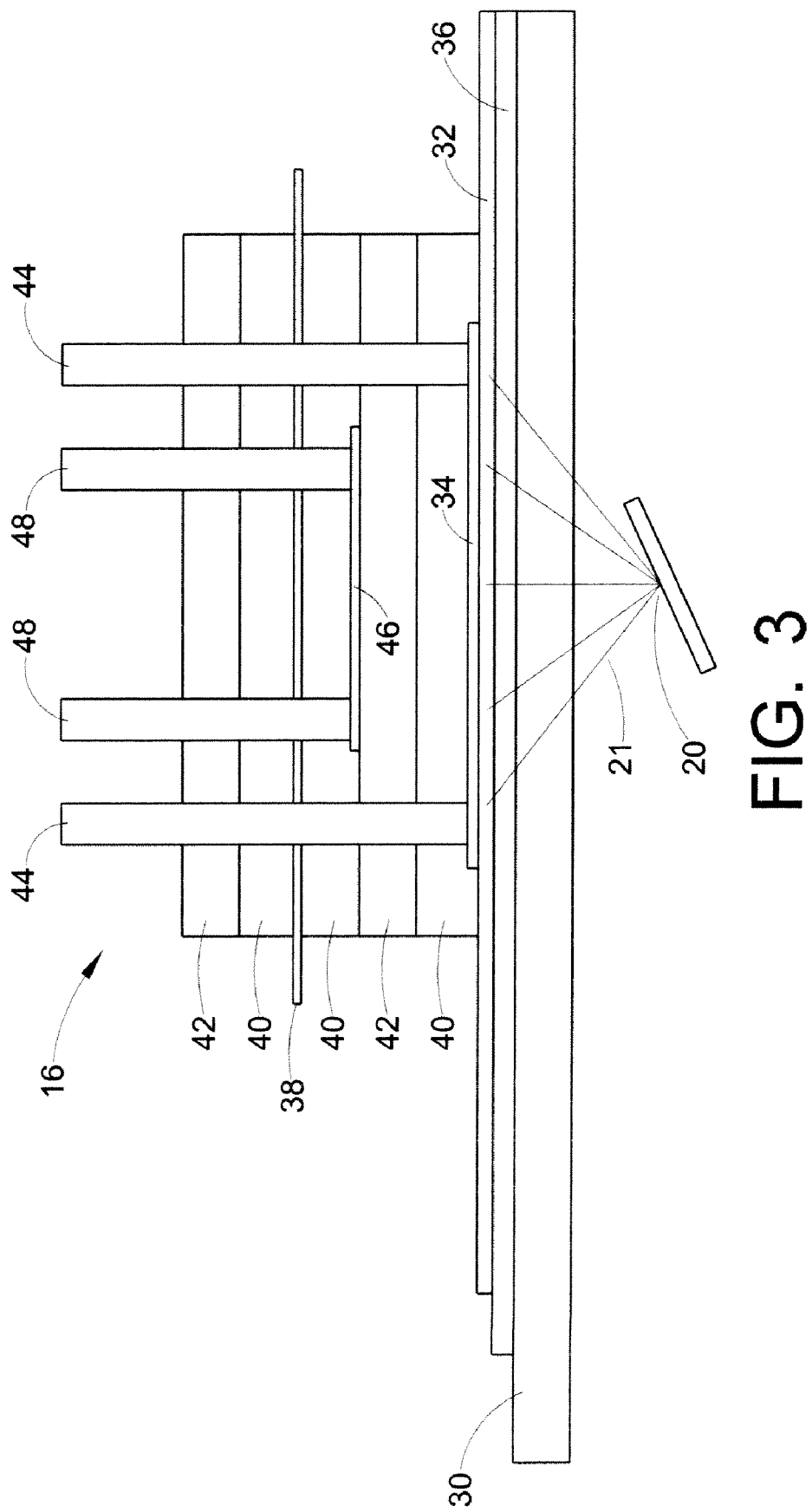
FIG. 3 shows a schematic view of the model photolytic cell apparatus which was used to collect the laboratory data set forth herein. Among other things, this view depicts the relative positions of the coated test surface, light source, and the chemical sensor in place to monitor the chemical yield of the system.

FIG. 3 shows a flow-through embodiment of the photolytic cell 16. In the flow-through cell embodiment, the following main components of the photolytic cell 16 are assembled, i.e. a conductive coating of vacuum deposited Ti metal 36, a coating of adherent $TiO_2$ (anatase) 32, an optional $MnO_2$ particulate layer 34, and then tested using a bicarbonate solution. A UV laser light 20 was shown on the transparent glass or quartz substrate 30 so to initiate the reactions. As discussed below, this cell was utilized to collect pH and data as a function of laser U.V. irradiation demonstrating the effectiveness of the invention.

In this regard, the photolytic cell 16 of FIG. 3 includes a transparent window 30 or wave guide for the entry of light energy in the form of photons 21 from a light source 20 such as an ultraviolet laser light. On one side of the glass slide is an anode conductor layer 36, such as titanium (Ti) metal film. Attached to the anode conductor layer 36, is a layer of a light activated catalyst 32 such as anatase ($TiO_2$). An optional catalyst layer 34, such as manganese dioxide, is adjacent to the light activated catalyst layer 32. The photolytic cell 16 includes one or more layers of silicone gaskets or spacers 40 and an acrylic housing 42. A pair of anolytes 44 (in/out) are connected to the light activated catalyst layer 32 or optional catalyst layer 34 and extend through the photolytic cell 16 away from the transparent window 30. The photolytic cell 16 further includes a cation exchange member 46, such as a NAFION® membrane from DuPont. A pair of catholytes 48 (in/out) are connected to the cation exchange member 46 and extend outwardly through the photolytic cell 16 generally away from the transparent window 30. The photolytic cell 16 further includes a cathode layer 38, such as Pt foil, adjacent to the cation exchange member 46. The operation and use of this embodiment of the invention is more particularly described in the Examples below.

Figure 4:
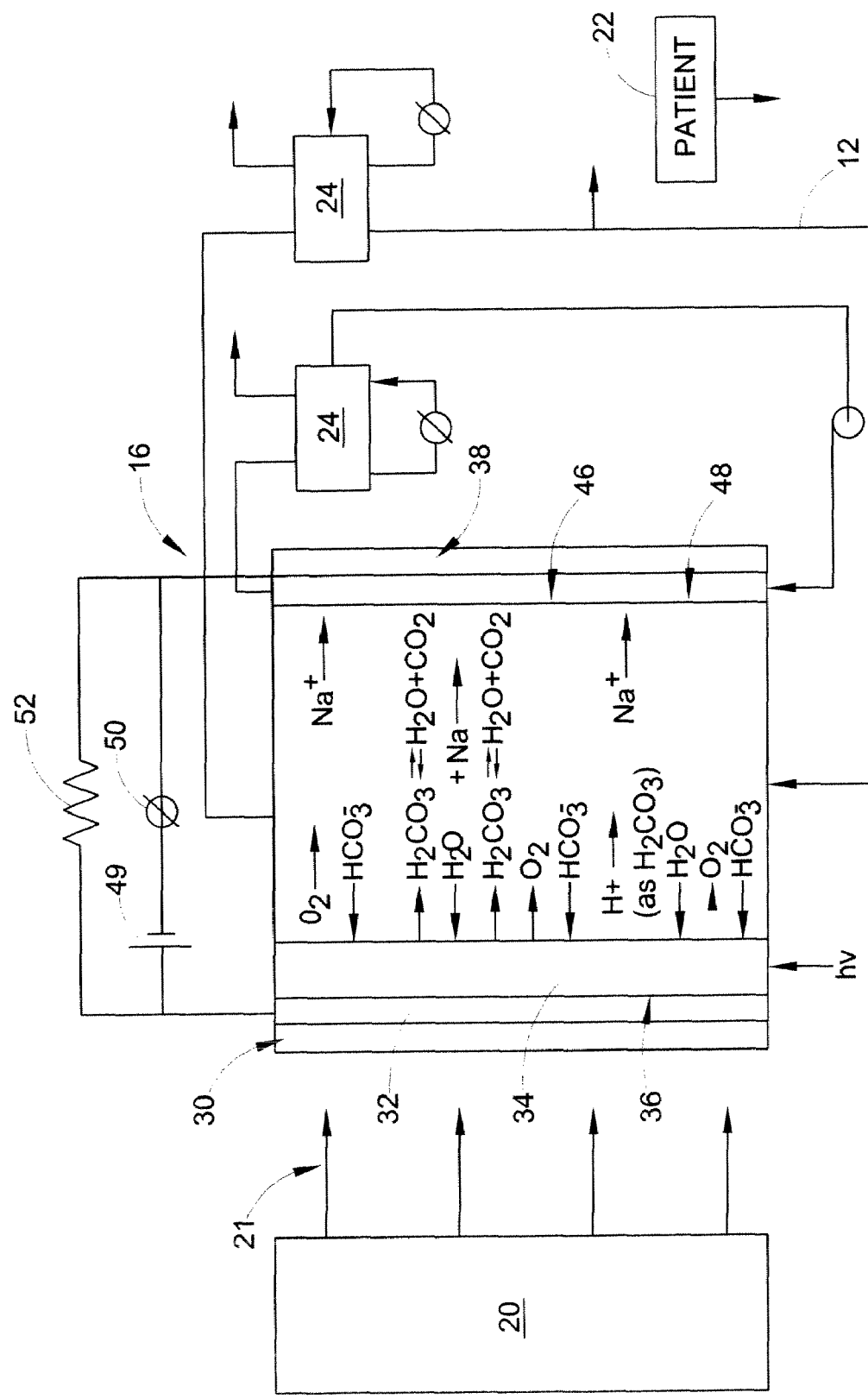
FIG. 4 shows an overall schematic diagram of the preferred embodiment of the photolytic artificial lung of the present invention.

FIG. 4 is a schematic drawing showing the electrical and chemical transformations which occur in the photolytic cell 16 of the photolytic artificial lung 10. Venous blood (low in oxygen and high in carbon dioxide) from a patient enters the photolytic cell 16 through inlet 12 by way of a peristaltic pump 14. Light photons (hv) 21 generated by light source 20 enter through a transparent window 30 or waveguide and activate the light activated catalyst 32 such as 100 µm $TiO_2$ (anatase). The light activated catalyst 32 either directly converts water to dissolved oxygen or converts water to active oxygen and hydrogen ions and an optional second catalyst 34, such as manganese dioxide ($MnO_2$) on a porous film, converts active oxygen (e.g. $H_2O_2$) into dissolved oxygen (DO). The dissolved oxygen then binds to hemoglobin present in the blood.

The electrons released from the conversion of water to oxygen are collected in the collector electron anode 36. An electrical current formed from a battery 49 allows the electrons to flow from the anode 36 to the cathode 38, such as graphite or nickel, so that the electrons do not react with the active oxygen to cause a back reaction and the reformation of water.

The electrical current and electron flow can be regulated by a current regulator 50 or resistor 52. The electrons can react with water to form hydrogen gas, $H_2$, and a hydroxyl ion ($OH^-$). The hydrogen gas formed is moved to a gas sorption device, where it is stored and/or released (i.e., expired). Sodium ($Na^+$) ions from the blood migrate across the cation exchange membrane 46 and react with hydroxyl ions to form sodium hydroxide (NaOH) in the catholyte 48. The hydrogen ions formed from the conversion of water at the light activated catalyst reacts with bicarbonate ions to form carbonic acid, which is converted by carbonic anhydrase enzyme present in the blood or added to form carbon dioxide and water. The carbon dioxide formed in the photolytic cell 16 along with the carbon dioxide released from the blood is moved to one or more gas sorption devices 24 or vented. The oxygenated blood exits the photolytic cell 16 via an outlet 22 and returns to the artery of the patient.

The various particular components and/or processes of the flow through photolytic cell embodiment of the present invention are described in more detail below:

1. Transparent Substrate or Window 30

The transparent window 30 can be formed from glass, quartz slides, quartz, etc. Glass is useful in forming the transparent window provided that the UV transparency is adequate at the wavelength needed. Quartz slides are also useful because of its high UV transparency. For the transparent window, light entry into and through the transparent window can be from the back, side, or bottom. Edge illumination through the transparent window can optionally include a lens or wave guide.

The transparent window can further include a wave guide. A wave guide uniformly distributes photons (hv) from the light over the surface of the light activated catalyst. Particularly, the wave guide causes the light photons to travel in a path so that the photons maximally contact the entire layer of the light activated catalyst. Light enters the wave guide in the side of the transparent window generally parallel to the surface of the light activated catalyst that is attached to the transparent window. The wave guide allows for maximal light photon contact with the light activated catalyst without directly illuminating the side of the entire light activated catalyst attached to the transparent window. The wave guide also allows form maximal photolytic cell staking because light is not required to directly illuminate the light activated catalyst but rather can be indirectly illuminated by side or edge entry in the transparent window. The wave guide provides additional efficiency to light used in the photolytic cell because the light can be spread across the entire surface of the light activated catalyst.

2. Anode Conductor Layer 36

The anode conductor layer 36 conducts electrons formed from the reaction of water to oxygen out of the anode. The anode conductor layer prevents the electrons from reacting back with the oxygen to reform water, thereby allowing maximal formation of oxygen. The anode conductor layer is applied or attached to at least one side of the transparent window.

The anode conductor layer can be formed at least two different ways. The anode layer can be formed by attaching a thin film of uniform metallic conductor to the transparent window using vapor deposition. The film preferably has a thickness of less than about 0.2 µm. Preferably, the film is formed from gold or titanium. Gold remains metallic at all conditions but can be very efficient at UV light blockage or reflection. Titanium can be oxidized to $TiO_2$ by adding $O_2$ to the deposition chamber to yield a possible catalyst layer with excellent adhesion.

The anode conductor layer 36 can also be formed by using photo-resist technology. Under photo-resist technology, grids are prepared with masks using vapor deposition. Conductor line spacing, width and thickness optimization may be required to prevent excessive attenuation, and provide sufficiently close conductive areas to sweep electrons away from the light activated catalyst layer.

3. Catalysts 32 and 34

A light activated catalyst 32 is coated onto the anode conductor layer. The light activated catalyst is photochemically activated and reacts with water to form dissolved oxygen or a free radical oxygen intermediate that is ultimately converted to dissolved oxygen. The term active oxygen (AO) in the present application defines any free radical oxygen intermediate formed in the photolytically catalyzed reaction of water that is ultimately converted to dissolved oxygen. The active oxygen formed is in the form of a peroxide, such as hydrogen peroxide, $H_2O_2$, or peroxide ion salt, hydroxyl free radical, super oxide ion, etc., and is converted into dissolved oxygen in the presence of a catalyst. The active oxygen formed depends on the light activated catalyst used. Also, depending on the light activated catalyst used, water may be photolytically converted directly into dissolved oxygen without first forming an active oxygen.

Several different catalysts can be employed for producing dissolved oxygen photochemically. One catalyst that can be used to photochemically produce oxygen is zinc oxide. By using zinc oxide, peroxide ($H_2O_2$) is produced directly from water at blood pH. $H_2O_2$ is an excellent form of active oxygen for providing sufficient potential diffusion distance, and also for the disproportionate reaction to dissolved oxygen and water via a solid $MnO_2$ catalyst (similar to green plant $O_2$ generation site) occurring photochemically at <340 nm by way of metal ion assisted disproportionation with catalase and other hydroperoxidases. Zinc oxide film has other positive attributes including, known film formation technology (e.g. via the zinc/nitrate/glycine reaction), low toxicity concerns, and low cost.

An additional catalyst that can be used to photochemically produce dissolved oxygen is tungstate ($WO_3$) that is exposed to visible light and using $e^-_{scb}$ removal. $WO_3$ yields oxygen ($O_2$) directly from water without the need to first produce an active oxygen species. Oxygen is generated stoichiometrically and the "back reaction" is unfavored so that there is not significant competition to the direct formation of dissolved oxygen. Only visible light is needed to generate dissolved oxygen from $WO_3$, no more than about 496 nm. $WO_3$ films present low toxicity concerns. Preferably, the use of $WO_3$ further includes the removal of excess $e^-_{scb}$ formed during oxygen formation from water.

Another catalyst suitable for reacting with water is $TiO_2$ (anatase) irradiation with, followed by dissolved oxygen production at a metal catalyst, such as a $MnO_2$ catalyst, or other similar catalyst $TiO_2$ removes the $e^-_{scb}$ efficiently from the production area in order to ultimately obtain good dissolved oxygen production and minimize any back reaction to reform reactants. The removal of $e^-_{scb}$ is performed through conduction via the semi-conductor property of the $TiO_{2(a)}$ with enhancement via application of a small DC bias voltage. $TiO_2$ irradiation also presents low toxicity concerns. $TiO_2$ provides very high insolubility and kinetic inertness to minimize dissolution and fouling during use and maintenance. Preferably, UV light is chopped or pulsed during $TiO_2$ irradiation to allow time for the chemical reactions to occur since with continuous irradiation causes the $e^-_{scb}$ to accumulate and force a back reaction to form water. A pause in the irradiation allows time for the slower, but still extremely fast irradiation in the range of @sec to msec to occur to occur.

A further catalyst for reacting with water to ultimately form dissolved oxygen is a semiconductor powder (SCP)-filled UV/VIS light transparent thermoplastic film. SCP-filled thermoplastic film is relatively inexpensive to manufacture and form into shape. SCP film is easily moldable, extrudable, cut and machined. SCP can be used very efficiently in surface applied only form. Also, SCP has low toxicity concerns. Optimized commercial products (conductive plastic filler powders) are available with good properties for dispersion, particle-to-particle electrical conductivity (for $e^-_{scb}$ removal), and resistance to sloughing off that can be used with the present photolytic artificial lung.

The following additional preferred conditions may be used for each of the above-mentioned catalysts. First, an application of a small (e.g. up to a few volts DC) bias voltage can be applied to help ensure that the $e^-_{scb}$ is quickly conducted away from the production site. Second, a chopped illumination, instead of a continuously applied. illumination, may allow secondary chemical reactions to occur since the secondary chemical reactions are slower than the photochemical reactions and enhance photo yields by allowing the excited electrons to exit the system and not be present for regeneration of starting material, i.e., water.

Of the above-mentioned catalysts, the $TiO_2$ (anatase) catalyst followed by a second metal catalyst for disproportionabon is the most preferred. When the $TiO_2$ catalyst is used, the light-titania interaction is the first step in the ultimate formation of dissolved oxygen. It is known that surface hydrated particulate $TiO_2$ (anatase) solid, $TiO_{2(a)}$—$OH_2$ or $Ti^{IV}O_{2(a)}$—OH, is an efficient UV light (hv) acceptor at wave lengths <390 nm, resulting in active oxygen formation from sorbed water and hydroxyl groups. The most probable reaction is believed to be:

$$Ti^{IV}O_{2(a)}—OH+h\nu \rightarrow Ti^{III}—.OH^*$$

It is noted that other bonds to Ti have been omitted for clarity. The reactant and product of the above reaction are solid materials. In the above reaction, $H_2O$ is already bonded to the surface of the $TiO_{2(a)}$ catalyst as $H_2O$ or as hydroxyl ion ($OH^-$), i.e. $Ti^{IV}O_{2(a)}$—$OH_2$ or $Ti^{IV}O_{2(a)}$—OH, respectfully. Hence, no atoms are required to move during the very fast photon absorption process. The * represents a low lying excited electronic state where the energy of the photon is used to transition or excite an electron from a nonbonding orbital on the oxygen to a molecular orbital centered on the titanium ion, hence converting the titanium into a trivalent oxidation state. The molecular orbital centered on the titanium ion is known to be a part of the semiconduction band ("scb"), and so the electron is readily conducted away from the site to form a bipolar charged grain, or, if connected to a closed DC electrical circuit, resulting in full charge separation, i.e., $$Ti^{III}—.OH^* \rightarrow [Ti^{IV}—.OH]^+ + e^-_{(scb)\uparrow}$$

If the $e^-_{scb}$ is not conducted away or otherwise removed by reaction with an oxidant present in the solution, the $e^-_{scb}$ could react with the hydroxyl free radical and reverse or back react so that the system would return to its original state and form water. In this latter case there would be no net reaction and the photolytic energy will appear as a small amount of heat. Hence the charge separation process and removal of $e^-_{scb}$ is considered an important first step of the photolytic cell dissolved oxygen generation process.

The hydroxyl free radical (.OH) group present is used to represent the initial form of the active oxygen generated by the photolytic process. It is not certain that .OH is the dominant species present when $TiO_{2(a)}$ is photolyzed. The active oxygen formed could generally be in the form of a superoxide, hydrogen peroxide, or a hydroxyl free radical. However, the form of this active oxygen produced has sufficient thermodynamic driving force to form active oxygen from water. For the $TiO_{2(a)}$ catalyst at neutral pH, these highly reactive hydroxyl free radicals either back react as described above, or rapidly dimerize to form (μ-peroxo) titanium (IV) and hydrogen ions, i.e.

$$2Ti^{IV} - \cdot OH \xrightarrow{Fast} Ti^{IV}—O—O—Ti^{IV} + 2H^+$$

These $H^+$ ions are valuable for blood-$CO_2$ level control. The rate of dissolved oxygen production is the rate at which the active oxygen splits out to form $O_{2(aq)}$ and reforms $TiO_2$ (a), i.e.

$$Ti^{IV}—O—O—Ti^{IV} \rightarrow Ti^{IV}—O—Ti^{IV} + \frac{1}{2}O_{2(aq)} \text{ (as dissolved oxygen)}$$

In an unwanted but unharmful second side reaction, any $O_{2(aq)}$ produced can react with $e^-_{scb}$ previously produced but not yet conducted away. These $e^-_{scb}$ negative charges tend to reside on the surfaces of the $TiO_2$ particles so that the negative charge are most separated. Therefore, these $e^-_{scb}$ electrons are available for reduction reactions with $O_2$ or the μ-peroxide linkage to produce species such as $O_2^-$, $O^=$, $O^-$, etc., thereby decreasing dissolved oxygen yields. In order to minimize side reaction, the illumination is pulsed instead of continuous. The delay caused by illumination pulsation allows the $e^-_{scb}$ to be conducted away in one direction and the dissolved oxygen to diffuse away in another (E. Pelizzetti, M. Barbeni, E. Pramauro, W. Erbs, E. Borgarello, M. A. Jamieson, and N. Serpone, *Quimica Nova (Brazil)*, 288 (1985)). Also, illumination pulsation prevents the local populations of $O_{2(aq)}$ and $e^-_{scb}$ from becoming so high that reaction between them becomes fast. The pulse rates involved are extremely short in the μsec-msec range so that there is little effect on $O_{2(aq)}$ production rates. Enhanced yields are also possible for photolytically established charge separation when a bias voltage is present across the coating. (X. Z. Li, H. L. Liu, and P. T. Yue, *Envison-Sci-Technology*, 2000, 34, 4401-4406.) A small bias voltage may also be used to further reduce the amount of $e^-_{scb}$ present and produce more dissolved oxygen.

Another way to increase the amount of dissolved oxygen production in the $TiO_{2(a)}$ system is to provide a means to speed the rate of release of the trapped μ-peroxide as hydrogen peroxide as to active oxygen.

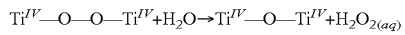

$H_2O_2$ is an excellent form for the active oxygen species as it readily migrates and is easily catalyzed to disproportionate into dissolved oxygen and water.

Stable free radicals (SFRs) can be used to release the trapped @-peroxide as hydrogen peroxide. SFRs can exist as free radicals for extended periods of time relative to the hydroxyl free radical. SFRs have been found useful for promoting electron transfer reactions. They electronically and reversibly rearrange into reduced or oxidized species one electron at a time as set by the reaction conditions. Biological systems are known to use SFRs as respiratory carriers, such as quinone coenzymes including ubiquinone, vitamin K, etc. The SFR shuttles the reactivity from the point of generation to the point of $H_2O_2$ production, or even directly to the metal ion $MnO_2$ catalyst for dissolved oxygen production. Components found in biological systems such as vitamins E, C, K, etc. also may function in the role of SFRs except without recycle. At least four classes of SFRs exist from which a suitable agent can be selected: hindered hydroxylated aromatics (quinones, substituted phenolics); organic peroxide precursors (alcohols, etc.); peracid precursors (acylating agents, etc.); and nitroxides, RN→O.

Therefore, for the $TiO_{2(a)}$ photocatalyst to be useful, a means for releasing the μ-peroxide energy is needed, such as soluble $H_2O_2$, since $H_2O_2$ can diffuse to the $MnO_2$ for dissolved oxygen production, or by conducting the oxidizing power to another active oxygen form, such as SFRs in the adjacent solution that can be used in dissolved oxygen production, or using the $Ti^{IV}$—O—O—$Ti^{IV}$ content to electronically remove electrons from the $MnO_2$ cluster/particle (as is done in green plant photosynthesis by the "D" protein). In the last means, only an electron flows from the water through the $MnO_2$ to the μ-peroxo linkage through delocalized bonds. This electron replaces the $e^-$ lost from the $TiO_{2(a)}$—OH system as $e^-_{scb}$.

The formation of $H_2O_2$ as the active oxygen is valuable since $H_2O_2$ can be rapidly converted to dissolved oxygen in 100% yield using many different methods: thermally; metal ion catalysis; particulate/surface catalysis; base catalysis; and free radical reaction with reductant initiation. Preferably, metal ion catalysis, such as, $MnO_{2(s)}$, provides an efficient catalyst for $H_2O_2$ disproportionation to water and $O_2$, on thin film substrate constructs.

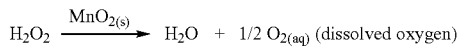

Photo catalyst systems such as zinc oxide, ZnO, release peroxide as the active oxygen more readily than does $TiO_2$. Less acidic metal ions under the Lewis acid/base theory definition cannot sufficiently stabilize the highly alkaline peroxide ion relative to water protonation ($Pk_{a1}$ of $H_2O_2$ is 11.38 (25° C.)) to form it within the solid phase, and so hydrogen peroxide, $H_2O_2$, is readily formed from ZnO:

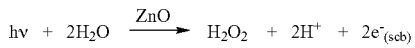

ZnO films and particles can be prepared in a number of ways with varying but controlled composition, morphology and porosity. For example, mirrors of zinc, doped zinc, and zinc alloys and can be sputtered down onto an optically transparent support, followed by oxidation with $O_{2(g)}$. This treatment produces a metal/metal oxide (Zn/ZnO) film. Another highly effective approach to semiconducting ZnO-based films is to utilize a process for optical glass coatings. (L. R. Pederson, L. A. Chick, and G. J. Exarhos, U.S. Pat. No. 4,880,772 (1989).) The optical glass coating technique is based on applying a zinc nitrate/glycine aqueous solution as a dip or spray, followed by drying (110° C. for 15 min), then heating (450-500° C. for 3 min) to initiate a self-oxidation reaction during which the carbon and nitrogen exits as gases leaving an adherent yet porous film bonded to the underlying surface (e.g. glass) and is referred to as the glycine nitrate process. (L. R. Pederson, L. A. Chick, and G. J. Exarhos, U.S. Pat. No. 4,880,772 (1989).) The ZnO film is normally produced doped with alumina by including aluminum nitrate in the aqueous formulation for the initial dip. Many other metal ion blends are also possible with this technique.

Tungstate only requires visible light to produce dissolved oxygen, and produces dissolved oxygen directly without requiring a second catalyst to form dissolved oxygen. The lower photon energy requirement for $WO_3$ is due to the smaller band gap of 2.5 eV versus at least 3 eV for $TiO_{2(a)}$. As with the $TiO_2$ anatase system, high yields are possible with the $WO_3$ catalyst if the $e^-_{scb}$ is removed. The production of $O_2$ increases very significantly if $RuO_2$ (ruthenium oxide) is placed on the surface of the $WO_3$. This is consistent with the fact that $RuO_2$ is a known good catalyst for $O_2$ production and so represents a route to improving other approaches.

An advantage may exist if the dissolved oxygen producing film could be a filled plastic. Such materials are often inexpensive and manufactured easily. Commercial sources exist for semi-conducting, low light absorbing, inorganic fillers for plastics which are supplied in ready made condition for incorporation into plastics, making the plastics electrically conductive. For example, E. I. duPont Nemours, Inc. sells electroconductive powders (EPC) under the trade name ZELEC® ECP for such purposes. The conductive substance in ZELEC® ECP is antimony-doped tin oxide ($SnO_2$:Sb). The bulk of these materials, onto which the conductor is coated, are familiar inorganics such as mica flakes, $TiO_2$, and hollow silica shells, or ECP-M, ECP-T and ECP-S respectively. Pure $SnO_2$:Sb -based material is designated ECP-XC and is a much smaller particle than the other materials. About 25-45% by weight of the ECP products are used so that the particles are sufficiently close to each other to provide internal electrical connections throughout the otherwise non-conducting plastic. ECP-S and ECP-M normally perform best for lower concentrations. Thin films of ECP-XC can provide an attractive coating because they are very fine grained and strongly light absorbing.

The $TiO_2$ layer can be formed a variety of ways. The $TiO_2$ layer can be formed by sol gel, drying and baking. A product under the trademark LIQUICOAT® from Merck & Co., Inc., which hydrolyzes $Ti(OR)_4$ type material in water to form $TiO_2$ and 4ROH can be used to form the $TiO_2$ layer under a sol gel/drying/baking process. TiO$_2$ can also be formed from preparing an anatase suspension from dry powder, then dipping, drying, and baking the suspension to form the TiO$_2$ layer. Another way the TiO$_2$ layer can be formed is by e-beam evaporating titanium and subsequently exposing the titanium to O$_2$ within a deposition chamber. The TiO$_2$ layer can also be formed by adding titanium salt to water and adjusting the pH to ~2-7 to form a suspension, then dipping the suspension and allowing the suspension to dry.

Active oxygen is created from TiO$_2$ by irradiation with UV light, but the chemical form of the active oxygen is very reactive and can be lost by side reaction occurring in close proximity to the TiO$_2$ particle surface where active oxygen is generated. There are at least three ways to minimize the loss of active oxygen to unwanted side reaction: 1) move the active oxygen to dissolved oxygen conversion point closer to the active oxygen generation point, i.e. move the metal ion catalyst as close as possible to the TiO$_2$, which may require intimate contact between these two materials, in the order of angstroms; 2) electrically connect the two points, as is done in photosynthesis by a protein capable of conducting electrons; or 3) convert the active oxygen into a longer lived intermediate active oxygen species that has time to migrate to more distant MnO$_2$ centers for conversion to dissolved oxygen.

The amount of active oxygen lost by side reactions can be minimized by introducing an active oxygen carrier molecule into the media, or "D," by analogy to a photosynthetic system. Agents for use with species D can be selected from two groups, those that readily form organic peroxides, and those that form "stable" (i.e. long-lived) free radicals. Organic peroxides are useful because they easily produce dissolved oxygen when contacting MnO$_2$, and readily form by oxygen insertion. The organic peroxide reactions are as follows:

$$[TiO_2]\text{—}Ti^{IV}\text{—}OH + h\nu \rightarrow \{[TiO_2]\text{—}Ti^{III}.OH\}$$

where the excited electronic state corresponds to the ligand-to-metal charge transfer (free radical pair), and is followed by the reaction:

$$\{[TiO_2]\text{—}Ti^{III}.OH\} + H_2O \rightarrow [TiO_2]\text{—}Ti^{IV}\text{—}OH + H^+ + .OH$$

where conduction of the e− into the semiconductor conduction band and away from the side of the particle near the .OH prevents recombination of that e−. As shown in the reaction above, the TiO$_2$ anatase is regenerated. The above reaction produces a hydrogen ion for eventual CO$_2$ removal. Also, the active oxygen produced in the above reaction is in close proximity to TiO$_2$ as a free radical hydroxyl groups, .OH.

As .OH is extremely reactive, lasts only for a very short time and does not diffuse far. One way to increase the amount of time that .OH is present is by introducing a species that stabilizes the .OH. Similar to photosynthesis, a species "D" is introduced into the test system to capture the hydroxyl free radical in a longer lived species. The species D is generally shown the in following chemical reaction:

where D can be RC(O)OH:

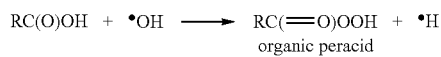

or D can be R$_3$COH:

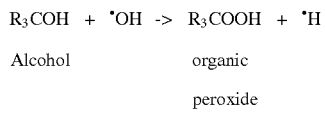

or D can be a free radical scavenger that forms a stable free radical:

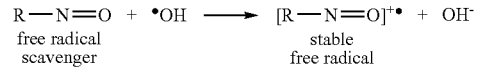

or D can be 2,6-di-tertbutyl phenol:

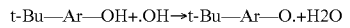

The 2,6-di-tertbutyl phenol is the most desired D species, as a strongly reducing .H radical is not formed that would consume OH− and [TiO$_2$]—Ti$^{III}$ in wasteful reactions, regenerate the starting materials, and result in a low photochemical yield.

The catalyst used to convert active oxygen into dissolved oxygen includes metal ions capable of redox cycling, such as Fe$^{II}$, Fe$^{III}$, Cu$^{I}$, Cu$^{II}$, Co$^{II}$, Co$^{III}$, Mn$^{II}$, Mn$^{III}$, Mn$^{IV}$, etc., or metal oxides formed from metal ions capable of redox cycling, such as manganese dioxide, MnO$_2$. The present reaction produces dissolved oxygen directly from water and by-passes the gaseous state. The MnO$_2$ catalyst is most preferred because it forms dissolved oxygen efficiently and is not highly selective of the active oxygen form.

One way to facilitate the conversion of active oxygen to O$_2$ is by doping the surface of the TiO$_2$ anatase with manganese (Mn). Surface doping the TiO$_2$ with Mn provides a highly productive active oxygen to O$_2$ conversion catalyst. Active oxygen disproportionation is rapid when dropped on a Mn-doped anatase. Alternatively, active oxygen can also be converted to O$_2$ by placing MnO$_2$ on the surface of the anatase in conductive form. In this form, electrons are catalytically passed from water to the active oxygen region of the anatase. Such an arrangement more closely mimics photosynthesis O$_2$ production.

Another way to convert active oxygen to O$_2$ in the photolytic cell is by using a MnO$_2$ octahedral molecular sieve (MOMS) material as the dissolved oxygen catalyst. The MOMS material has an open gel-like structure and is closely related to zeolites in structure. The MOMS material is easily formed from manganese salts through precipitation and drying.

Active oxygen may also be converted to O$_2$ in the photolytic cell by a superoxide dismutase (SOD) catalyst. SOD catalyst is already available in the human body and can provide the required conversion of active oxygen, e.g. as O$_2^-$, into a dissolved oxygen precursor, i.e. H$_2$O$_2$, to supplement the photolytic cell and Mn-doped anatase.

Blood is routinely exposed to active oxygen forms and blood already has built-in measures for self protection against low levels of excessive active oxygen. ("Inorganic Biochemistry", G. L. Eichhorn (Ed)., Chap. 28, p 988 (Elsevier, Scientific Publ., NY (1975), and "Advances in Inorganic and Bioinorganic Mechanisms", A. G. Skes (Ed), p 128 (1986) (Academy Press, NY)) Active oxygen forms within the body in the form of species such as peroxides (R—O—O—H) and superoxide (O$_2^-$$_{(aq)}$), which are disproportionated to dissolved oxygen and H$_2$O respectively by hydroperoxidases, such as catalase which contains zinc ion, peroxidase which contains iron ion, etc., and superoxide dismutase metal ion-based enzymes, such as ferriprotophyrin IX. Alternatively, these enzymes can utilize active oxygen forms to oxidize a wide range of chemical reductants such as ascorbic acid and other vitamins such as such as vitamin E and vitamin K. Although the photolytic artificial lung does not rely on such protection mechanisms, it is noteworthy that low levels of such molecules are not new to body chemistry and that conventional mechanisms for handling such exposures exists.

4. Blood Exchange

Hemoglobin from blood follows the following steps of reactions within the photolytic cell.

Hb(h.s. Fe$^{II}$)+O$_2$δHb(l.s. Fe$^{II}$)O$_2$

HbO$_2$+2H$^+$(pH 6.8-7.6)δH$_2$Hb2$^+$+O$_2$

N— of two alpha-chains (pKa$\iota$8.0) and His β146 (pKa$\iota$6.5) residues are bases for H$^+$ reaction

CO$_2$+H$_2$OλH$_2$CO$_3$λH$^+$+HCO$_3^-$

Hb(R—NH$_2$)+CO$_2$λR—NH—COO$^-$+H$^+$

When water reacts with a light activated catalyst, the hydrogen ion that is released rapidly reacts with an HCO$_3^-$ ion and forms H$_2$CO$_3$. The photolytic cell has excess HCO$_3^-$ ions to react with hydrogen ions.

The photolytic cell allows the blood to achieve the proper mass balance. The mass balance of blood traveling through the photolytic cell is as follows:

Hb(RNHCOO$^-$)+2H$^+$ ⇌ HbNH$_3^+$+CO$_2$

HCO$_3^-$ + H$^+$ ⇌ H$_2$CO$_3$ $\xleftarrow{CA}$ H$_2$O + CO$_2$

HbNH$_3^+$+O$_2$ ⇌ Hb·O$_2$+2H$^+$

2H$_2$O+hv ⇌ O$_2$+4H$^+$+4e$^-$

H$^+$4e$^-$+2 quinone ⇌ 2 hydroquinone

Q H$_2$Q

Net Reaction:
Hb(RNHCOO$^-$)+HCO$_3^-$+H$^+$+H$_2$O+hv+2Q ⇌ 2CO$_2$+Hb·O$_2$+2H$_2$Q.

Alternatively, quinone can be replaced with Fe(CN)$_6^{3-}$. The quinone or Fe(CN)$_6^{3-}$ Q could be in homogeneous solution or film form.

5. Cation Exchange Membrane 46

The cation exchange membrane 46 allows for the diffusion of cations in the photolytic cell. Particularly, the cation exchange membrane allows a cation, such as a sodium ion (Na$^+$) from blood to diffuse through the membrane and subsequently form sodium hydroxide (NaOH) in the catholyte. The cation exchange membrane is commercially available under the trademark NAFION® and is available from E. I. du Pont Nemoirs Inc. NAFION® cation exchange membranes are a perfluorosulfonic acid/PTFE copolymer in an acidic form. Although NAFION® cation exchange membranes are the preferred membrane, one skilled in the art would recognize that other cation exchange membranes are also suitable in the photolytic cell.

The anodic compartment of the photolytic cell has the following series of reactions:

hv + 2H$_2$O $\xrightarrow{TiO_2}$ "AO" + 2H$^+$ + 2e$^-$

AO $\xrightarrow{MnO_2}$ 1/2 O$_2$ + H$_2$O

2H$^+$ + 2HCO$_3^-$ ⟶ 2H$_2$CO$_3$

2H$_2$CO$_3$ $\xrightarrow{CA\ cat.\ \&\ uncat.}$ 2H$_2$O + 2CO$_2$

2 CO$_2$ ⟶ 2CO$_{2(g)}$

1/4 Hb + 1/2 O$_2$ ⇌ 1/2 Hb:O$_2$

The overall net anodic reaction from the above reactions is as follows:

hv+¼Hb+2NaHCO$_3$→2CO$_{2(g)}$μ+H$_2$O+½Hb$_{0.5}$O$_2$+ 2e$^-$+2Na$^+$

The two electrons formed in the anodic reaction are conducted away to the cathode via the anode conductor layer. The two Na$^+$ ions are moved to a catholyte via a cation exchange membrane.

6. Catholyte 48

Sodium hydroxide (NaOH) builds in the catholyte during the series of reactions in the photolytic cell. It is preferred that the NaOH is purged occasionally from the catholyte. If sodium chloride (NaCl) is used in the catholyte instead of NaOH, NaCl(s) may eventually form within the catholyte and would periodically be purged.

The reactions occurring in the cathode of the photolytic cell are as follows:

2NaHCO$_3$λ2Na$^+$+2HCO$_3^-$

2e$^-$+2H$_2$O+ ⇌ H$_{2(g)}$+2OH$^-$

2OH$^-$+2HCO$_3^-$ ⇌ 2CO$_3^=$+2H$_2$O

4Na$^+$+2CO$_3^{2-}$λ2Na$_2$CO$_3$

The overall net cathodic reaction is as follows:

2e$^-$+2Na$^+$+2NaHCO$_3$→H$_{2(g)}$μ+2Na$_2$CO$_3$

The Na$_2$CO$_3$ that is produced causes pH to rise. Based upon the overall anodic and cathodic cell reactions, the overall net photolytic cell reaction is:

hv+¼Hb+4NaHCO$_3$→H$_{2(g)}$+2Na$_2$CO$_3$+2CO$_{2(g)}$+ H$_2$O+½Hb$_{0.5}$O

7. Battery/Current Regulator

As shown in FIG. 4, the photolytic cell can include a battery 49, current regulator 50, or resistor 52. An electrical current formed from a battery 49 allows electrons to flow from the anode 36 to the cathod 38. The intial bias voltage caused by the current supplied from the battery initiates the removal of electrons formed during the conversion of water to dissolved oxygen and prevents the electrons from reacting with the active or dissolved oxygen to reform water. The initial bias voltage also allows more dissolved oxygen to be produced as the removal of the electrons minimizes the reformation of water. Additional external electrical contacts can monitor or apply a particular voltage to the photolytic cell.

The current regulator and resistor help control the flow of electrons from the anode to cathode, thereby controlling the amount of dissolved oxygen formation. The resistor creates a fixed control in the current flow, whereas the current regulator can be adjusted to increase or decrease the resistance of the current flow. Increasing the resistance of the current lowers the number of electrons flowing from the anode to the cathode, thereby lowering the overall production of dissolved oxygen. Decreasing the resistance of the current increases the flow of electrons from the anode to the cathode, thereby increasing the amount of dissolved oxygen produced.

8. Optimal Gas Sorption Device 24

Continual venting of carbon dioxide gas out of the photolytic cell presents the problem of potential infection. A gas sorption device minimizes and provides control over potential infection risks by avoiding continuous venting of the $CO_2$ to the atmosphere. The gas sorption device captures $CO_2$ gas released from the oxygenated blood in a concentrated form. The concentrate can be processed or disposed of occasionally so that the sterility of the photolytic cell is not continuously subjected to possible contaminants due to the continual venting of the $CO_2$ gas.

$CO_2$ can be captured using a number of different ways by a gas sorption device 24. The gas sorption device can use the process of chemi-absorption and convert $CO_2$ into a concentrated solid or solution form. The concentrate formed in the gas sorption device can then be disposed of as disposable cartridges having liquid or solid $CO_2$, or regenerated.

Figure 5:
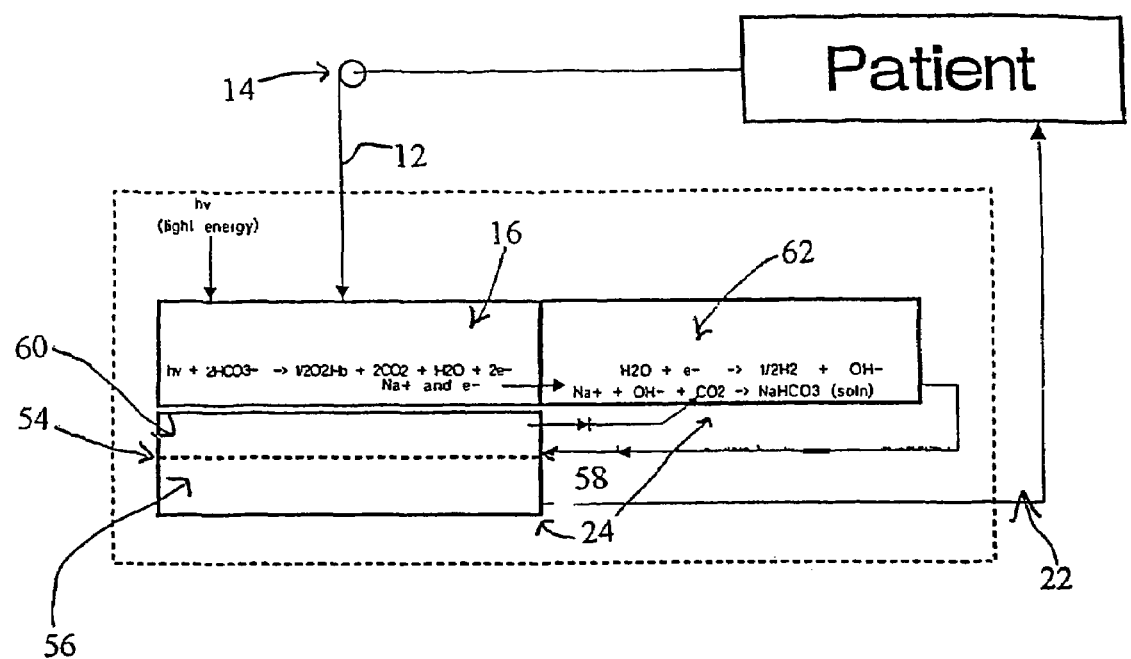
FIG. 5 shows a diagram of the gas sorption device.

FIG. 5 shows the general schematic of the gas sorption device 24 and path of $CO_2$ to the gas sorption device 24 for absorbing $CO_2$. The photolytic cell 16 forms dissolved oxygen that associates with the deoxygenated blood flowing through the cell. The $CO_2$ produced in the anode of the photolytic cell 16 from the conversion of bicarbonate ion to carbonic acid is present as small bubbles as a result of carbonic anhydrase activity. These bubbles are readily released within a coalescence compartment 54 so that the use of membranes are avoided. Four moles of $CO_2$ gas is released per mole of $O_2$ gas formed. When $O_2$ is formed at the targeted flow of 150 cc/min gas at STP, the moist $CO_2$ flow rate is about 600 mL/min at STP. $CO_2$ is trapped when entering the coalescence compartment 54 by a gas coelesor 56. In or near the bottom of the gas coalesor 56 an entry point 58 exists for hydrogen gas ($H_2$) coming from the cathodic compartment. The $H_2$ gas merely sweeps across the head space 60 above the gas coelesor 56 in the coalescence compartment 54 and collects $CO_2$ gas. The flow is provided by the same pump 14 that is used to provide the photolytic cell 16 with blood since the photolytic cell 16 is either a fully liquid-filled closed system, or a cascading overflow (but non-portable) system. The $CO_2$/$H_2$ gas mixture exits the top of the gas head space 60, near the blood entry point. When $O_2$ is formed at the targeted flow of 150 cc/min gas at STP, the $H_2$ flow rate is at least about twice the $O_2$ flow rate or 300 mL/min (STP). The gas mixture then flows to a sorber 62.

Figure 6:
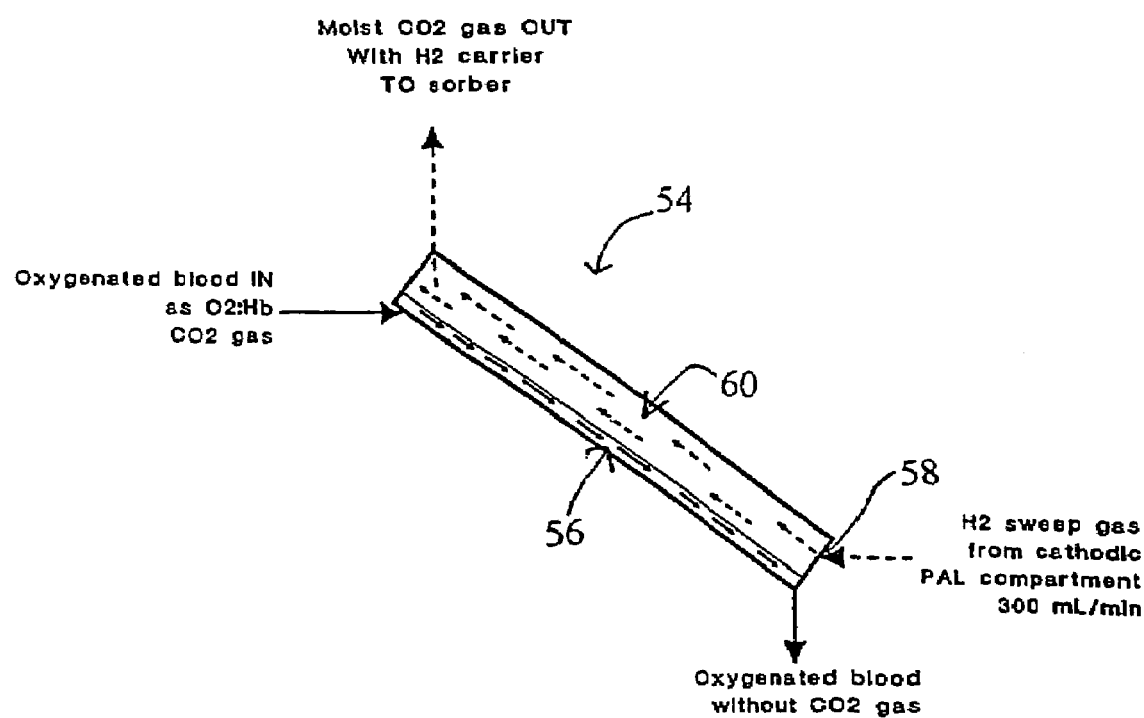
FIG. 6 shows a schematic diagram of the coalescence collector.

FIG. 6 shows a coalescence compartment 54. The coalescence compartment 54 can be a small plastic reservoir having a relatively small volume, and can be any shape. Preferably, the coalescence container 54 has a downward tilt. The whole blood travels through the coalescence container 54 through the coelesor 56 and returns to the patient at the bottom of the tilt. $H_2$ gas enters at an entry point 58 into the gas head space 60 and sweeps the $CO_2$ through the gas head space 60 and into a sorber (not shown). The coalescence container 54 can be used as a temperature control point.

Figure 7:
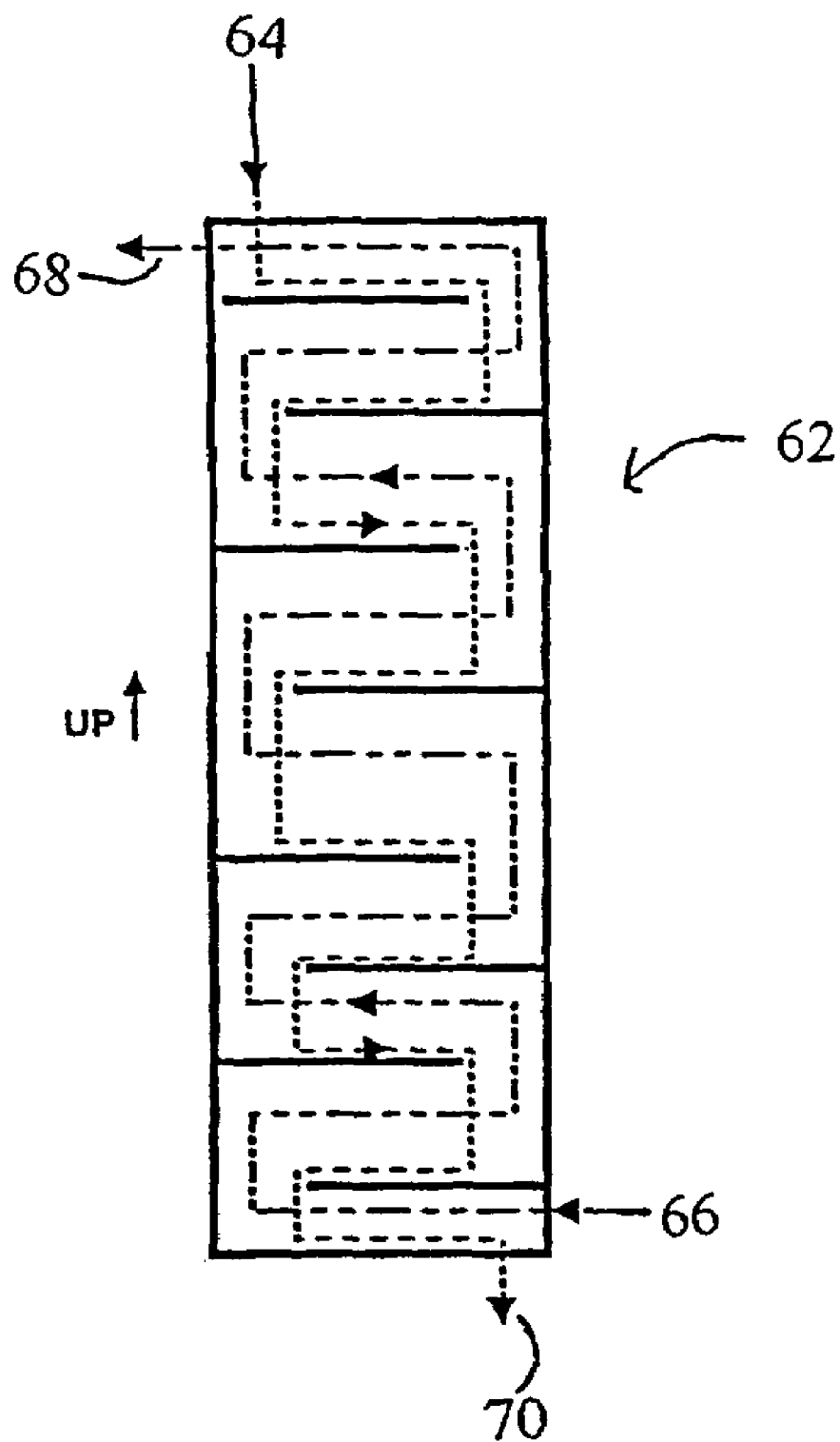
FIG. 7 shows an interior view of the gas sorber device.

FIG. 7 shows a sorber 62. The sorber 62 converts $CO_2$ gas into either a solution or solid depending on the sorbent 64 used within the sorber 62 without the need for mechanical mixing or pumping. The high capacity, low pressure drop, sorber 62 for $CO_2$ gas operates at mild pressure with a gravity feed and without the need for high surface area contactor. The $CO_2$/$H_2$ gas mix enters the sorber 62 at an entry point 66 near the bottom of the sorber 62. Intimate mixing of gas and liquid is accomplished by the 90° flow path changes, cross-path gas/liquid paths, and counter-current configuration. The $CO_2$ reacts with the sorbent 64 in the sorber 62 to form a solid or solution. The solid or solution formed can be removed through an outlet 70. Hydrogen gas can be swept out through a sweeping outlet 68 and be reused in the coalescence compartment (not shown). Preferably, the sorber 62 is small and has a total internal volume of about 25 cc. The entire sorber 62 is contained within the sterile unit. Since blood is not involved in the sorber 62, potentially detrimental effects in the blood are avoided. Also, the large orifices and membrane-free operation prevents potential fouling. The sorber 62 can have a vertical orientation but can also be designed with broad orientation accommodation. The entire sorber 62 is contained within the sterile unit.

The sorbent material 64 within the sorber 62 can be a solid or a solution. As a solution, the sorber can also be the catholyte for the photolytic cell. The sorbent 64 as a solution is consumed at a rate of 2-6 mL/min for the a $CO_2$ gas flow rate of 600 mL/min at STP. The high capacity, low pressure drop, sorber 62 for $CO_2$ gas operates at mild pressure with a gravity feed and without the need for high surface area contacter. Alternatively, the sorber 62 can use a solid sorbent 64 where the sorbent 64 is a packed bed of sorbent granules. Since blood is not involved in the sorber 62, potentially detrimental effects in the blood are avoided. Also, the large orifices and membrane-free operation prevents potential fouling. The sorber 62 can have a vertical orientation but can also be designed with a broad orientation accommodation. Sorbent materials are selected to react with the $CO_2$ gas to form bicarbonates and carbonates as solutions, solids, or combinations of these. Individual sorbents can be blended to obtain synergistic blends which, for example, might react faster, be more cost effective, and/or hold more carbon dioxide equivalents than the pure materials. Table 1 is a list of sorbent materials along with their $CO_2$ capacity equivalents.

TABLE 1

Sorbent Solutions and Solids for $CO_2$

| Sorbent | Solution or Solid | solution density g/cc | % sorbent in solution (20-25° C.) | Maximum molarity of $CO_2$ when fully loaded or of sorbent initially charged. | $CO_2$ sorbing capacity | Chemical Form of Sorbed $CO_2$ |
|---|---|---|---|---|---|---|
| $Na_2CO_3$ | soln | 2.53 | 31.3 (35° C.) | | | $NaHCO_3$ |
| NaOH catholyte (w/OH— from PAL cell) | soln | 1.52 | 50 | 19.01 | | $NaHCO_3$ and $Na_2CO_3$ |

TABLE 1-continued

Sorbent Solutions and Solids for $CO_2$

| Sorbent | Solution or Solid | solution density g/cc | % sorbent in solution (20-25° C.) | Maximum molarity of $CO_2$ when fully loaded or of sorbent initially charged. | $CO_2$ sorbing capacity | Chemical Form of Sorbed $CO_2$ |
|---|---|---|---|---|---|---|
| NaCl catholyte (w/OH— from PAL cell) | soln | TBD | TBD | TBD | TBD | $NaHCO_3$ and $Na_2CO_3$ |
| KCl catholyte (w/OH— from PAL cell) | soln | TBD | TBD | TBD | TBD | $KHCO_3$ and $K_2CO_3$ |
| KOH catholyte (w/OH— from PAL cell) | soln | TBD | TBD | TBD | TBD | $KHCO_3$ and $K_2CO_3$ |
| $CaCl_2$ catholyte (w/OH— from PAL cell) | soln | | 40. | 5.03 | 5.33 cc/ml 320 cc/hr 7.7 L/hr | $CaCO_3$(s) pKsp = 8.32 |
| $Ca(OH)_2$ | solid | TBD | TBD | TBD | TBD | $CaCO_3$(s) pKsp = 8.32 |
| $MgCl_2$ catholyte (w/OH— from PAL cell) | soln | 1.28 | 30.00 | 4.021 | | |
| $Mg(OH)_2$ | solid | TBD | TBD | TBD | TBD | $MgCO_3$(s) pKsp = 9.2 |
| soda lime | solid | TBD | TBD | TBD | TBD | $CaCO_3$(s) pKsp = 8.32 |
| nonvolatile amines (e.g. MEA, DEA, etc.) | soln | TBD | TBD | TBD | TBD | $R_4N^+HCO_3^-$ |

1. MEA and DEA are monoethanol amine and diethanol amine respectively. Polyol amines. polyamines, and zwitterionic materials are other suitable organic $CO_2$ sorbents.
2. $CaCO_2$ is not expected to be regeneratable.
3. Note that the halide salt systems, e.g. NaCl, KCl, $CaCl_2$ and $MgCl_2$, or mixtures thereof as are represented by brines such as Lockes-Ringer solution, saline solution, etc., sorb $CO_2$ by using the cathodically produced $OH^-$, the salt just providing charge balance at the membrane and electrode, and in the sorber/desorber.

$HCO_3^-$ loses $CO_2$ easily and the sorbent can be regenerated thermally, disposed of as a disposable cartridge, or regenerated continuously through the self sterilizing and self-cleaning caustic heating operation at mild temperatures and pressures. Alternatively, the sorbent can be continuously regenerated. For the carbonate sorbent system, the pH will vary from an initial pH of 11.6 to a pH of 8.3 when exhausted and could be monitored using a pH indicator dye or pH electrode.

Hydrogen gas produced in the cathode and used to sweep the $CO_2$ from the blood to the coalescence compartment will accumulate unless vented. $H_2$, being an extremely small molecule, readily diffuses through most non-metallic materials, especially plastics, ceramics, etc. The venting of $H_2$ can be controlled by selecting materials of construction that allow diffusion. No particular membranes, vessels, pumps, filters, one way valves, etc. are required to diffuse $H_2$. The role of $H_2$ as a sweep gas has a very broad range of acceptable flow rates for proper function since the $CO_2$ will self-flow in its absence and a negative pressure will develop in the $CO_2$ sorber as the chemistry is quantitative ($CO_2$ efficiently absorbed down to low $P_{CO2}$ values).

9. Light Supply 20

The light supply is used in the photolytic cell to provide the photon energy necessary to activate the catalyst converting water into oxygen. The light source can be from any known light source including, but not limited to, sunlight, UV light, laser light, incandescent light, etc., depending on the activation requirement for the light activated catalyst used. Preferably, the blood flowing through the photolytic artificial lung is not exposed to the light in order to prevent irradiation of the blood.

The light source may provide a particular wavelength of light depending upon the catalyst used. When tungstate ($WO_3$) is used as a light activated catalyst, the light source exposes visible light in order to activate $WO_3$. When $TiO_2$ or ZnO is used as a light activated catalyst, the light source used has a wavelength in the UV range.

Preferably, the light source used in the photolytic artificial lung is a laser light. The wavelength of laser light can be manipulated in order to attain a higher efficiency in exciting the light activated catalyst and forming active oxygen. Also, laser light allows the photolytic artificial lung to dissipate less overall heat The laser light can be directed in a small area to energize the light activated catalyst and avoid contact or irradiation with other components of the photolytic artificial lung. A particularly preferred laser light that can be used to activate $TiO_2$ is an argon laser at 364 nm (400 mwatts/cm$^2$), which has a total power of about 2 watts, although other UV sources, including an HG arc lamp at 365 nm line, are also available.

It is preferred that the light from the light source be evenly spread within the photolytic cell. The even spreading of the light from the light source allows for maximal excitation of the catalyst in order to convert more water into either active oxygen or dissolved oxygen. Along these lines, light from the light source can enter the photolytic cell through the transparent window from many positions. Light from the light source can enter directly through the transparent window and come into contact with the catalyst. Alternatively, light can enter the transparent window from a side, back, bottom, or corner position and move through the transparent window by a wave guide to provide photon energy and excite the light activated catalyst. Side entry of light into the transparent window of the photolytic cell occurs at about at least a 68° angle. Preferably, side entry of light into the transparent window occurs at an angle of from about 70° to about 80°.

10. Pump

A peristaltic pump or some other simple pump drives blood through the photolytic artificial lung. The pump draws venous deoxygenated blood from a patient and moves the blood through the photolytic artificial lung. Preferably, the photolytic artificial lung only requires a pump to draw blood from a patient, as the flow produced by the pump drawing blood from the patient also moves the blood through the photolytic cell for oxygenation and back into the patient.

11. Sensors Monitoring Reaction Chemistry

The photolytic artificial lung can include one or more sensors that monitor the different chemical reactions occurring within the photolytic cell. The sensors can be used to measure for potential toxins and toxin levels. Various sensors and sensor systems can be used including visual observations of color changes of redox indicator dyes or gas bubble formation, closed electrical current measurements and pH measurements, and dissolved oxygen probe analysis. Gas chromatography assays can also be performed. A dissolved oxygen probe can be used to test and monitor $O_2$ generation, as dissolved oxygen, in real time. Also, the photolytic artificial lung can incorporate one or more portals to insert a dissolved oxygen probe, $CO_2$ probe, pH monitor, etc. in different locations if necessary. The photolytic artificial lung can also incorporate separate sampling chambers to trap gas bubbles for testing. These sampling chambers could also incorporate a device, such as a septum for a hypodermic needle for instance, to obtain a sample for further testing. One skilled in the art would recognize numerous sensors could be used for monitoring the reaction chemistries occurring within the photolytic cell.

The photolytic artificial lung and photolytic cell can also include one or more process regulator devices that respond to the readings provided by the sensors. The process regulator devices increase or decrease the amount of dissolved oxygen or $CO_2$ output, lower toxin levels, etc., depending on the requirements of the patient or of the photolytic cell. It is within the purview of one utilizing the photolytic artificial lung to determine what process regulator devices are required.

All of the seals in the photolytic artificial lung are made of an inert material that properly seals blood flowing through the photolytic artificial lung from accidental contamination. The seals of the photolytic lung should also be formed of a material that does not interact with the blood. Preferably, the seals are formed of a silicone-based material.

Laminar flow is minimized within the photolytic artificial lung. Minimization of laminar flow is accomplished by using current commercial cells, such as electrodialysis, electrodeionization, etc. Commercially available cells accommodate electrodes, membranes, and thin liquid chambers with flow distributors, and provide good seals and corrosion resistance. The cells are available in lab scale units for process development work. A particularly preferred commercial cell is the FM01-LC device from ICI Chemicals and Polymers, Electrochemical Technology, Cheshire, UK.

Multiple Photolytic Cells

Preferably, the photolytic artificial lung uses a plurality of photolytic cells in a stacked formation. The plurality of photolytic cells receive blood flow from the venous circulation and are exposed to photo-activation via a directed laser light source. The stacking of a plurality of photolytic cells allows for a large overall surface area for blood to receive maximal exposure to dissolved oxygen. Also, stacking a plurality of photolytic cells allows the overall photolytic artificial lung to achieve a smaller size, thereby allowing the photolytic artificial lung to be miniturized.

Moreover, it has been found that one is able to control material properties of the photolytic surface, resulting in an expression of the maximal rate by which dissolved oxygen is increased (or carbon dioxide decreased) as a function of reaction surface area and laser power. If desired one can use the materials described herein to create a photolytic chamber, which incorporates optimal reaction kinetics and fluid mechanical modeling of blood flow in relation to the photolytic surface. The selected materials can be used in selecting the boundary conditions for the full chamber, emulating the fundamental relationship between the alveolar surface and the pulmonary capillary.

The Combinations of Materials and Reaction Interface Properties to Yield Target Photolytic Gas Exchange have been Established.

The overall goal of the work has been the establishment of Photolytically Driven Electro-Chemical (P-DEC) technology. This technology is based on the use of photolytic energy to provide "charge separation" in a thin film, and then the use of the resulting electrostatic energy to drive important chemical reactions. Currently photolytic energy is employed to drive the exchange of oxygen for carbon dioxide in blood, thus performing "alveolar" gas exchange. The viability of the concept of generating dissolved oxygen (DO) photolytically and concomitantly releasing $CO_2$ has been demonstrated. It was also demonstrated that significant electrical current could be tapped from the cell during the photolysis, and that active oxygen (AO) can be prepared and converted to DO. The general sequence of chemical reactions upon which the $O_2$—$CO_2$ exchange is set forth above. All of these reactions have been demonstrated in lab tests to date.

The data demonstrates feasibility of photolytically producing the liquid and gas phase oxygen, employing titanium dioxide as the critical material to carry out photo-transduction. This invention allows one to 1) to develop performance selections and combinations of the photolytic thin film materials, and 2) to identify the interfacial construction chemistries needed which allow the following three conversions to occur efficiently: hv→AO, AO→DO, and e-→conductor. In addition, the longer the film interface remains intact the longer the performance life of the PAL unit. Hence film adhesion robustness is also important. Therefore the primary selection criteria for development of these materials and interfacial fabrication techniques are: 1) DO production rates reported as a flux (FDOflux, as $\mu L\ O_2$ (STP)/cm$^2$ of surface area), 2) Quantum yields ($\Phi$, reported in terms of the electrical current produced, and the amount of AO or DO produced), and 3) the length of time such DO and $\Phi$ values are retained.

The results obtained from the invention allow one to minimize photolytic lung device size, energy requirements, weight, and heat production.

The invention provides a means:

1. To develop film-forming materials and film interface chemistries for PAL device fabrication that have the desired combination of properties to efficiently absorb photolytic energy (highest Φ values for absorption).
2. To fabricate these materials in a manner to efficiently use the photolytic energy to generate DO, or, in the case where AO is the primary product, to efficiently convert AO into DO in the aqueous medium.
3. To conduct the free electrons efficiently to a current collector.
4. To identify a suitable material for the current collector.

The important parameters that control performance are the production rates of DO, $CO_2$ gas, and electrical current as a function of photon energy and photon flux per unit area of reactive surface, i.e. that area exposed at the electrolyte (i.e. blood) photolytic coating interface. These production rate parameters, are key to selecting the composition and fabrication methods for constructing photolytic films for blood gas control technology.

Photoactive film systems of the invention were prepared from various materials that combine high efficiency for photon absorption with the required physical properties, such as electrical conductivity, mechanical strength, catalytic activity for DO production, functional lifetime, and adhesion to substrate. Suitable materials which meet the needed performance criteria are any solid form of the following nanoparticles (high surface areas) of $TiO_2$(anatase), ZnS, ZnO, $ZrO_2$ (cubic, stabilized with Y), $Fe_2O_3$, $WO_3$, $V_2O_5$, $SnO_2$, $Cr_2O_3$, $MoO_3$, $MnO_2$, and the like, and combinations thereof. These materials may be crystalline, mesoporous, microporous, amorphous, hydrated, nanoparticulate, single crystal, and combinations thereof. Potential dopants that may be used to vary the light absorption range or increase the light gathering efficiency ("sensitizers") include traces of Cr, V, Rh, Ru, Pt, Ir, Pd and Ni. These dopants can be further enhanced by the use of chelating complexes of these metal ions. Particularly effective charge separation can be achieved when the chelating agent for the sensitizing moiety contains chemical groups that facilitate electronic conduction, for example the use of carboxylate group on the aromatic rings of a chelating agent of a noble metal. For example, dicarboxylate derivatives of 1,10-orthophenanthroline used as a ruthenium(II) complex bound to the surface of metal oxides, especially $TiO_2$ (anatase). Other candidates for such electronic conducting groups are phosphates, phosphonates, phosphinics, sulfonates, etc. Other aromatic groups are dipyridine, 2-hydroxy-pyridine N-oxide, etc. based compounds with denticities of 2-7.

To cover both the UV and visible power options, light sources can be used which emit in the 350-600 nm range, the exact wavelength being determined by the film material being tested.

Use of Mesoporous Materials to Produce Artificial Pulmonary Capillaries

As mentioned above, mesoporous materials can be utilized to produce, among other structures, artificial pulmonary capillaries. Examples of devices containing such artificial pulmonary capillaries are set forth in FIGS. 14-16.

Figure 14:
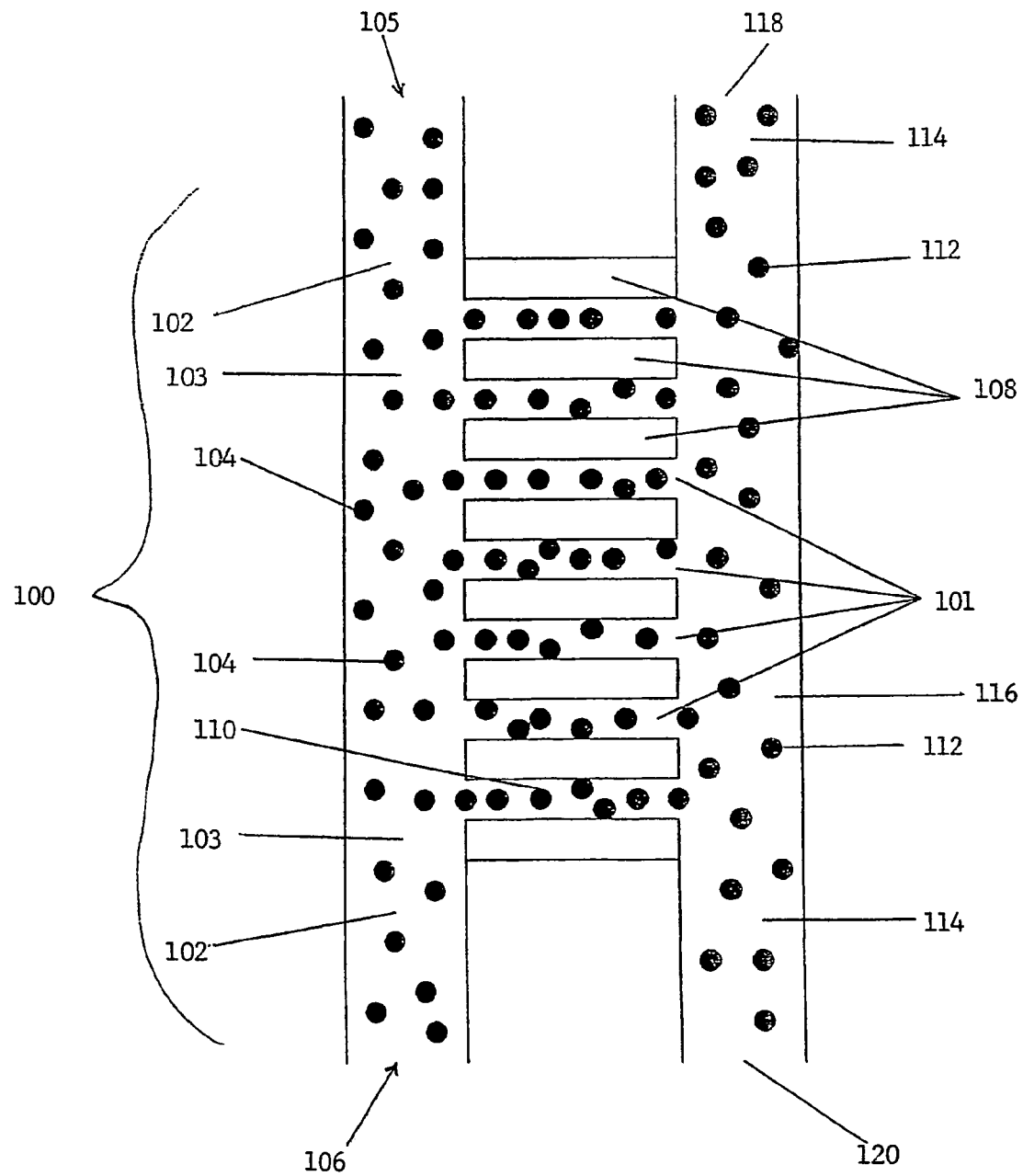
FIG. 14 illustrates a device containing microfabricated, artificial pulmonary capillaries.

In this regard, in FIG. 14, a device 100 containing microfabricated capillaries 101 is shown. In the device 100, venous blood 102 comprising blood serum plasma 103 and deoxygenated red blood cells 104 is obtained from a patient (not shown) through one or more venous blood inlets 105 and 106. As the deoxygenated red blood cells 104 pass by the lighted paths 108, the blood cells become partially 110 to fully oxygenated 112. The oxygenated blood 114, comprising blood serum plasma 116 and oxygenated red blood cells 112, is then returned to the patient by means of one or more arterial blood outlets 118 and 120.

The artificial pulmonary capillaries 101 are channels or pores which can be made from various compositions such as mesoporous materials. The width of the channels can vary so long as the internal diameters are larger than the size of the red blood cells. Preferably, a width of 10-100µ is desirable. The length of the capillary channels/pores can also vary depending on various characteristics such as gas generation rate, etc. A length of 50-500µ is currently contemplated.

The lining of the light paths 108 and/or capillaries 101 is coated with and/or constructed out of materials comprising, preferably, a transparent surface material, an optional conductive coating material such as titanium (Ti) metal, an adherent light absorbent material such as the photolytic catalyst $TiO_2$ (anatase) and a disproportionation catalyst such as $MnO_2$, applied (preferably) or constructed as a laminant. Long wavelength (low energy, i.e. about 350-390 nm) U.V. laser light is then applied to the light paths. The U.V. light is absorbed into the $TiO_2$ layer, resulting (through photoactivation) in the conversion of water to $H_2O_2$, an active form of oxygen (AO) along with the liberation of hydrogen ions and free electrons. The active oxygen is then converted, during disproportionation, by the catalytic action of $MnO_2$, to dissolved (or aqueous) phase oxygen and water. The dissolved oxygen diffuses from the laminant surface to oxygenate hemoglobin present in the blood (i.e. the iron-containing pigment of the red blood cells). The free hydrogen ions combine with carbonate and bicarbonate ions during protonation to yield carbonic acid. The carbonic acid is then rapidly converted by carbonic anhydrase present in the blood to water and carbon dioxide. The carbon dioxide by-product is subsequently then removed from the system such as by venting to the trachea, etc. Moreover, the free electrons generated are conducted away to avoid reversal of the reaction such as by the application of an electron drain, etc.

Figure 15:
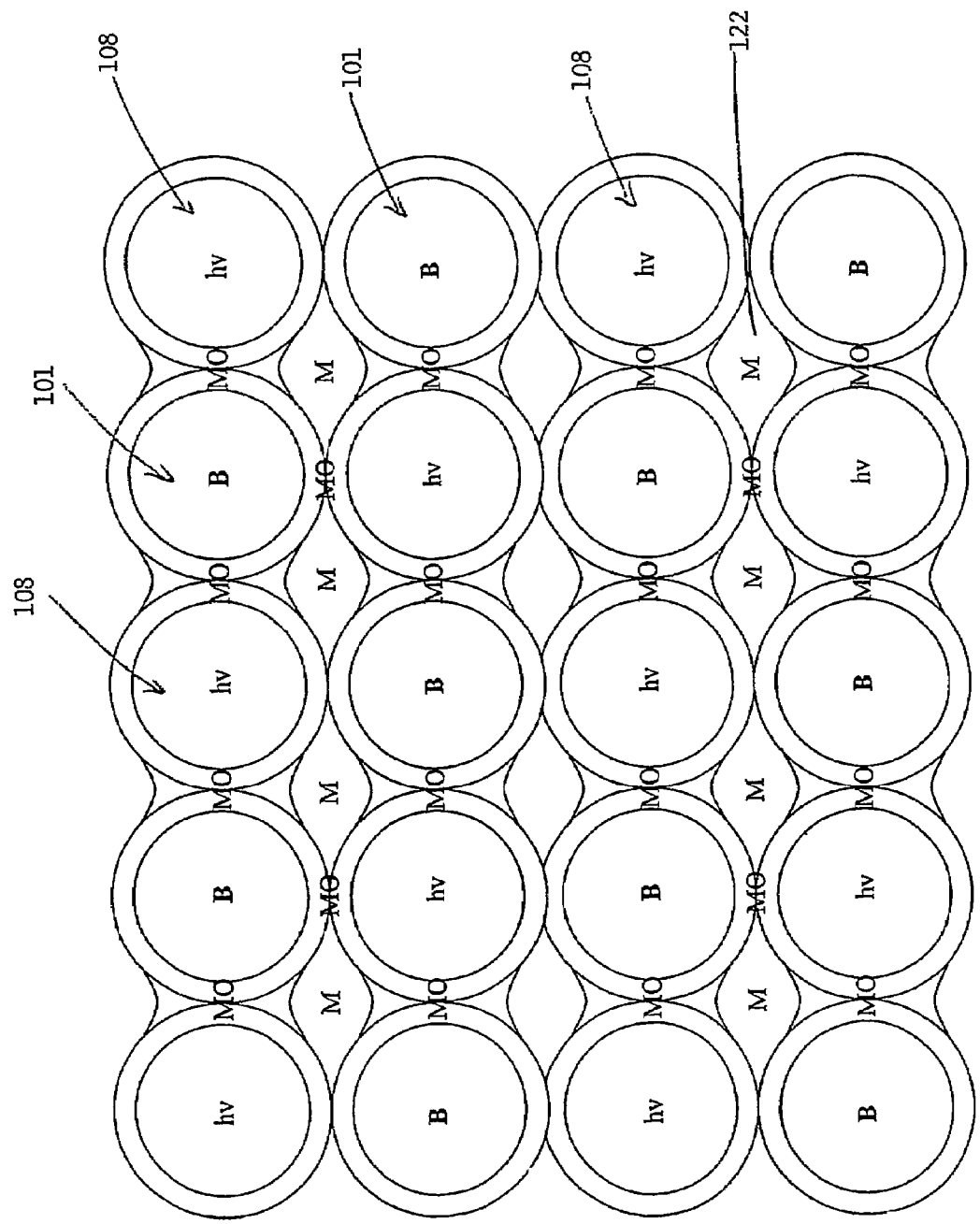
FIG. 15 shows an alternative embodiment of the device illustrated in FIG. 14.
Figure 17:
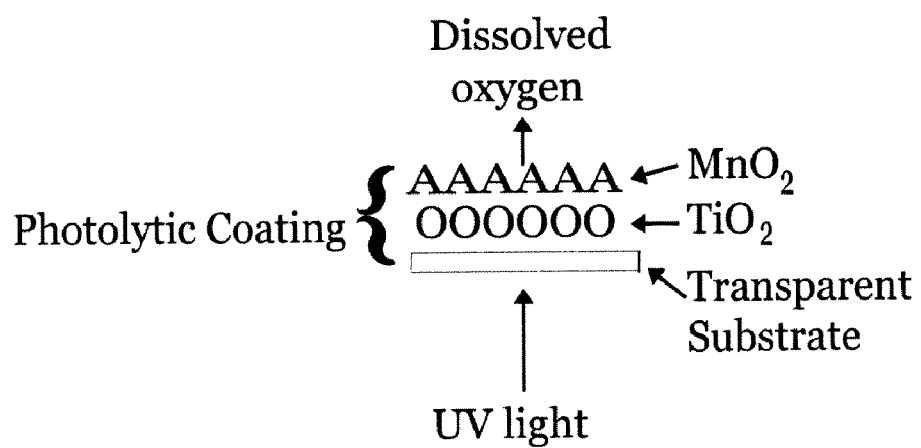
FIG. 17 shows the design for the photo-reactive (photolytic) surface of the photolytic cell of the present invention.

FIG. 15 is directed to an alternative device containing artificial pulmonary capillaries. In this device, the light paths (hv) 108 run parallel with the artificial blood capillaries (B) 101. The light paths 108 and the blood capillaries 101 are separated by an interphase comprising, preferably, a light transparent substrate material, an optional conducted coating of metal (m) such as titanium (Ti) metal, adherent $TiO_2$ (anatase) and a metal oxide such as $MnO_2$, applied or constructed, preferably as a laminant. The blood diffuses into the porous metal oxide and the water therein is converted to dissolved oxygen by the process discussed above. In this embodiment, an electrical conductor such as a conducting Metal 122 is also provided for removing the electrons.

Additionally, FIG. 16 presents an arrangement or pattern of materials for the construction of a similar artificial pulmonary device. In FIG. 16, the light fiber or pipes are labeled "hv" (UV/via light); the blood channels are labeled "B" the metal oxide is labeled "MO"; and the electrical conductor is lableled "M." The above referenced artificial pulmonary capillaries are useful for producing dissolved oxygen from water in blood.

Liquid Media Results

Figure 10:
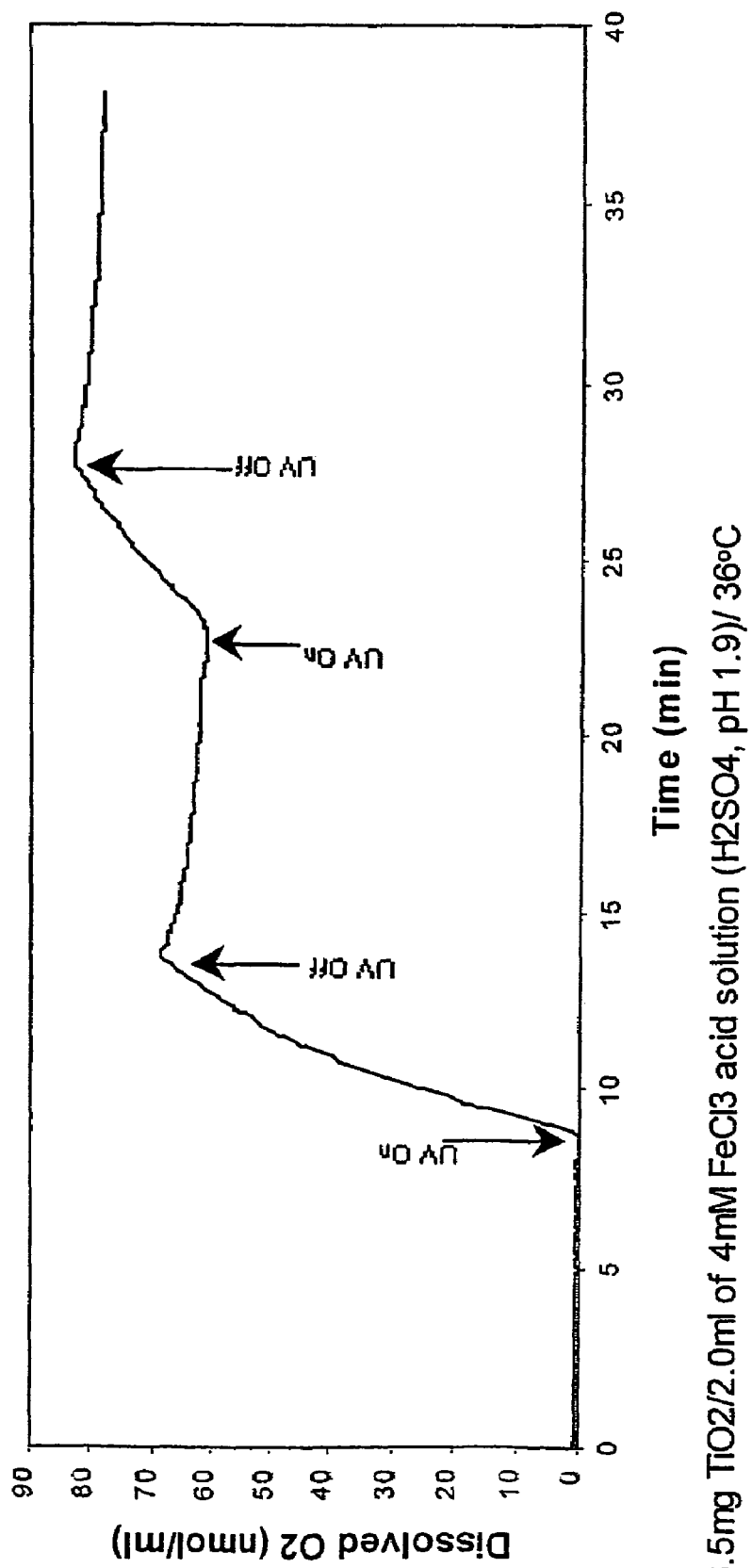
FIG. 10 is a graph is dissolved oxygen concentration (vertical scale) versus time (horizontal scale) for the $TiO_2$ in acidic medium.

Dissolved Oxygen has been produced in acidic, basic, and neutral media. FIG. 10 illustrates dissolved oxygen production in a sulfuric acid solution (pH=1.9). A slurry of titanium dioxide, when illuminated with ultraviolet radiation ($\lambda$=365 nm), produces electron-hole pairs. By using ferric chloride as an electron acceptor, charge separation of the electron-hole pairs is accomplished. This crucial step allows the hole to react with water molecules, producing oxygen and hydrogen. As can be seen in FIG. 10, oxygen concentration increased only when the system was illuminated, thus indicating that the observed oxygen production was a result of the photocatalyst.

Figure 11:
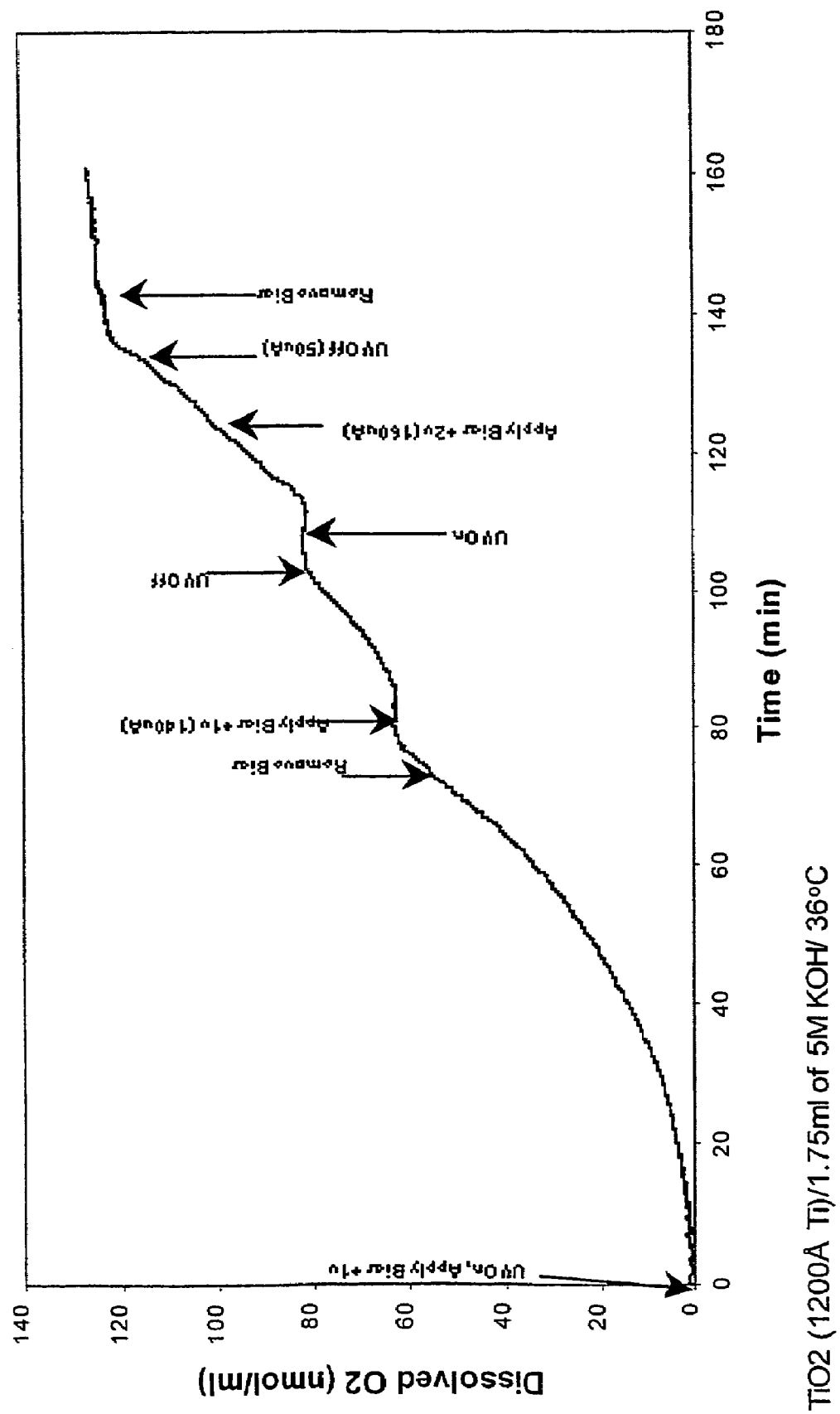
FIG. 11 is a graph of dissolved oxygen concentration (vertical scale) versus time (horizontal scale) for the $TiO_2$ in basic medium.

FIG. 11 illustrates dissolved oxygen production in a potassium hydroxide solution (pH~14). Here, charge separation is accomplished by using a current collector and an external bias voltage; a titanium layer on the substrate is used as the anode while a platinum wire is used as the cathode. The photoactive layer, $TiO_2$, is coated onto the titanium anode and supplies the required holes for water splitting. The oxygen concentration increases only when the photoactive layer is illuminated and a bias voltage is applied. When either element, the UV radiation or the bias voltage, is removed, the oxygen production ceases.

Figure 12:
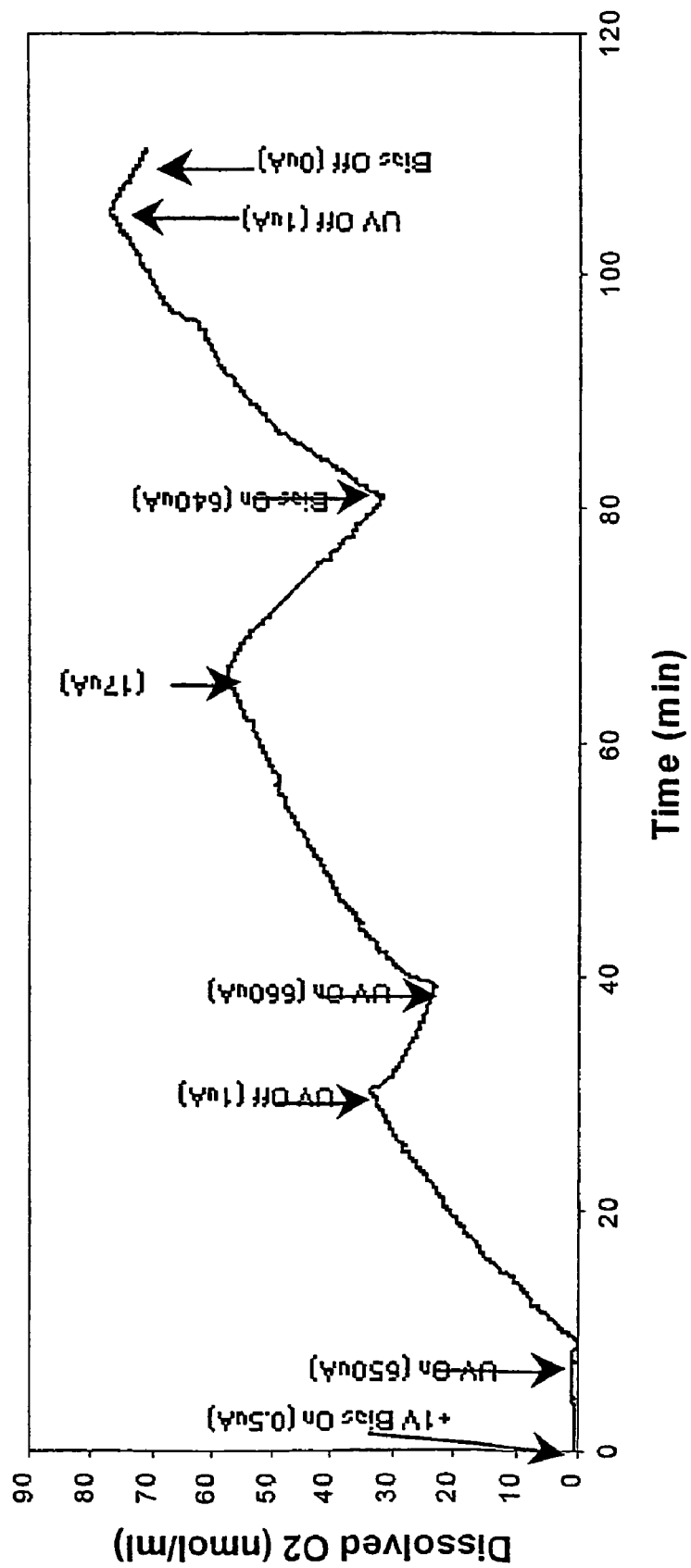
FIG. 12 is a graph of dissolved oxygen concentration (vertical scale) versus time (horizontal scale) for the $TiO_2/Ti$ system in Lockes Ringer Solution.
Figure 13:
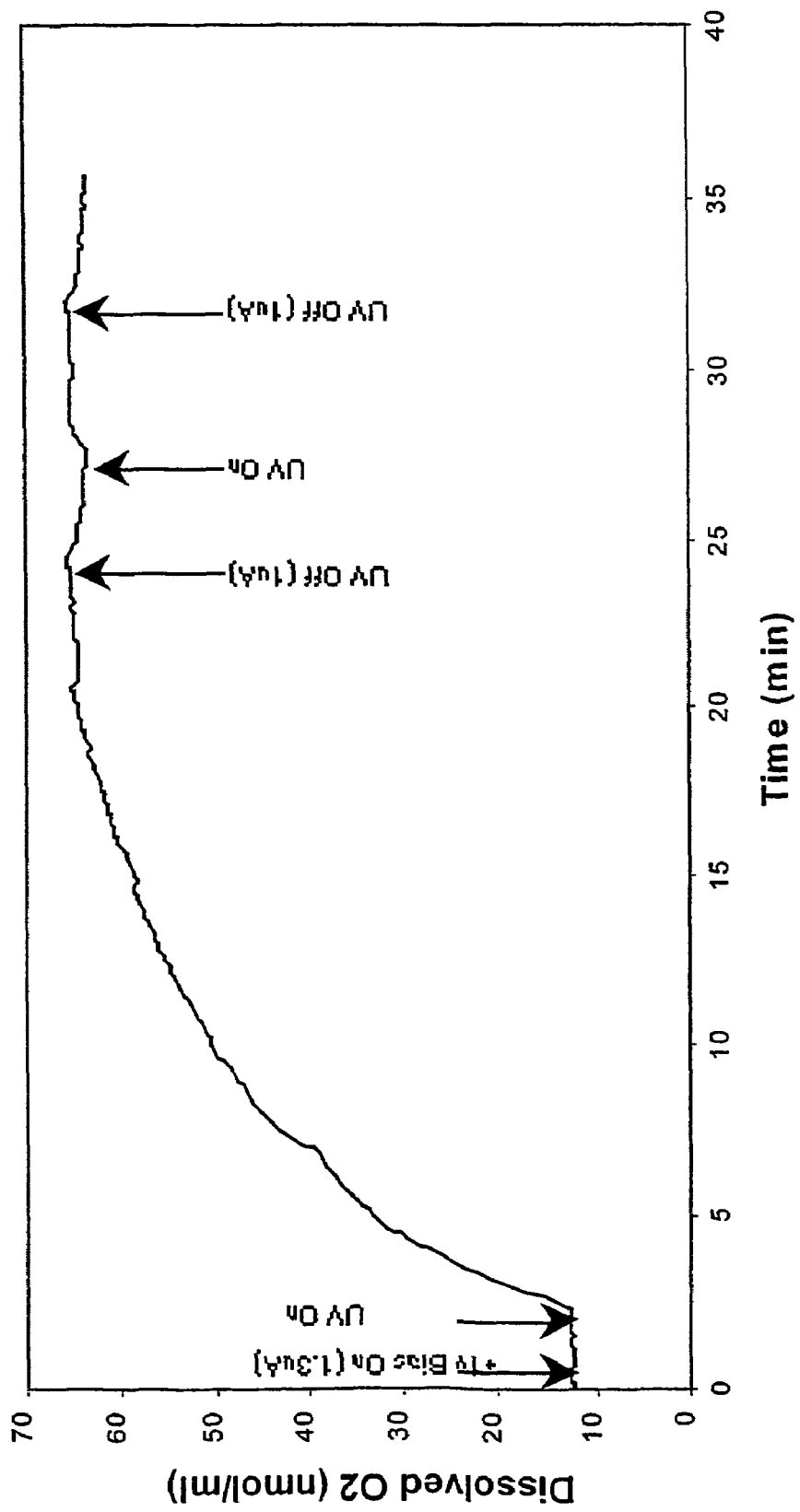
FIG. 13 is a graph is dissolved oxygen concentration (vertical scale) versus time (horizontal scale) for the $TiO_2/ITO$ system in Lockes Ringer Solution.

Production of dissolved oxygen was also demonstrated in a blood substitute known as Lockes Ringer solution (pH=7.2). The system again used an external bias voltage to achieve charge separation and $TiO_2$ on titanium as the photoactive layer. As can be seen in FIG. 12, oxygen production occurred only when both UV radiation and a bias voltage was present. FIG. 13 illustrates another system using Lockes Ringer. Here, the photoactive layer, $TiO_2$, was coated on a transparent, conducting film (indium tin oxide, or ITO). This allows the UV radiation to be directed through the substrate rather than through the liquid media. Again, both a bias voltage and the UV radiation are required to achieve dissolved oxygen production.

DO Production Efficiency:

In order to efficiently use the photolytic energy to generate DO (highest Φ values for production of electrons (electrical current in $\mu A/cm^2$ of photolytic surface), and AO (measured in oxidizing power, for example depletion of methylene blue concentration per unit time, e.g. $\mu M/min/cm^2$ of active surface)), charge recombination will be prevented through the use of bias voltage.

Another technique involves thin layer (e.g. 0.1-50 μm) microcrystalline film structures fabricated such that the conductance bands of the crystallites overlap (measured by film resistivity). Such alignment is possible using spin coating, sol-gel processing, sputter coating, chemical vapor deposition (CVD) coating, controlled oxidation (e.g. anodizing) of metallic surfaces, co-fabrication of conductive particulates or fibers, etc. Such constructs can be visualized and analyzed using scanning electron microscopy (SEM), EDS, and other surface techniques.

Using micro fabrication, large surface areas are possible for the DO reaction surface. For 10 micron channels for the red blood cells, and 10 micron thicknesses for the photolytically sensitive material, projects 133,000 $cm^2$ of active surface area would be contained in a cube device 10 cm on a side. Hence, microfabrication is a highly attractive means to use to deploy the PAL technology since it results in small (ambulatory) devices, allowing the patent a wide range of freedom of motion.

Tests have shown that DO generation can be a multi-step process, involving an intermediate, or "active" form of oxygen. Therefore, with certain materials, two laminated films are needed to produce DO (one for active oxygen (AO) formation, and one for AO→DO conversion.). For example it has been shown that anatase titania coatings generate highly reactive AO (e.g. hydroxyl free radical) and so requires AO→DO conversion in this case. Other coatings, such as zinc oxide (ZnO), produce AO in the form of $H_2O_2$, which is readily and quickly converted to DO in a second film of $MnO_2$. Some materials, such as Ru-doped tungstate, release $O_2$ directly. It is our intention to evaluate the benefits and problems associated with each of these potential sources of DO. The production efficiency can be reported in terms of DO generation and Φ. It's possible that the AO is generated near the irradiated surface, and then, by semi-conduction or diffusion, transfer this oxidizing power to the opposite side where it is then converted to a DO intermediate (e.g. $H_2O_2$) or directly to DO.

While not wishing to be bound by theory, it appears that, the water from the blood supplies the oxygen, which ultimately becomes DO. The extremely high concentration of water adjacent to the DO-emitting surface, about 55.5 M, is so high that availability of $H_2O$ for reaction should never be rate limiting. Note that $H_2O$ is also a very small molecule, so that its diffusivity is high, even in small pores, especially given the driving force of the high concentration. Likewise, H+ ions readily "hop" through water and so always have high apparent diffusion rates. Therefore only the diffusion of DO needs to be accommodated. Since the DO is already dissolved in the blood, the diffusion limitation has already been accommodated in the PAL design concept.

Photo-Electron Removal:

To conduct the free electrons efficiently to a current collector (i.e. the photo-active layer needs to be electrically conducting, i.e. at least semiconducting), a bias voltage has been added at the initiation of illumination, or maintained during illumination, to increase charge separation yield by providing an electric field within the film to cause immediate electron flow away from the photon absorption point. In this case, the bias voltage is kept low to prevent direct electrolysis of water at the electrode surfaces or to promote any other electrochemical reactions. The bias voltage selected needs to be just barely sufficient to extract the free electrons to prevent charge recombination.

The efficiency of the electron removal may be further enhanced by doping the semiconductor and creating highly conducting metal clusters within the semiconductor coating. This will facilitate electron mobility and allow better charge transfer to the external circuit.

Current Collector Material Development

Suitable current collector material is typically durable, transparent in the desired wavelength range, and highly conductive. This material can be selected based on extended irradiation tests under applied and/or generated voltage to insure the necessary durability. Possible candidates include thin (~50-100 Å) metal films that are sufficiently transparent in the wavelength range chosen for the active coating, yet conductive enough to allow current flow. These thin films (composed of Ti, Ni, Cu, or Pt) may be deposited on the substrates using CVD or e- beam evaporation. Another promising material is the transparent, conducting, indium tin oxide (ITO). This material may be deposited on a substrate at a thickness of ~1500 Å to give an effective current collector that is transparent in the desired wavelength range. These materials were evaluated based on their ability to transmit in the target wavelength range, efficiently conduct electrons from the active layer, and lifetime.

Test Apparati and Methods:

The screening procedures to assess coatings use techniques similar to those used in the preliminary tests. The relatively small size of the Hansatech gas and liquid batch cell photosynthesis apparatus is particularly useful in studying the technology since they accommodate a broad range of chemical coatings techniques, such as chemical vapor deposition, vacuum sputter coating, sol gel techniques such as dipping and spin coating, drying, and curing techniques, such as controlled atmosphere ovens and high temperature furnaces. This apparatus minimizes internal cell resistance (low flow cell electrical resistance facilitates removal of electrons from the photoactive layer). In addition, this apparatus provides the controlled and closed spacing anticipated for the ultimate commercial device. In screening the new photoactive coatings, we will use direct measurements for dissolved oxygen (DO). A DO probe can be included into the loop for the direct measurement of DO. This direct approach of measuring oxygen provides real time data on the rate of DO production, DO performance over time, and is more sensitive than the volumetric gas sampling method.

Some scaled up tests can employ the photolytic flow-through cell used in the preliminary work, which consists of a laser light source, two peristaltic pumps, reservoirs, meters, and sensors and sample ports for DO/pH/T/Icell/blood gas parameters for in-line or real-time measurements. Where whole blood is used, the entire suite of blood gas analyses can be performed.

Surface spectroscopic techniques can be used to characterize the photolytic coatings during and after preparation, and then after use. Such techniques include optical and scanning electron microscopy (OM and SEM respectively) for imaging, and electron dispersion spectroscopy (EDS) for elemental composition analysis in thin films. These techniques provide quantitative and/or qualitative measurements of coating adhesion, porosity, inter-layer bonding, thickness, densification, uniformity, and friability.

Dyes can be used in certain tests. Methyl viologen can be used to indicate the photochemical generation of electrons, and methylene blue to selectively indicate the production of highly active forms of oxygen (AO), other than just $O_2$. Hence the disappearance rate of MB is a measure of the quantum yield with respect to AO, while the DO production rate, as measured either by a DO probe or by blood gas analysis, indicates the quantum yield with respect to DO production.

Several calibrations may be necessary to determine quantum yields. Quantum yields are needed for anodic electric current production (Icell), DO production, and acid production changes (the latter determined from pH on-line, or TIC in grab samples (TIC=total inorganic carbon, i.e. sum of the concentrations of all carbonate species). To calculate quantum yield, the photon flux at the interface between the photosensitive/DO generating surface and the electrolyte, $\Phi$, has been determined using conventional actinometry techniques with standard ferrioxalate solution in the cell. The ferrioxalate concentration in the feed and treated fluid is determined in the conventional manner, using UV/Visible spectroscopy. The power level and beam intensity of the source laser can be calibrated using a standard photon counter in place of the flow cell. The thickness of sputter coated metal films can be measured using a % light attenuation calibration curve. These films are <100 nm thick and are about 50% transparent at the UV wavelength being used in the DO generation tests.

Microfabrication of Multilayer Constructs

These constructs will be assembled into photolytically powered cells through which blood is passed, and so will be assembled in geometries based on biological fluid modeling designs, which minimize blood degradation and are biocompatible. The materials selection in this task will include affixing the thin films onto optically transparent surfaces so the coatings can be photolytically energized. Incorporation of the optical features into the cell construct will follow a parallel pattern of computer modeling followed by experimental evaluation and validation.

Development of a Computational Model Relating Blood Flow to the Dispersion of Dissolved Oxygen Particles Resulting from Photochemical Activation.

Using computational fluid dynamic (CFD) techniques, a model can be developed to simulate the flow across a single surface of variable geometry. Information regarding the photolytic process and the shear limitations of red blood cells will be incorporated in the model's boundary conditions. Depending on the findings from the flow simulation studies, modifications of the shape and size of the surface reactive cells will be done. Since the photolytic reactions occur at the surface, the surface to volume ratio must be large enough to allow for sufficient oxygenation of the blood volume. At the same time, the shape and size of the flow chambers must be large enough to allow for mixing. The final design will provide a high yield photolytic surface, incorporating optimal reaction kinetics and optimal boundary conditions, in effect, emulating the interface between the alveolar surface and the pulmonary capillary membrane. In effect, this process emulates closely the natural properties and configuration of the pulmonary capillary and the alveolar membrane. In the physiological setting, un-oxygenated pulmonary blood passes through the capillary system, with closely regulated exposure to the process of $O_2$—$CO_2$ exchange. Similarly, our system will create a flow chamber, which will be juxtaposed adjacent to a source of photolytically driven gas exchange. The purpose of this model will be to determine the optimum geometric and mechanical constraints, which define this flow chamber.

Flow modeling is performed using a commercial CFD software package obtained from CFD Research Corporation (Huntsville, Ala.). The flow domains can be discretized into finite elements, and the equations for conservation of mass, momentum, and the convection-diffusion transport of dissolved oxygen can be integrated using finite element analysis techniques. The computational model provides a robust tool to study how different flow and geometrical configurations can affect the yield of dissolved oxygen in the flowing blood within the constraints exerted by the photolytic processes and the control system. This model can be used to optimize the flow characteristics and the size and shape of individual surface reaction cells, as well as the configuration of the arrayed cells, such that a balance is achieved between photolytic yield and the dissolved oxygen recovery. Different geometrical and flow configurations can be tested in accordance with the rate of DO production at the boundaries. CFDRC software can be employed to create the CAD model of the geometries, and to discretize them into unstructured tetrahedral finite elements. The Navier-Stokes equations can be integrated over the finite element space to solve for the detailed flow field over the entire domain of the model. Once the flow field is known, it can be used to solve the passive convection-diffusion equation for mass transport of dissolved oxygen. The governing partial differential equation for mass transport in the blood, excluding the facilitated transport due to hemoglobin binding, is as follows:

$$\frac{\partial P}{\partial t} + V \cdot \nabla P = D \nabla^2 P + f$$

Here, P(x,y,z,t) is oxygen partial pressure, D is the diffusion coefficient for oxygen. V(x,y,z,t) is the velocity field, and f allows for imposing a sink/source term for oxygen. Facilitated transport can be taken into account by replacing D with an effective diffusion coefficient. Here, we treat the production of dissolved oxygen at the boundaries of the model through proper boundary condition imposition. The diffusion coefficient of dissolved oxygen is very small (~10-9 m$^2$/s), and this usually leads to a convection-dominated transport, even at small Reynolds numbers. The convection-dominated problems are characterized by thin mass transfer boundary layers, and hence their computational analysis requires special care and treatment in order to prevent convergence problems from numerical stabilities.

The present inventors propose to use a finite element method developed in house to evaluate the distribution of DO over the model domain. In this technique, a high order operator splitting method is used to split the convection-diffusion equation into a parabolic diffusion equation and a hyperbolic convection equation. The diffusion equation is treated using the standard Galerkin scheme, while the convection equation is solved in the Lagrangian framework along the characteristic lines. The algorithm uses tracking of the Gaussian quadrature points to project the numerical information from one time step to the next. This technique exhibits good conservation and phase characteristics, and allows for large time steps, and therefore efficient integration of the convection-diffusion equation towards steady state. This algorithm has been extensively validated against benchmark problems and has been successfully applied to convection-dominated mass transfer problems in blood flow, whose transport characteristic are of similar nature to the present problem. Having solved for the flow field and DO concentration patterns over the entire domain of the model, the flow and geometrical input configurations can be modified to reach an optimized balance between flow, photochemical yield, and distribution of dissolved oxygen. This approach is illustrated by the examples shown below:

In the first example, a simplified setting was chosen, that consists of several cylindrical units (of diameter $d_u$) each having a single photolytic tube (of diameter $d_T$) at its center. It is assumed that the mass transfer coefficient between the photolytic surface and blood is K, W/m$^2$K, the diffusion coefficient of oxygen in the blood is D, and the target for the total capacity of blood oxygenation (taking into account the target volume flow rate V, and the oxygen solubility of blood S, including hemoglobin binding) is Q, W, and, hence the required surface area of photolytic contacts, $A_{tot}$, is known. Thus, the number of units needed for the transport is $A_{tot}/A_0$, where $A_0=\pi d_T L$ is the contact surface area of a single tube of length L. The units can be stacked in parallel and series configurations, which determine the flow velocity and hence mass transport coefficients thereof. For example, if the number of parallel units is N, the average velocity of flow can be obtained from the conservation of mass, u=V/(N S), where S is the cross-sectional area of the flow in the unit. The question will then be: Which stacking configuration, and hence flow velocity, would be the most favorable? It is known that the mass transport coefficients for flow through ducts increase with increasing flow velocity u, and with the diffusion coefficient, density, and solubility of the medium fluid, while they decrease with increasing the viscosity of the fluid, and with the length L and diameter $d_u$ of the cylindrical unit. The exact relationships can be determined, based on the turbulent/laminar regime of flow and the solubility and diffusivity of the fluid as well as the rate of oxygen production. Once the physical properties, i.e. the mass transfer coefficient, the fluid's density and oxygen solubility, fluid's viscosity, and the rate of oxygen production, and the dimensions of the mass transport unit, i.e. the length and diameter of the unit and the photolytic tube, are fixed, the choice of the highest possible flow velocity u will yield the smallest mass transport area, leading to a more compact overall system. High velocity cannot however be obtained without cost, as the pumping power $W_{pump}$ for a given flow rate and density is proportional to the pressure drop across all the units, $W_{pump}$=V $\Delta$P. But the pressure drop is $\Delta P=\mu p u^2$ nL/(2$d_u$), where nL is the total length of all units in series. Thus, the cost of operation will increase quadratically with flow velocity.

In the second example, a configuration was chosen where the flow rate and pressure drop are fixed, i.e. the properties of the pump are known. This design consists of compartments that cover the whole flow cross-section. At a given flow rate and pressure drop, one can achieve the required total flow cross-section area S by employing a few large, or many small, compartments. The question addressed here is whether there is an optimum compartment size $d_n$, and hence, a rationale for the optimum number of compartments? The required number of transport units can be determined based on flow and mass transfer characteristics as $N_{req}=A_{tot}$/S Nu/Pe. Here, Nu is Nusselt number and Pe is the Peclet number (Pe=Sc Re, where Sc and Re are Schmidt and Reynolds numbers, respectively). From this, the ratio of length to diameter of the compartments has to satisfy the relationship $L/d_n=N_{req}$Pe/(4 Nu). In turbulent flows, the Nusselt number has a weak dependence on $L/d_n$ meaning that once the mass transport yield is determined, the ratio of length to diameter is nearly fixed at constant Schmidt numbers and throughputs. In other words, a compartment of edge size 100 mm and length 10 m does not provide more mass transfer than a compartment of edge size 10 mm and length 1 m, at the same throughput, even though it has a 100-fold larger transport area. The pressure drop, however, would be four orders of magnitude higher in the smaller compartment. It is also possible to realize any $N_{req}$ with the laminar flow; knowing $N_{req}$ specifies Pe $d_n$/L. This will yield a constraint on nL, nL=$C_M$ where $C_M$ is a constant determined by the flow and mass transport characteristics, namely flow rate, physical properties, rate of oxygen production yield at the photolytic surface, and the mass transfer Nusselt number. On the other hand, the pressure drop, and hence the pumping power, remains constant (according to Poiseuille law) if the following ratio is constant: $L/nd_n^4$=constant=$C_F$, where $C_F$ is a constant depending on flow characteristics and dimensions of the compartments. We can combine these two constraints by fixing the ratio $L/d^2_n$= $(C_M/C_F)^{1/2}$. Since the total flow cross-section is fixed, n $d^2_n$= $(C_M/C_F)^{1/2}$ is constant, which leads to constant flow velocity. Hence, the transport surface area $A_{tot}=n\pi d_n L$ can be determined as a function of the number of compartments: $A_{tot}=(C_M^{5/4}C_F^{-1/4})n^{-1/2}$. Thus, the surface area of a compartmentalized transport system can be reduced in a manner, which is inversely proportional to the square root of the number of compartments, given the same flow and transport characteristics. Accordingly, the pumping power can be kept low if the total flow cross-section S is chosen sufficiently large. As shown above, the transport area can be made smaller if more (but smaller) compartments are configured in the same cross-section ($A_{tot} \propto n^{-1/2}$, $d \propto n^{-1/2}$, $L \propto n^{-1}$).

Using the fundamental chemistry established in the examples above, a model system can be developed to specifically relate gas exchange with blood flow. Considerations in design can include optimizing the balance between photochemical output per unit area, photolytic cell surface area, the geometric and mechanical constraints related to the flow chamber, and the rate and turbulence of blood flow in order to maximize the yield of dissolved gases in flowing blood. The goals of this specific aim therefore include the modeling and testing of flow characteristics in order to maximize the recovery of dissolved oxygen derived from a photolytic surface. The ultimate goal of this process is to achieve an understanding, at a microscopic scale, of the relationship between the flow chamber and photolytically-driven gas exchange, a relationship which bears physiological analogy to that existing between the alveolar membrane and the pulmonary capillary.

Photolytic Cell Has Broader Applications

The photolytic cell as described may be used for photochemical processes beyond the preferred embodiments described above. The photolytic cell may be used in other organs to cause or regulate chemical reactions occurring within the system. The photolytic cell may be used in organs including, but not limited to, heart, lungs, brain, kidney, liver, etc. Alternatively, the photolytic cell may be used outside of a biological system in order to control reactive activity. Also, one having ordinary skill in the art would recognize that the photolytic cell could also be used as a potential energy source due to the production of electrons.

EXAMPLES

Having generally described the invention, the following examples are included for purposes of illustration so that the invention may be more readily understood and are in no way intended to limit the scope of the invention unless otherwise specifically indicated.

Example 1

A prototype photolytic artificial lung was produced in order to demonstrate the ability of the device and accompanying processes to re-oxygenate synthetic blood serum (Locke's Ringer Solution), with concomitant $CO_2$ removal and pH control, using thin film constructs. In this regard, a photolytic test flow cell (see FIG. 3) was constructed using exemplar materials for the elements of the photolytic artificial lung—a conductive coating of vacuum deposited Ti metal, a coating of adherent $TiO_2$ (anatase), a $MnO_2$ particulate layer, and then a bicarbonate solution. A U.V. laser light was introduced to the transparent glass or quartz substrate. This cell was used to collect pH and cell electrical current data as a function of laser U.V. irradiation. The details of the construction of such a prototype and the results produced thereby are discussed below.

In this regard, a photolytic test flow cell as shown in FIG. 3 of the photolytic artificial lung was prepared. Specifically, among other components the following layers of the photolytic cell were assembled: light source 20; transparent window 30; e⁻ conductor (anode) 36; $TiO_2$ photo catalyst 32; $MnO_2$ catalyst 34; NAFION® cation exchange membrane 46; catholyte 48; and conductor (cathode) 38. The particular parameters of these components and others are as follows:

Glass/Quartz Slide 30 Preparation

A glass slide was degreased by swirling in toluene or MEK The slide was flash dried in air for less than about 1 minute. The slide was then soaked in warm Micro® cleaning solution for about 2 minutes. The slide was rinsed thoroughly with 18MΩ Dl water. The slide was immediately thereafter soaked in a water bath for about 2 minutes. The slide was rinsed thoroughly with water from a squirt bottle and drained but not allowed to dry. With caution, the slide was submerged in a solution of concentrated sulfuric acid and was allowed to stand for 2 minutes. A plastic hemostat was used to hold the slide when it is inserted/withdrawn from the sulfuric acid. The slide was withdrawn, allowed to drain, and rinsed thoroughly with water. The slide was then soaked in a water bath for about 2 minutes. A water break test was then performed on the slide. Using a plastic (Nalgene®) beaker with cover watch glass, the slide was dipped for 2 minutes in a solution of 0.1% HF and 1N HCl. The surface of the glass now contained Si—OH linking groups. These slides were kept wet, and stored in 5% $HNO_3$.

Catalyst Layer 32 Preparation

About 1.0 g of $TiO_2$ (anatase) was added to a plastic (Nalgene®) beaker with a cover watch glass, and a magnetic stir bar. In a hood, 80 mL of 0.1% HF and 1N HCl was added to the $TiO_2$. A stirrer stirred the beaker until the solids were well suspended. The beaker was mixed for 60 seconds and was proceeded immediately to the next step of dividing the slurry between two 50 mL capped centrifuge tubes. The tubes were centrifuged for at least 5-10 minutes. The supernatant was discarded. Each tube was rinsed 3 times with 40 mL portions of water. The tube was capped, vortexed thoroughly, centrifuged, decanted, and the steps were repeated. Each tube was rinsed 3 times with 40 mL portions of isopropanol (iPrOH). Optionally, one or more inorganic silane and/or titanate-coupling agents can be added to the last alcohol rinse to facilitate agglomeration and adhesion in the final coating. The aggressive oxidizing environment of the UV/$TiO_2$ during use may rapidly degrade organic-based coupling agents and so inorganic couplings may be favored.

Application of the Catalyst to the Glass Slide

The pretreated $TiO_2$ anatase particles were magnetically re-suspended from one of the tubes in a jar containing isopropanol sufficiently deep to cover the glass microscope slide. Magnetic stirring was initiated to keep the particles suspended. The amount of particles used is an adjustable parameter in determining the thickness of the final coating produced.

A sufficient amount of $Ti(iOPr)_4$ (TTIP) was added to yield a 0.2 vol % solution (e.g., by adding 160 uL TTIP per 80.0 mL isopropanol). Using a plastic hemostat to hold the slide, the treated glass slide was rinsed thoroughly with water and was again tested under the water break test. The slide surface was rinsed thoroughly with isopropanol. The slide was soaked for 2 minutes in isopropanol and rinsed again with isopropanol. The slide was immediately hung in the TTIP/isopropanol solution and stirred. The vessel was covered to minimize pickup of moisture from the air, and allowed to react for about 120 seconds. During this time, the TTIP reacted with the Si—OH groups on the surface of the glass slide to form O—Si—O—Ti-iOPr linkages, although the linkages may not have formed rapidly until the heating step below. The slide was removed very slowly (e.g. 1 cm/min) using the hemostat and was laid flat on an inverted bottle cap in a vacuum desiccator to dry for a few minutes. The standing time in the room air (humidity level and contact time) was adjustable since water vapor diffuses to the surface of the slide causing hydrolysis reactions (the "sol" in sol-gel), i.e., $$Ti(iOPr)_4 + 2H_2O \rightarrow TiO(iOPr)_2 + 2iPrOH$$

$$TiO(iOPr)_2 + 2H_2O \rightarrow TiO_2 + 2iPrOH$$

Excess water must be avoided so that the silanol groups on the surface of the slide may react, i.e., $$\text{glass surface-Si—OH} + Ti(iOPr)_4 \rightarrow \text{Si—O—Ti(iOPr)}_3 + iPrOH$$

Similar reactions couple the $TiO_2$ anatase particles to the surface of the glass and to each other,

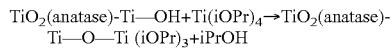

$TiO_2(anatase)\text{-}Ti\text{---}OH + Ti(iOPr)_4 \rightarrow TiO_2(anatase)\text{-}Ti\text{---}O\text{---}Ti\,(iOPr)_3 + iPrOH$ It is noted, however, that thoroughly desiccated (water-free) surfaces are also not useful since dehydration of surface Si—OH and Ti—OH groups occurs, which would remove the hydrogen needed to produce the iPrOH product at low energy. The time spent at this room temperature condition can be adjusted since the coating slowly reacts during this time.

While still lying flat, the slide is oven-dried at 80-90° C. for 20 minutes to finish the cure. The time, temperature and heating rate (° C./min) parameters are adjustable. Heating too fast can blow out solvent, causing massive disruption of the film due to out gassing, while heating too high a temperature can cause too much condensation resulting in shrinkage, leading to pulling away of the film and cracking. Porosity is expected to be important so that water can penetrate and active oxygen can leave the reaction zone.

In order to obtain slides having a thicker $TiO_2$ coating, the above steps are repeated one or more times.

The slide was heated to 250° C. for two hours to fully cure and set the coatings. This temperature was needed to convert the amorphous $TiO_2$ formed from the TTIP into anatase. *Ind. Eng. Chem. Res.* 1999 38(9), 3381. Alternatively, a slide can be pretreated as above except heat the coating to 350° C. at the rate of 3° C./min and hold at this temperature for 2 hr. Miller, et al. *Environ. Sci. Technol.* 1999, 33, 2070. Another alternative is to prepare the sol-gel solution in place of the anatase/TTIP slurry. Colloid C in Aguado, M. A., et al., *Solar Energy Materials. Sol. Cells,* 1993, 28, 345. The slide was then removed and allowed to cool to room temperature.

The coating adhesion of the $TiO_2$ anatase to the glass slide was tested by abrasion with a rubber policeman, tape test, etc. Also, the coating adhesion was tested for other properties including thickness, tendency to crumble/flake off, visual appearance, etc.

The experiments were repeated as needed to improve adhesion and other properties. An additional step of a 400° C. treatment for one hour can used to set $TiO_2$ (anatase) particles onto a quartz sand slide (Haarstrick, et.al. 1996).

$TiO_2$ Coating Photochemistry Testing

Two $TiO_2$ coating photochemistry testing procedures were conducted, the first to determine whether electrons were generated and the second to determine whether active oxygen was generated. First, the $TiO_2$ was tested by a negative charge/electron generation test. Methyl viologen ($MV^{2+}$) blue color ($MV^+$) was applied onto the anatase coating and was subjected to laser light. A rapid appearance of dark blue color qualitatively, validating electron formation. $MV^+$ blue color was not permanent since $MV^+$ is a free radical/charge transfer complex, which easily releases $e^-$ and returns to colorless ground state. Dried coating inhibited the performance of coating (dried minerals block surface sites), but was easily cleaned.

A second test conducted on the $TiO_2$ coating layer was the active oxygen generation test. Methylene blue was used on the $TiO_2$ coating to determine the presence of active oxygen. The methylene blue color was rapidly destroyed at the point of the laser light in the presence of anatase coating, validating active oxygen formation, since oxidized oxygen reacts with methylene blue.

Light Source

The light source used was an argon laser at 364 nm line (400 mwatts/cm$^2$) available (tunable to lower powers). The argon laser used has a total power of 2 watts. Alternatively, a number of UV sources were available for use, including Hg arc lamps using a 365 nm line.

Anode Conductor Layer 36

The anode conductor layer was formed by placing a very thin film of uniform metallic conductor having a thickness of less than about 0.2 @m using e-beam vapor deposition onto a transparent window. The thin film was formed of Ti metal. Conductor line spacing, width and thickness optimization may be required for the anode conductor layer to prevent excessive attenuation while provide sufficiently close conductive areas to sweep electrons away from $TiO_2$ layer.

Dissolved Oxygen Generating Catalyst Layer 34

A dissolved oxygen generating catalyst layer was formed from $MnO_2$ particles onto the surface of the $TiO_2$ (anatase) layer. The $MnO_2$ particles were applied (<5 u) as a iPrOH slurry with or without the anatase/Ti(iPrO)4 mixture. A significant surface of the $TiO_2$ (anatase) layer was coated (~⅓) by the $MnO_2$. Adding the $MnO_2$ drop wise and allowing it to evaporate was effective. The $MnO_2$ was added to increase % surface area covered by $MnO_2$ particles and to make the $MnO_2$ more adherent using the $Ti(iOPr)_4$ binder.

Flow Through Cell

The flow through cell was designed with fluid inlets and outlets on the same side. Silicone gaskets and spacers, acrylic external housing and stainless steal tubing connectors were used in forming the flow through cell. In the flow through cell, the anode was the continuous Ti plate and the cathode was a platinum foil strip.

Electrical Connection of Flow Through Cell

The electrical connection of the flow through cell was wired as an open circuit with a current meter and current regulator inline. The electrical connection of the flow through cell could also be formed by applying bias voltage added with the in-line current meter and current regulator. The electrical connection of the flow through cell could also be formed by placing a resistor and a current meter inline with a voltage reading across the resistor.

Divided Cell

A divided cell was designed with both sets of fluid inlets and outlets on the same side with the through-anode, through-acrylic housing and silicone spacer internal flow paths and on the side opposite the glass slide. The divided cell was further designed to include silicone gaskets or spacers, acrylic external housing, NAFION membrane, and stainless steel tubing connectors.

Active Oxygen Testing

A Locke's Ringer saline test solution was prepared with 150 ppm redox dye (methyl viologen, $MV^{2+}$). Also, a 10 uM solution of methylene blue was prepared in the Locke's Ringer solution. Matthews, R. W., *J. Chem. Soc., Faraday Trans.* 1, 1989 85(6),1291. The molar absorbtivity for methylene blue at 660 nm is 66,700±350 cm$^{-1}$M$^1$. The coated test slide was assembled with an attached UV lamp/laser. The Locke's Ringer solution was then added to the coated test slide via a circulating pump. After steady conditions were attained, the coating was illuminated directly/indirectly with UV light. The saline solution was monitored for appearance of blue color ($MV^{2+}$(colorless)+e-→$MV^+$(blue)) and dissolved oxygen. Gas samples were sampled for GC assay ($CO_2$, $O_2$ not due to air).

Results

Figure 9:
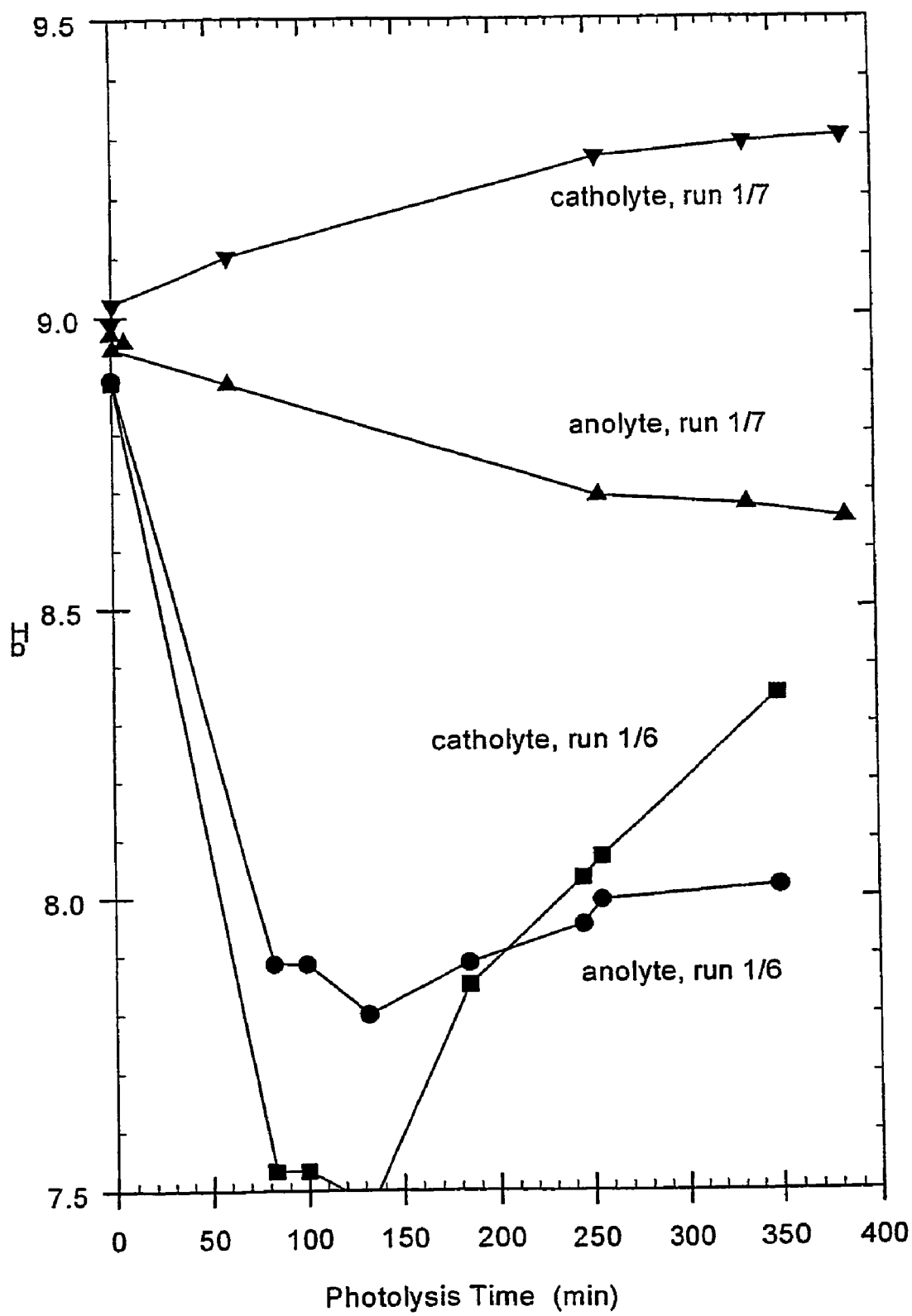
FIG. 9 shows a graph illustrating the relationship of the pH profile of the anolyte and catholyte during photolysis (i.e. photolysis time, minutes) using the photolysis cell.

The artificial lung was tested in order to determine whether the chemical formulations occurred as predicted. The testing was conducted using Locke's Ringer solution, which is a saline solution that mimics blood. The qualitative results of the testing are as follows:

1. Highly efficient U.V. light absorption by thin films of $TiO_2$ (anatase) to impart energy into the anatase matrix was visually apparent in that the UV light is substantially absorbed. Attenuation by any metal conducting film present was measured and corrected separately.
2. Generation of active oxygen (AO) at the anatase surface using the energy from the UV light was evidenced by methylene blue dye disappearance at the surface of the anatase film opposite the side irradiated by the UV laser.
3. Generation of free electrons ($e^-$) at the anatase surface using the energy from the UV light was evidenced by methyl viologen blue dye color appearance at the surface of the anatase on the side opposite the side irradiated and only at the location of irradiation.
4. Transport of the free electrons ($e^-$) generated above to a conductive Ti anode surface, which were then swept away so that the free electrons do not recombine with the active oxygen also produced above was evidenced by electrical current in the anatase semiconductor film, to a metallic collector, wire and amp meter. The electrical current was found to flow only when the laser was on and the electrical current never flowed when the laser was off. The effect was observed through numerous off/on cycles, and the electrical current measured was proportional to the laser intensity up to a saturation point.
5. The release of hydrogen ions ($H^+$) and pH drop was found for the anodic compartment in a continuously circulated and irradiated cell. The opposite pH change was found for the cathodic compartment, which was consistent with the pH effect expected when water is separated into active oxygen and hydrogen ions at the anatase surface. FIG. 9 shows a plot of the pH profile of the anolyte and catholyte during photolysis using the photolytic cell. The opposite trends in the plot are as predicted based on the photosynthesis mimic chemistry, decrease in pH in the anolyte and a pH increase in the catholyte. The lower initial pH in the catholyte in Run 1/6 reflects a startup condition with a slightly lower pH. Run 1/7 used a pre-equilibrated photolytic cell to remove any inconsistent readings during start up conditions.
6. The conversion of $HCO_3^-$ ions from the synthetic serum electrolyte, i.e., Locke's Ringer solution, into $CO_2$, was in part observed by the formation of more $H_2O$. $H_2O$ is the expected product to be formed along with $CO_2$ during the bicarbonate ion conversion to carbonic acid and ultimate conversion to $H_2O$ and $CO_2$ using the $H^+$ ions released during the formation of active oxygen. $CO_2$ production was measured by gas chromatography (GC) analysis of off-gases, or calculated from pH changes. The $CO_2$ level found by GC analysis was significantly greater than atmospheric level, further indicating the formation of $CO_2$.
7. The generation of alkalinity at the cathode and related pH change indicated that the free electrons produced during the reaction of water into active oxygen were conducted away from the anode and consumed in a non-$O_2$ reducing manner, i.e., by reduction of water to hydroxide ion and $H_2$ gas.
8. Generation of $O_2$ as dissolved oxygen from an $MnO_2$ catalyst coating on the anatase from an active form of oxygen added to the test media was found.

All of the verified steps appeared to react at good rates. Using the electrical current generated, a rough size for the photolytic cell unit for a 100 ml/min $O_2$ flow rate was calculated and found reasonable. Also, a number of coating fabrications were tested that were designed to allow $MnO_2$ particles, as a coating or dopant, to react with long-lived, soluble forms of active oxygen. These $MnO_2$ coatings were found to generate abundant quantities of dissolved oxygen under the testing conditions.

Calculating Size of Photolytic Cell Required

Figure 8:
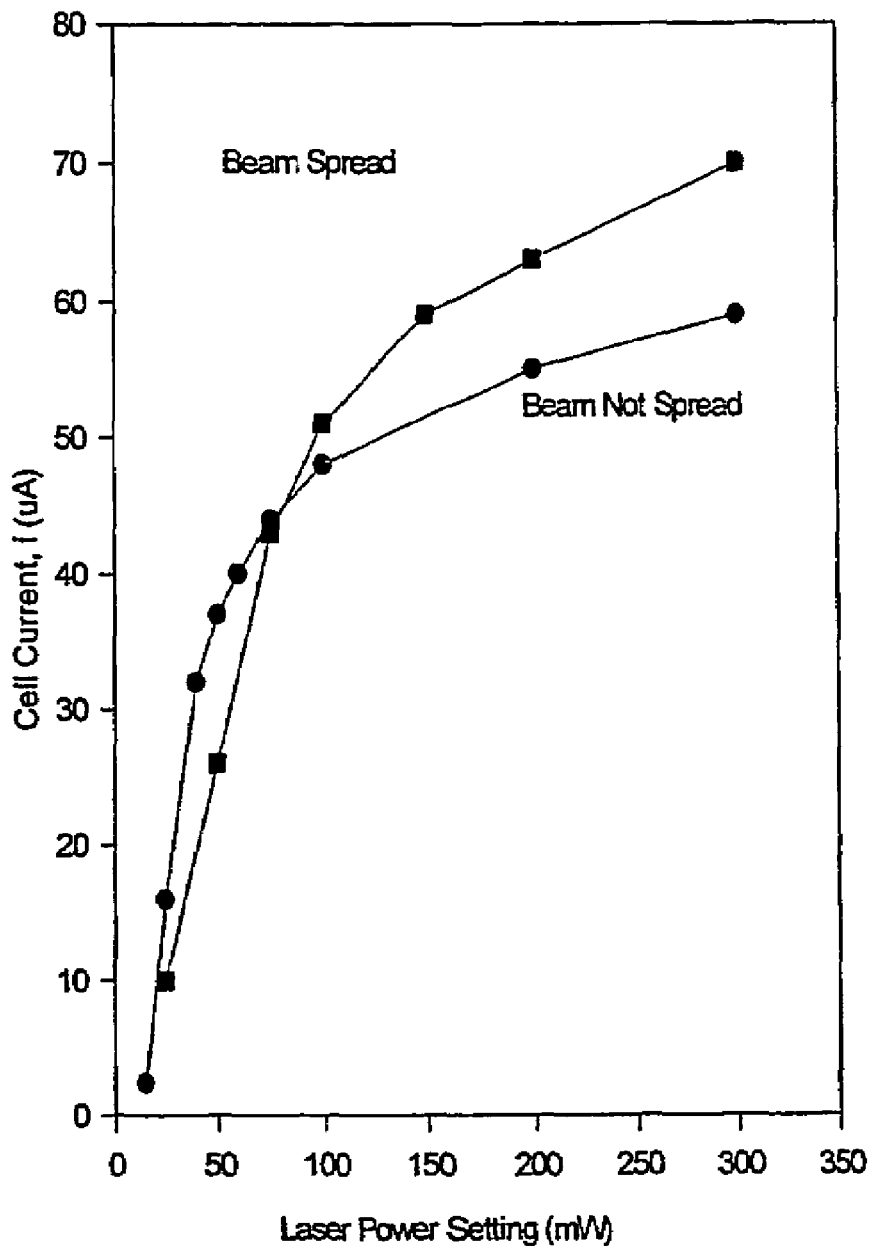
FIG. 8 shows a graph illustrating the plot of observed electrical current generated in the anode-to-cathode wire loop by the photolysis cell versus laser power intensity.

Preliminary testing was conducted on the photolytic cell to determine the size of a cell required to generate the target oxygen rate in an average adult human body of about 150 mL/min (STP) of $O_2$ for 5 L/min of blood flow, which is the average normal adult human blood flow rate. FIG. 8 shows the measure of the cell current versus the laser power setting in 0.60 g/L $NaHCO_3$ and 4% MeOH electrolyte. As indicated, photo-absorption results in the generation of current in the test cell in proportion to laser light intensity. It is noted that the laser power setting is not the same as the actual impinging laser beam energy, but rather the laser power setting is greater than and proportional to the actual laser beam energy by a factor of about 2. Also, the power setting is of the laser itself and not of the 363.8 nm beam after it is separated from the other two lines produced by the laser. The laser power setting was measured after the laser moved around the optics bench and penetrated the glass slide and Ti collector film Although the data in FIG. 8 represents early exploratory testing and is far from optimized, it was used to calculate the size of a cell that would be needed to generate the target oxygen rate, 150 mL (STP)/min. From FIG. 8, a limiting cell current density of 70 uA/$cm^2$ can be estimated. Using this value, a cell surface area needed to generate 150 cc $O_2$ gas/min (STP) was calculated. If one flat sheet cell were used in contact with the blood, it would need to be 7.5×7.5 meters in area (56 $m^2$) to provide 150 mL $O_2$ gas/min. Since no optimization has been done to date which might improve rates and since stacking of smaller plates to achieve a net large surface area is routine in electrochemical cell technology, this level of performance is considered encouraging as an early test result. Although the quantum efficiency was not determined in this qualitative testing, it appeared to be low. Many options are available to improve on the quantum yield. An improvement of 10 times would require a blood contact area (BCA) of 75 cm on a side, which then could be cut in half (by area) to 53 cm square by double siding the cell, i.e., one cathode, two anodes. Using six pairs, as is done in automotive batteries for example, reduces these dimensions to a cube of about 20 cm on a side, well within acceptable dimensions for an emergency use extracorpreal device without ancillary equipment. Therefore, a sufficiently small photolytic artificial having a small stack of photolytic cells appears possible with a 10 time improvement over the current production rates, assuming a high correlation between cell electrical current and dissolved oxygen production. Reasonable target values for optimized photo current efficiencies are expected to be in the 0.1-10% range.

FIG. 8 also shows that spreading the laser beam to about 1 $cm^2$ resulted in about the same current production as did leaving the beam as a 3-4 mm spot. This result suggests that the photons were being supplied faster than they could be consumed. Therefore, significantly enhanced utilization of the laser power appears possible. Efficiency enhancements might be accomplished by pulsing the beam to allow the chemical reactions to keep up and/or further spreading it using optics.

Example 2

To demonstrate the ability of the photolytic reaction sequence to generate DO, two Hansatech batch reactors were set up, one for liquid phase (DO), and one for gas phase oxygen ($PO_2$) detection. Both gas tight reactors were fitted with an oxygen membrane sensor and a window for illumination. These reactors were designed to allow quantitative assessments of oxygen production and quantum yields. Although, the results verify that DO can be produced photolytically from water, and that $O_2$ can be produced from AO using a thin film catalyst.

The critical step of photolytically producing DO from $H_2O$ was illustrated in the liquid phase cell using a slurry of the anatase titania ($TiO_2$) photon absorber and dissolved ferric ion at pH 1.9 as an electron absorber. While not intended to be used in the final device, the use of ferric ions here allows the tests to be run within the setting of the electrically isolated cell, in which the ferric ions are maintained in solution by the relatively low pH. The ferric ions are characteristically converted to ferrous ion ($Fe^2$+aq) during photolysis by the absorption of photolytically mobilized electrons from the anatase ($Fe^3$+aq+$e_{scb}^-$→$Fe^{2+}$aq). The photo-activated anatase, which is then electron deficient and highly energetic, replaces the electrons from adjacent water molecules. This occurs despite the high thermodynamic stability of liquid water, due to the high energy level of the photon. In the absence of ferric ions, there is either no DO change or $O_2$ depletion. $O_2$ is depleted by chemical reduction by the electrons, which accumulate with photolysis. Both of these blank conditions (with and without air) were demonstrated with the described experimental apparatus, in which the ferric ions are absent. Likewise, after a suitable photolysis time, the ferric ions became nearly fully converted to ferrous ions. Thus, owing to the fact that ferric ions were largely depleted, $O_2$ generation rate drops off. This phenomenon was due to the recombination of $O_2$ with the photolytically generated electrons, now available for reaction. By cycling the UV light on and off, it was shown that the generation of $O_2$ only occurred when the cell was illuminated and not otherwise.

A second critical step, that of generation of $O_2$ from AO and a catalytic coating, was shown experimentally using hydrogen peroxide ($H_2O_2$) as the AO form. This test was performed by placing a 1 in$^2$ $TiO_2$/$MnO_2$-coated glass test wafer in the gas phase reactor, in contact with Lockes-Ringer synthetic blood serum (pH 7.4) solution. The $H_2O_2$ was introduced as a 3% (w/w) aqueous solution in a sponge layer on the side opposite the catalytic coating. The presence of intermediate foam provided a time delay, due to the time it takes the $H_2O_2$ to diffuse through the electrolyte via the foam pores, and thereby to reach the film. This time delay allowed the reactor to be degassed of atmospheric $O_2$ prior to the commencement of the catalyzed disproportionation reaction, which produced $O_2$. The $PO_2$ was measured as a function of photolysis time. Although pure $H_2O_2$ is stable, many catalysts exist to mediate the disproportionation reaction to $O_2$ and $H_2O$, necessitating blank corrections. The $O_2$ contribution of the catalytic surface was separated from the remaining medium by running reference (catalyst-free) tests. After removing atmospheric $O_2$ by sparging with argon, it was verified that total $O_2$ level in the cell was constant at 7650 nmol. With the peroxide and illumination (but with no catalyst coating) $O_2$ accumulated over 300 minutes at 1.45 mmole $O_2$/hr. In the presence of the one in$^2$ $TiO_2$/$MnO_2$ coated wafer, the same test yielded $O_2$ at a constant rate of 2.44 mmole $O_2$/hr, or 1.0 mmole $O_2$/hr above background, a 69% increase compared with the blank condition. Therefore, this test proves that $O_2$ can be produced from AO by the $TiO_2$/$MnO_2$ coating provided AO is made available to it. It is assumed that most, if not all forms of AO, will react with this coating to form $O_2$ in a similar manner. When $H_2O_2$ was applied directly to the catalyst coating, it was verified that $O_2$ formation occurs in a manner, which was instantaneous and complete. Therefore the observed $PO_2$ generation rate reflects mostly the diffusion of $H_2O_2$ The data shown were used to calculate the surface area needed to approximate a physiologic rate of oxygen generation. Using the value for a limiting cell current density of 70 uA/cm$^2$ and assuming the cell is configured as a flat sheet, the surface area needed to generate the target oxygen rate would be 7.5×7.5 meters, or 56 m$^2$. Improvements of efficiency are expected by optimizing the surface properties of the photoreactive surface material, as well as modifications of design, including double-siding the cell (one cathode, two anodes), stacking the photo-reactive surfaces, and improving the efficiency of laser activation. A reasonable range for optimized photo current efficiency should be 0.1-10%. Tests have shown that significantly enhanced utilization of the photosensitive surface area also appears feasible. It is estimated that the optimization steps will result in an improvement of yield of approximately 100-fold, and since stacking of smaller plates to achieve a net increase of surface area will be used, the generation of physiological oxygen concentrations should be achievable.

Example 3

A test cell was created to determine the extent to which the indicated chemical conversions occurred only during illumination, and in association with the active surface material. FIG. 3 is a diagram of the flow cell constructed with the essential elements of design, a conductive coating of vacuum deposited Ti metal, a coating of adherent $TiO_2$ (anatase) and a $MnO_2$ particulate layer. UV laser light was introduced to irradiate transparent glass or quartz substrate. This cell was used to collect pH, electrical current, dissolved oxygen, and gas phase $CO_2$ data as a function of laser irradiation.

Synthesis of Photoactive Layers

The photoactive constructs consisted of a glass substrate, a conducting layer, and a photoactive layer. The glass substrates were 25 mm×9 mm in size, and 98% transmissive at the desired wavelength. The (Ti) conductive layer(s) were laid down on the glass surface using a vacuum sputter coating procedure. In order to validate the efficiency of Ti, various metals including Ni, Cu, Cr, and Au, and the mixed metal oxide indium tin oxide (ITO), were also tested relative to Ti. Depending on the conductive material and the thickness of the layer, these samples were treated in 1N HCl acid for 15, 30, or 60 sec in order to impact adhesive functionality to the surface. After rinsing with water and isopropanol, the photoactive layer was then applied.

The photoactive layer consisted of either titanium dioxide ($TiO_2$), $MnO_2$ and $TIO_2$, or $RuO_2$/Pt doped $TiO_2$. Titanium dioxide was obtained from Degussa as Titan Dioxide P25. The powder has a primary particle size of ~20 nm and is 70-80% anatase and 30-20% rutile. The $TiO_2$ powder was acid treated prior to deposition, in order to enhance adhesion, by mixing 1 g $TiO_2$ in 80 ml of a 1N HCl and 0.1% HF solution for 1 minute. The resulting slurry was divided equally into two centrifuge tubes and centrifuged until the sedimentation was achieved. The acid was decanted and replaced with water and the particles re-suspended. The samples were centrifuged and the liquid decanted. This water rinse was then repeated. After the second water rinse and decanting, 40 ml of isopropanol was added. The manganese (IV) oxide had a particle size of <5 um and was used as received. The $RuO_2$/Pt doped $TiO_2$ was prepared using a two-step procedure. The first step involved a wet-impregnation by combining 1 g $TiO_2$ and 31 mg $RuCl_3$ in 80 ml of a 0.1 mM $HNO_3$ solution and mixing for 1 hr. The solution was evaporated through heating to obtain the dry solid. The second step involved a photo-platinization in which 0.125 g of the $TiO_2$/$RuO_2$ was added to a vacuum flask containing 100 ml $H_2O$ and 6 ml of 37% formaldehyde (stabilized with methanol). The solution was mixed and bubbled with argon for 5 minutes. Then 19.8 mg of hydrogen hexachloroplatinate (IV) ($H_2PtCl_6$) was added, and the mixing and the flask sealed. A high-pressure mercury lamp was used to irradiate the solution for 2 hours. After irradiation, the solution was transferred to a beaker and heated to remove the liquid. The sample was then placed in a vacuum oven for three days to remove excess organics.

These oxide materials were added to the substrate using a spin coating technique. The glass slides containing the conducting layer were placed on a vacuum chuck and rotated at 1000 rpm. For the $TiO_2$ coating, 0.5 g of the acid treated material was added to 40 ml iPrOH and mixed for 30 minutes. 0.050 ml $H_2O$ and 0.100 ml titanium isopropoxide (TTIP) was added to this solution. After mixing for 30 minutes, the solution was added drop-wise to the rotating substrate for a total volume of ~12 ml. In the case of the constructs containing $MnO_2$, following the addition of 9 ml $TiO_2$, 0.20 g $MnO_2$ was added to the remaining slurry. Exactly four ml of the resulting solution was then added drop-wise to the substrate. The $RuO_2$/Pt doped $TiO_2$ was (0.125 g) was added to 10 ml iPrOH. After 15 minutes of mixing, 50 uL water and 25 uL TTIP was added and allowed to mix for an additional 15 minutes. The solution was then added drop-wise to the substrate for a total volume of 9 ml.

The coated samples were all allowed to air dry at room temperature overnight They were then placed in a preheated tube furnace and heated for 45 min. under a 1 L/min. flow of nitrogen. The temperature at which the samples were heated depended greatly on the composition of the conducting layer. It was observed early on that a number of materials partially or completely oxidized at even the lowest temperatures. Therefore, samples containing conducting layers of Ti or ITO were heated at 350° C. while samples containing Ni or Cr were heated at 209° C.

Measurement of Active Oxygen

A test solution was prepared with Lockes Solution along with 150 ppm redox dye (methyl viologen, $MV^{2+}$). After steady-state conditions were attained, the solution was illuminated with UV light, and monitored for the appearance of blue color [$MV^{2+}$(colorless)+e− →$MV^+$( blue)], and dissolved oxygen. Gas samples were gathered for GC assay ($CO_2$, $O_2$ not due to air (evidenced by presence of Ar). These steps were repeated using a 10 uM solution of methylene blue in the saline solution, MB, saw a drop in MB concentration with irridation time (bleaching of the blue color), but not otherwise. The molar absorbtivity used for methylene blue (conc. 660 nm) was 66,700±350 $cm^{-1}$ $M^{-1}$.

Measurement of Dissolved Oxygen Generation

A liquid phase reaction chamber was used to monitor dissolved oxygen production. This device utilizes a Clark Electrode to measure dissolved oxygen. A two-point calibration procedure was used on the dissolved oxygen sensor; 2.35 ml of air-saturated water at 36° C. (217.2 nmol/ml) was added to the cell and measurements were taken. Then the cell was emptied and flushed with nitrogen to obtain a zero-oxygen measurement. A blood substitute was then added to the batch cell at a volume of 2.35 ml and a temperature of 36° C. This blood substitute, commonly referred to as Lockes-Ringer Solution®, contains 0.15M NaCl, 5.6 mM KCl, 4.2 mM $CaCl_2*2H_2O$, and 7.1 mM $NaHCO_3$. Shortly after this addition, deoxygenation of the solution was performed by bubbling with nitrogen. Once the oxygen content dropped to minimal levels, the nitrogen bubbling is halted, the photoactive construct and Pt wire counter-electrode are added, and the reaction chamber is sealed. The process of removing the sparge tube and sealing the chamber allows some oxygen from the atmosphere to re-enter the system. It takes some time for the oxygen concentration to equilibrate. Once this occurs, a bias voltage is applied to the cell to produce electric field to promote immediate removal of photo-generated electrons, but insufficient to produce electrochemical reactions. A DC power source is used to supply this constant potential to the system; a Pt wire is connected as the cathode and the Cu wire extending from the photoactive construct, and not exposed to the test solution, is connected as the anode. Electrical current is measured with a high-impedance VOM multimeter. The UV light source is directed to the reaction chamber through a liquid light pipe. The light emitted from the pipe is filtered to produce light of only 365 nm; the intensity at this wavelength is 88.1 $mW/cm^2$. The system is illuminated through a small quartz window in the side of the reaction chamber. For most of the experiments, the UV light was cycled on and off a few times to ensure the oxygen production was a result of a photocatalytic phenomenon, not a galvanic or electrolytic one. Heating of the solution during illumination was prevented by use of the water jacket surrounding the reaction chamber. Water from a constant temperature, circulating bath flowing through this jacket kept the system at a constant 36° C. throughout the experiment.

Additional Methods and Disclosure of Greater Details

Batch Cell Dissolved Oxygen Production

The Hansatech liquid phase reaction chamber was used to monitor dissolved oxygen production. This device utilizes a Clark Electrode to measure dissolved oxygen. A two-point calibration procedure was used on the dissolved oxygen sensor; 2.35 ml of air saturated water at 36° C. (217.2 nmol/ml) was added to the cell and measurements were taken, then the cell was emptied and flushed with nitrogen to obtain a zero-oxygen measurement. A blood substitute was then added to the batch cell at a volume of 2.35 ml and a temperature of 36° C. This blood substitute, commonly referred to as Lockes Ringer Solution, contains 0.15 M NaCl, 5.6 mM KCl, 4.2 mM $CaCl_2*2H_2O$, and 7.1 mM $NaHCO_3$. Shortly after this addition, deoxygenation of the solution is performed by bubbling with nitrogen. Once the oxygen content drops to minimal levels, the nitrogen bubbling is halted, the photoactive construct and Pt wire counter-electrode are added, and the reaction chamber is sealed. The process of removing the sparge tube and sealing the chamber allows oxygen from the atmosphere to enter the system. It takes some time for the oxygen concentration to equilibrate. Once this occurs, a bias voltage is applied to the cell. A DC power source is used to supply a constant potential to the system; the Pt wire is connected as the cathode and the Cu wire extending from the photoactive construct is connected as the anode. Current is measured with a multimeter. Note that the circuit is not complete and no current flow is observed unless the system is irradiated with UV light. The UV light source is directed to the reaction chamber through a liquid light pipe. The light emitted from the pipe is filtered to allow light of only 365 nm; the intensity at this wavelength is 88.1 mW/cm². The system is illuminated through a small quartz window in the side of the reaction chamber. For most of the experiments, the UV light was cycled on and off a few times to ensure the oxygen production was a result of a photocatalytic phenomenon, not an electrolytic one. Heating of the solution during illumination was prevented by use of the water jacket surrounding the reaction chamber. Water flowing through this jacket kept the system at a constant 36° C. throughout the experiment.

Quantum Yield Calculations

For any photochemical reaction, inefficiencies occur and not all absorbed photons lead to products. Quantum yield was therefore calculated for the reactions. The number of photons absorbed was determined by ferrioxalate actinometry. When solutions of ferrioxalate ($Fe^{3+}$) are irradiated with UV light, $Fe^{2+}$ is produced. The $Fe^{2+}$ yield is determined by complexing with 1,10-phenanthroline. It is well known that the $\Phi_{Fe^{2+}}$ at 366 nm is 1.21, therefore, by measuring the number of moles of $Fe^{2+}$ ($n_{Fe^{2+}}$) formed, one may calculate the quantum yield of the reaction of interest ($\Phi_{DO}$) by:

$$\Phi_{DO} = \frac{n_{DO} t_{DO} \Phi_{Fe^{2+}}}{n_{Fe^{2+}} t_{Fe^{2+}}}$$

Potassium ferrioxalate was prepared by combining 250 ml of a 1.5 M $FeCl_3$ aqueous solution and 750 ml of a 1.5M potassium oxalate aqueous solution. Vigorous mixing resulted in a green precipitate, which was then filtered, redissolved in hot water, and recrystallized. The resulting pure crystals of potassium ferrioxalate were dried in the oven at 50° C. for 1 hr. A 0.1N Sulfuric acid solution containing 6 mM potassium ferrioxalate was added to the reaction chamber and irradiated 10 min. After irradiation, 1.0 ml of the solution was extracted from the chamber and combined with 0.8 ml water, 0.2 ml of a 0.1 wt % 1,10-phenanthroline solution, and 0.5 ml of a buffer solution prepared from 100 ml of 1.7N sodium acetate and 60 ml of 1N sulfuric acid diluted to 166 ml. An identical solution was also prepared, but not irradiated, for use as a blank. These solutions were kept in the dark for 1 hr. then analyzed with a Hach DU/400012 UV-vis spectrophotometer using a cell with a 1 cm path length. The number of moles of Fe2+ formed was determined by the following equation:

$$n_{Fe^{2+}} = \frac{V_1 V_3 \log(I_o/I)}{V_2 l \varepsilon}$$

where $V_1$=volume of actinometer solution irradiated, $V_2$=volume of aliquot extracted from chamber, $V_3$=final volume after aliquot has been diluted, I=path length of the spectrophotometer cell, and $\varepsilon$=molar extinction coefficient of the $Fe^{2+}$ complex.

The Hach was calibrated using a series of six solutions containing 0, 1, 2, 3, 4, and 5 ml of a 0.1N sulfuric acid solution with 0.5 mM ferric sulfate. These solutions were then diluted to 10 ml with 0.1N sulfuric acid. Then 2 ml of a 0.1 wt % 1,10-phenanthroline solution, 5 ml of the buffer solution, and 3 ml water were added to each sample. After standing in the dark for 1 hr., these solutions were used to obtain the molar extinction coefficient by plotting log ($I_o$/I) versus molar concentration of the $Fe^{2+}$ complex as determined by the UV-vis spectrophotometer at 5100 Å. The value obtained was 1.17*10⁴ Liters/mol-cm.

Glass/Quartz Slide Preparation

1. Degrease slide by swirling in toluene (or MEK). Allow to flash dry in the air (should take <1 min)
2. Soak in warm Micro® cleaning solution (2 min)
3. Rinse thoroughly with 18MΩ Dl water ("water" from now on) from a squirt bottle
4. Immediately soak 2 min in a water bath
5. Rinse thoroughly with water from a squirt bottle. Drain, but do not let dry.
6. WITH CAUTION, submerge in a solution of concentrated sulfuric acid. (Use a jar with lid so that the sulfuric acid can be used in future tests). Let stand 2 min. Use a PP heamastat to hold the slide when it is inserted/withdrawn.
7. Withdraw the slide, allow it to drain, move it over a beaker away from the sulfuric acid, then rinse thoroughly with water. (CAUTION: drops of water added to the concentrated sulfuric acid will cause it to spatter!)
8. Soak 2 min in a water bath
9. Perform water break test.
10. Using a plastic (Nalgene®) beaker with cover watch glass, and in the hood, dip the slide for 2 min in a solution of 0.1% HF and 1N HCl (the time of this imersion is an adjustable parameter for future tests).
11. The surface of the glass now contains a high population of Si—OH linking groups. These slides should be kept wet, and can be stored indefinitely in 5% HNO3

Particle Preparation

1. Add 1.0 g $TiO_2$ (anatase) to a plastic (Nalgene®) beaker with cover watch glass, add a magnetic stir bar to it, then in a hood, add 80 mL of 0.1% HF and 1N HCl. Start stirrer. Stir such that the solids are well suspended. Mix 60 seconds then proceed immediately to the next step. (The HF level and reaction time in this step are adjustable parameters. It's important to not measurably reduce the weight of the particles, the objective is just to change the surface of them.).
2. Divide the slurry between two 50 mL, capped centrifuge tubes and centrifuge (5 min may be sufficient), if not try 10 min.
3. Discard supernatant to waste receiver.
4. Rinse 3× with 40 mL portions of water to each tube (add, cap, vortex thoroughly, centrifuge, decant, repeat). Note the settling characteristics of these fine particles—is the supernatant clear? Is a packed cake produced? Does settling occur rapidly? etc.
5. Rinse 3× with 40 mL portions of isopropanol to each tube (add, cap, vortex thoroughly, centrifuge, decant, repeat).

Application of Coating to Glass Slide

1. Resuspend the pretreated anatase particles from one of the tubes from Step B.5 magnetically in a tall/narrow jar containing isopropanol (isopropyl alcohol, iPrOH) sufficiently deep to cover the glass microscope slide. Initiate magnetic stirring to keep the particles suspended. The amount of particles used is an adjustable parameter in determining the thickness of the final coating produced.
2. Add sufficient $Ti(iOPr)_4$ (TTIP) to yield a 0.2 vol % solution (e.g. by adding 160 uL TTIP per 80.0 mL iPrOH used in the above step).

3. Using a plastic hemastat to hold the slide, rinse one of the treated glass slides from section A above thoroughly with water from a squirt bottle. Confirm that the surface still passes the water break test Then rinse the slide surface thoroughly with iPrOH using a jet from a wash bottle. Soak the slide for 2 min in iPrOH, then rinse again with iPrOH using a jet from a wash bottle. Proceed immediately to the next step.
4. The slide from the previous step is immediately hung in the mixing slurry produced in Steps C.1 and C.2. above. Try to maintain good stirring. Cover the vessel, to minimize pickup of moisture from the air, and allow it to react for 120 sec (this reaction time is an adjustable parameter, but probably not a strong one after a few minutes. During this time the TTIP reacts with the Si—OH groups on the surface of the glass slide to form O—Si—O—Ti-iOPr linkages, though these may not form rapidly until the heating step below).
5. Remove the slide very slowly (e.g. 1 cm/min)$^{4/3}$ using the hemastat and then lay the slide flat on an inverted bottle cap in a vacuum desicator to dry (just a few minutes). Keep track of which side is "up". This standing time in the room air (humidity level and contact time) is an adjustable parameter since water vapor diffuses to the surface of the slide causing hydrolysis reactions (the "sol" in sol-gel), i.e.

Ti(iOPr)$_4$+2H$_2$O →TiO(iOPr)$_2$+2 iPrOH

TiO(iOPr)$_2$+2H$_2$O→TiO$_2$+2 iPrOH

Excess water needs to be avoided so that the silanol groups on the surface of the slide get involved, i.e.

glass surface-Si—OH+Ti(iOPr)$_4$→Si—O—Ti (iOPr)$_3$+iPrOH

Similar reactions couple the anatase particles to the surface of the glass and to each other, TiO$_2$(anatase)-Ti—OH+Ti(iOPr)$_4$→TiO$_2$(anatase)-Ti—O—Ti (iOPr)$_3$+iPrOH Note, however, that thoroughly dessicated (water-free) surfaces are also not useful since dehydration of surface Si—OH and Ti—OH groups occurs, removing the H needed to produce the iPrOH product at low energy, i.e. simple H transfer reaction.

The time spent at this room temperature condition is an adjustable parameter since the coating "cures" (slowly reacts) by the above reactions during this time. Note how the coating's appearance changes with time.
6. While still lying flat, oven dry the slide to finish the cure at 80-90° C. for 20 min. These parameters (T and t) are also adjustable as is the heating rate (° C./min). Heating too fast can "blow out" solvent, causing massive disruption of the film due to out gassing. Heating too hot can cause too much condensation resulting in shrinkage, leading to pulling away of the film and cracking. This overheating effect is especially true in the next step. Note also, however, that porosity is expected to be important so that water can penetrate and active oxygen can leave the reaction zone.
7. Repeat steps 3-6 for three additional slides. However, for these slides, repeat the process 2, 4 and 8 times respectively so that a series of slides containing thicker and thicker films is produced.
8. Heat all slides to 250° C. for two hours to fully cure and set the coatings. This temperature is needed to convert the amorphous TiO$_2$ formed from the TTIP into anatase.
9. In a variant on Step 8, perform a separate test using another slide pretreated as above except heat the coating to 350° C. at the rate of 3° C./min and hold at this temperature for 2 hr.
10. In another variant on Step 8, prepare the sol-gel solution as per ref. 44 in place of the anatase/TTIP slurry used above.
11. Remove, allow to cool to room temperature (continue keeping track of what side is up).
12. Test coating adhesion (abrasion with rubber policeman, tape test, etc.), measure/estimate thickness, tendency to crumble/flake off, visual appearance, etc.
13. Repeat experiments as needed (see adjustable parameters listed in the text of the experimental descriptions) to improve adhesion and other properties. In addition, a 400° C. treatment for one hour was used to set TiO$_2$ (anatase) particles onto quartz sand.
14. Send the coated slides forward to active oxygen production testing Active Oxygen Testing Prepared a saline test solution (Lockes Solution) with 150 ppm redox dye (methyl viologen, MV$^{2+}$). Assembled coated test slide with UV lamp/laser attached. Add the first solution to the second as batch or via circulating pump. After steady-state conditions were attained, illuminated the coating with UV light. Monitored the saline solution for appearance of blue color [MV$^{2+}$(colorless)+e− →MV$^+$( blue)], and dissolved oxygen. Gathered gas samples for GC assay (CO$_2$, O$_2$ not due to air (evidenced by presence of Ar). These steps were repeated using a 10 uM solution (Ref. 45) of methylene blue in the saline solution, MB, saw a drop in MB concentration with irridation time (bleaching of the blue color), but not otherwise. The molar absorbtivity used for following methylene blue concentration at 660 nm was 66,700±350 cm$^{-1}$ M$^{-1}$.

Polymeric Sol-Gel Binder for Anatase Nanoparticles to Glass Slide

The general procedure is from J. Membrane Science 39 (988), 243.

General Conditions:
H2O/Ti(iOPr)4=4.0 (mole ratio)
HNO3/Ti(iOPr)4=0.025 (mole ratio)
iPrOH/Ti(iOPr)4=28 (mole ratio)
Gelling time=1.5 hr (increases rapidly with decreasing H2O/Ti(iOPr)4 ratio, but coating cracking increases rapidly with increasing H2O/Ti(iOPr)4)
Slides and particulates were pretreated as before in the usual manner with degreasing, HF pretreatment (excluding HF for the Ti coated slide), etc.

Procedure:
1. Prepare 0.5 g of sonicated, surface activated anatase particles in 25 mL iPrOH (as per previous procedure, include HF treatment).
2. Transfer (1) to a 50 mL beaker with disc magnetic stirrer and cover glass.
3. Start vigorous stirring
4. Add 210 uL (704 u moles) of Ti(iOPr)4 (FW 284.26 amu, d=0.963 g/cc)
5. With continued vigorous stirring, add 50 uL (2.81 mmoles) h.p. DI water dissolved in 5.0 mL iPrOH.
6. Cover with watch glass, stir vigorously for 30 seconds then slowly for 30 min. Then stop and remove stir bar.
7. The product after 30 min represent anatase particles suspended in a TiO2 polymeric sol. Record visual appearance (color, colloidal stability, tendency to ppt or flocculate, etc.). This mixture will thicken (gel) with time (an adjustable parameter).

8. Using a pipet transfer 1.00 mL of the polymeric gel containing anatase particles from Step 7 to a prepared glass slide lying flat inside of a petri dish (slide prepare using usual degreasing/HF procedure)
9. Cover petri dish with lid and let sit overnight at RT.
10. Film should have developed into a clear supported gel containing anatase particles.
11. Cure the film at 250 C for 30 min using a heating rate of 10 C/min.
12. Allow to cool, then test, image, etc.

Repeated the above tests using Ti coated slides.

Methyl viologen dichloride hydrate was obtained from Aldrich Chem. Co. (Cat. No. 85,617-7). This dye turns blue when it picks up an electron from UV (<418 nm) light-activated anatase TiO2. If the activated oxygen is consumed as well (e.g. by added methanol, formic acid, etc.), then color development is more intense (higher yield of electron transfer).

Summary of Results

The initial objective was to test the feasibility of the photolytic concept for re-oxygenating synthetic serum (Locke's Ringer) using thin film constructs. The test cell described above was able (with and without the $MnO_2$ layer) to verify that the chemical conversions occurred only during illumination, and in association with the active surface material. The ability of the thin films of $TiO_2$ to impart energy into the anatase matrix, and thereby to activate the sequence of chemical reactions described above, was shown by several criteria:

The generation of active oxygen at the anatase surface using the energy from the UV light was evidenced by the disappearance of methylene blue dye at the surface of the anatase film opposite the side irradiated by the UV laser (not shown). In turn the generation of "free electrons", $e^-$, at the anatase surface using the energy from equation 1, was evidenced by the appearance of methyl viologen blue color at the surface of the anatase, opposite the site of irradiation. Transport of the electrons to a conductive surface, where they are then removed, so that they do not recombine with the active oxygen being produced was evidenced by electrical current in the anatase semiconductor film, to a metallic collector, wire and amp meter. Electrical current was found to flow only when the laser was on and never when it was off. The effect was observed through many off/on cycles, and the electrical current measured was proportional to the laser intensity. The generation of H+ ions was indicated by the opposite and equivalent changes of pH at the anode and cathode in the photolytic cell as a function of photolytic induction. Lastly, the conversion of bicarbonate ion to $CO_2$ was measured directly by gas chromatographic analysis of off-gases, and was found to be significantly greater than atmospheric level.

Photolytic generation of dissolved oxygen was illustrated in the liquid phase cell using a slurry of the anatase titania ($TiO_2$) photon absorber and dissolved ferric ion at pH 1.9 as an electron absorber. The use of ferric ions here allows the tests to be run within the setting of the electrically isolated cell, in which the ferric ions are maintained in solution by the relatively low pH. The ferric ions are characteristically converted to ferrous ion ($Fe^{2+}_{aq}$) during photolysis by the absorption of photolytically mobilized electrons from the anatase ($Fe^{3+}_{aq} + e^-_{scb} \rightarrow Fe^{2+0}_{aq}$). The photo-activated anatase, which is then electron deficient and highly energetic, replaces the electrons from adjacent water molecules. This occurs despite the high thermodynamic stability of liquid water, due to the high energy level of the photon. In the absence of ferric ions, there is either no dissolved oxygen change or oxygen depletion. Oxygen is depleted through chemical reduction exerted by the electrons, which accumulate in association with photolysis. Both of these blank conditions (with and without air) were demonstrated with the described experimental apparatus, in which the ferric ions are absent. Likewise, after a suitable photolysis time, the ferric ions became nearly fully converted to ferrous ions. Thus, owing to the fact that ferric ions were largely depleted, $O_2$ generation rate drops off. This phenomenon was due to the recombination of $O_2$ with the photolytically generated electrons, now available for reaction. By cycling the UV light on and off, it was shown that the generation of oxygen only occurred when the cell was illuminated and not otherwise.

The presence of electrical potential between the conducting layer of the construct and a Pt counter electrode during illumination produces an electric field across the photolytic layer, which forces electron flow away from the $TiO_2$ layer and results in enhanced dissolved oxygen production. When the voltage bias is removed and the illumination with UV light ceases, the oxygen concentration decreases and the current flow is observed to reverse for a short time. This reversal of current indicates that during illumination, a charge accumulation occurs within the photolytic construct. Once the light source and bias voltage are turned off, electrons flow back into the semiconductor layer and oxygen is adsorbed as in Equation 1.

Based on the feasibility results shown above, applicants designed a prototype photolytic module, which is depicted from the perspective of the physical and chemical configurations. The key features of this system include: 1) Selective removal of gas phase substances, i.e. $CO_2$, $N_2$, or excess $H_2$, will be performed relative to the dissolved oxygen enriched fluid immediately following photolytic induction though a set of gas permeable tubing, whose pore size would selectively exclude the larger hydrated molecules, such as dissolved oxygen; 2) The configuration of photolytic surfaces in a "stacked" configuration, thus enabling a single light source of light to induce photolytic conversion in several surfaces within a relatively confined physical space, whose inlet and outlet flow is closely regulated though flow distributors at either ends. This configuration would result in greatly increased functional surface area for photolytic induction and significantly more efficient use of laser power relative to molecular yield.

Detailed Results

Irradiation of $TiO_2$ in contact with Lockes Ringer solution (pH~7.2) at 36° C. using a high pressure mercury lamp (0.93 mW/cm² at 365 nm) did not result in production of oxygen. Indeed, it was observed that when no electron acceptor is present, photoadsorption of oxygen onto the surface of $TiO_2$ occurs (1) according to the equation:

$$e_{cb}^- + O_2 \rightarrow O_{2(adsorbed)}^{\cdot -} \qquad \text{eqn. (1)}$$

In subsequent experiments, two methods of electron withdraw were used—alternative electron acceptor ions in solution and a voltage bias to induce a current flow.

Ferric ions were then utilized as an electron acceptor in sulfuric acid solution (pH=1.9). Oxygen production was observed when either the high pressure mercury lamp (HP Hg) or the high intensity EFOS lamp (88.9 mW/cm² at 365 nm) was used. With the higher powered lamp, the rate of production was much higher: 112.8 nmol/ml/s when illuminated with the EFOS and 5.076 nmol/ml/s when illuminated with the HP Hg. It was also observed that $O_2$ production occurred only when the system was illuminated. When the EFOS lamp was turned off, oxygen production halted and the $O_2$ concentration decreased slightly. This decrease in concentration was also observed during experiments utilizing the second method of electron removal—application of a voltage bias. The presence of the +1 v potential between the conducting layer of the construct and a Pt counter electrode during illumination forces electron flow away from the $TiO_2$ layer and results in oxygen production. However, when the voltage bias is removed and the illumination with UV light ceases, the $O_2$ concentration decreases and the current flow is observed to reverse for a short time. This reversal of current indicates that during illumination, a charge accumulation occurs within the photolytic construct. Once the light source and bias voltage are turned off, electrons flow back into the semiconductor layer and oxygen is adsorbed as in equation 1.

Photolytic constructs containing titanium as the conducting layer are included in table 1. These samples all used $TiO_2$ as the photoactive layer. As seen in the table, the thickness of the titanium metal affected the oxygen production rate. The resistance of the conducting layers increased after heat treatment because of oxidation. This loss of conductivity of the thin layers was significant and prevented them from acting as electron sinks. Little to no oxygen production was observed for these samples. Oxygen production occurred only when both the UV and bias voltage were applied to the sample. When either the light source or the voltage source were turned off, oxygen production ceased.

TABLE 1

Samples with titanium metal of various thickness as the conducting layer.

| Sample # | Thickness (Å) | Acid Treatment (s) | Heat Treatment (° C.) | Resistance (Ω) | DO Prod Rate (nmol/ml/s) |
| --- | --- | --- | --- | --- | --- |
| 90-32-1 | 100 | 15 | 250 | 50000 | 0 |
| 90-26-1 | 325 | 0 | 250 | 40000 | 11.8 |
| 75-83-2 | 1200 | 120 | 350 | 110 | 187 |
| 75-55-1 | 1230 | 60 | 350 | 110 | 114 |
| 75-64-1 | 1230 | 60 | 350 | 110 | 123 |

(Dissolved oxygen production experiments were performed in 2.35 ml Lockes Ringer solution at 36° C. with EFOS light source (88.9 mW/cm² at 365 nm) and +1v bias voltage.)

Other materials were tested for use as the conducting layer of the photolytic constructs. Table 2 lists these materials and the results from the oxygen production experiments. The materials included indium tin oxide (ITO), chromium, nickel, and copper. The samples containing copper as the conducting layer were not used in the DO experiments because the Cu metal completely oxidized even at room temperature once the photoactive layer was applied. Samples containing nickel did not produce oxygen. Current flow was observed, but photoadsorption of $O_2$ was the dominant process. Samples containing chromium were successful in evolving small amounts of oxygen. The effects of the synthesis parameters were observed in this series of constructs. The heating effects can be seen in samples #90-16-3 and #90-23-4. The former sample was heated at 350° C. for 45 min, while the latter was heated at 209° C. for 45 min. The higher temperature resulted in a greater loss of conductivity, which translated into zero oxygen production. Acid treatment also has an effect on oxygen production. Sample #75-94-3 was treated in 1N HCl for 30 s while sample #75-100-1 was treated for 60 s. After similar heat treatments at 350° C., the resulting constructs were seen to have similar resistance. However, the effect of the acid treatment can be seen in the decreased oxygen production rate of sample #75-100-1.

TABLE 2

Samples with Ni, Cr and ITO of various thickness as the conducting layer.

| Sample # | Material | Thickness (Å) | Acid Treatment (s) | Heat Treatment (° C.) | Resistance (Ω) | DO Prod Rate (nmol/ml/s) |
| --- | --- | --- | --- | --- | --- | --- |
| 90-14-1 | Ni | 450 | 0 | 350 | — | 0 |
| 90-23-2 | Ni | 450 | 0 | 250 | 105 | 0 |
| 90-16-3 | Cr | 100 | 0 | 350 | 870 | 0 |
| 90-23-4 | Cr | 100 | 0 | 209 | 690 | 2.13 |
| 75-94-3 | Cr | 400 | 30 | 350 | 230 | 57.7 |
| 75-100-1 | Cr | 400 | 60 | 350 | 200 | 4.12 |
| 90-03-1 | Cr | 1000 | 0 | 350 | — | 0 |
| 75-94-4 | ITO | 1300 | 30 | 350 | 55 | 54.7 |
| 90-03-4 | ITO | 1300 | 60 | 350 | 50 | 143 |
| 90-03-4 | ITO | 1300 | 60 | 350 | 50 | 34.4 |
| 90-52-1 | ITO | 1300 | 0 | 209 | 47 | 78.5 |

(DO production experiments were performed in 2.35 ml Lockes Ringer solution at 36° C. with EFOS light source (88.9 mW/cm² at 365 nm) and +1v bias voltage.)

ITO was used because it is a transparent, conductive material that will allow illumination of the photoactive layer by passing UV light through the substrate. This method is important as it prevents direct interaction of the solution medium with UV radiation. These samples all resulted in oxygen evolution. By comparing the oxygen concentration values obtained over three of the ITO containing samples, it is evident that the acid treatment is important in forming a continuous electronic pathway between the conductive and semiconductive (photoactive) layer. The sample treated in 1N HCl for 60 s exhibited the highest $O_2$ evolution with little charge accumulation. However, the sample treated in acid for 30 s resulted in a lower oxygen production rate and increased charge accumulation in the photoactive layer.

Photolytic reactions are ubiquitous mechanisms in nature, by which light is used to drive metabolism. One of the best-known photolytic reactions is photosynthesis, a series of reactions, by which green plants and certain bacteria utilize sunlight to catalyze the exchange of oxygen for carbon dioxide; while generating ATP. In the invention it was sought to apply these principles toward the development of a novel form of artificial lung, which will have the ability to carry out gas exchange in the blood, without exogenous delivery of gas, i.e. a "tank-less" respiratory support system. The invention provides for a system with the capability of generating dissolved oxygen directly in an aqueous medium, analogous to blood, through a series of light catalyzed chemical reactions. A prototype extracorporeal photolytic module has been configured, in which dissolved oxygen generation is coupled with $CO_2$ clearance, the latter carried out through selective diffusion of gas phase molecules, such as $CO_2$, $H_2$, and $N_2$ with retention of liquid phase molecules, such as dissolved oxygen. This micro-scale demonstration of artificial oxygen generation can be extended into a high-yield macro-scale device, effectively constituting an extracorporeal photolytic mechanism for physiological gas exchange.

In order to address this issue, the present invention emulates the natural process by which plants produce dissolved oxygen directly from water, photosynthesis, thus entirely omitting the gaseous state. The present invention provides a method, which significantly increases the amount of dissolved oxygen in liquids through light activation of a cascade of chemical reactions. A first goal is to provide a an extracorporeal device, then a highly miniaturized, intracorporal device, in order to achieve therapeutic gas exchange in patients. While the general approach is novel, it involves the combination of several well-characterized photochemical reactions. It is recognized that any artificial lung technology must accomplish physiological gas exchange, without altering pH balance or inducing blood cell lysis. During photosynthesis, oxygen is photolytically generated from water, using photolytic energy under mild conditions of pressure, temperature and pH, while releasing hydrogen ions. Hydrogen ions, which are released into solutions of bicarbonate ion, present in the serum, cause conversion of these ions into carbonic acid, which spontaneously dissociates into water and $CO_2$ in the presence of carbonic anhydrase, a natural component of blood.

For the present invention, a well-characterized semiconducting metal oxide was selected as the photo-absorption element, that is, the anatase form of titania, or $TiO_2$. Photolysis of this oxide results in the generation of active oxygen, in a manner, which is considerably more long lasting than photosynthetic pigments (i.e. the chlorophiles). Importantly, the light energy associated with activation by a 354 nm UV laser light selectively excites the $TiO_2$ semiconductor electronic transition (350-389 nm band, or about 3.2 eV) with minimal wasted radiation or transmission. Special dopants may adjust this wavelength, in order to reduce the energy requirement and even to allow activation within the range of visible light. UV energy produces charge separation in the anatase, which then produces active oxygen and free electrons, the latter being electrically conducted away. The general approach utilizes light energy to convert the active oxygen into dissolved oxygen for blood oxygenation. In general, diffusion layers were minimized by the use of electrical conduction of electrons to and from the photolytic site (as is done in natural photosynthesis) by photolytic transparency and by electrochemical conduction. The key findings from our study are that: 1) Thin films of $TiO_2$ (anatase) are capable of highly efficient UV absorption and energy transduction, and the generation of "active oxygen", or $H_2O_2$, and free electrons at the anatase surface; 2) Dissolved oxygen can be photolytically generated from active oxygen, using hydrogen peroxide ($H_2O_2$) as the active oxygen form. Thus, the feasibility of all of the key chemical aspects of a photolytic oxygen generation have been established in our test system.

A further disclosure in the present invention provides for gas permeable surfaces for allowing carbon dioxide and hydrogen, that are produced in the process of oxygenation, to be removed from the blood stream. Typically membranes in the form of flat surfaces (they may be rolled) or tubing are employed. Typically tubing having higher permeabilities for carbon dioxide and hydrogen and lower permeabilities for oxygen are used. Typically teflon based membranes and tubing are the most useful with the invention. A particularly preferred material is Teflon® AF tubing (or the same material in different forms such as flat plates or rolled). It is believed that the pore size of such surfaces is much smaller than that required for the passage of microorganisms such as single celled organisms, or viruses.

The preferred Teflon® AF tubing is available from Biogeneral 9925 Mesa Rim Road, San Diego, Calif. 92121.

It has the following useful properties

| GAS | Gas Permeability (cB) | PTFE |
|---|---|---|
| $CO_2$ | 280,000 | 1200 |
| $O_2$ | 99,000 | 420 |
| $H_2$ | 220,000 | 980 |
| $N_2$ | 49,000 | 140 | cB = centiBarrer

In summary, there is disclosed a device, which generates dissolved oxygen through photo-induction, and which provides commensurate $CO_2$ and $H_2$ clearance via selective membrane diffusion. In the typical embodiment of the present invention photolytic chemistry forms a natural mechanism for converting omnipresent light energy into useful chemical reactions. The results demonstrate, therefore, that photolytic induction is possible for use in an artificial lung. This technology promises great utility as a respiratory support device for patients severely impaired by chronic pulmonary disease, and will furthermore comprise the basis for a novel technological platform from which numerous other applications may emerge.

The invention has been described with reference to the preferred embodiments. Obviously, modifications and alterations will occur to others upon a reading and understanding the preceding detailed description. Particularly, it is clear to one having ordinary skill in the art that the photolytic cell can be modified and used in numerous other reactions and reaction systems. It is also apparent that the present photolytic cell can be used in organs other than the lungs, and that the cell can be used in living systems other than humans. Furthermore, one skilled in the art would appreciate based upon the preceding detailed description that the photolytic cell can be used in forming chemical reactions in solutions other than whole blood. It is intended that the invention be construed as including all such modifications and alterations in so far as they come within the scope of the appended claims or the equivalents thereof.

Having thus described the preferred embodiment, the invention is now claimed to be:

1. An artificial pulmonary capillary for oxygenating blood comprising:
   an inlet for receiving deoxygenated blood and transporting the blood to a photolytic cell; the photolytic cell having a transparent window, an anode, a cathode, a catholyte, and a photo-reactive surface, said photo-reactive surface having the ability to convert water in the blood to dissolved oxygen upon light activation, the anode adjacent to the transparent window, the cathode connected to the anode and adjacent to the catholyte;
   a light source for providing light photons to said photolytic cell and activating said photo-reactive surface; and
   an outlet for transporting oxygenated blood out of said photolytic cell.

2. The artificial pulmonary capillary of claim 1, wherein said photo-reactive surface comprises a light-activated catalyst.

3. The artificial pulmonary capillary of claim 2, wherein said light activated catalyst is a metal oxide catalyst comprising anatase ($TiO_2$), $WO_3$ or ZnO.

4. The artificial pulmonary capillary of claim 1, wherein said light source is an ultraviolet laser light at 350-390 nm.

5. The artificial pulmonary capillary of claim 2, wherein said light-activated catalyst converts, when photolytically irradiated, water in the blood to hydrogen ions, electrons and active oxygen.

6. The artificial pulmonary capillary of claim 5, wherein said active oxygen formed during photolysis is hydrogen peroxide or other forms of oxygen gas precursors.

7. The artificial pulmonary capillary of claim 5, wherein said electrons generated during photolysis are then electrically conducted away to avoid reversal of the reaction.

8. The artificial pulmonary capillary of claim 5, wherein said active oxygen formed during photolysis is converted by a disproportionation catalyst into dissolved oxygen.

9. The artificial pulmonary capillary of claim 8, wherein said disproportionation catalyst is $MnO_2$.

10. The artificial pulmonary capillary of claim 5, wherein said hydrogen ions formed during photolysis react with carbonate ions in the blood for form carbonic acid.

11. The artificial pulmonary capillary of claim 10, wherein said carbonic acid reacts with carbonic anhydrase in the blood to form water and carbon dioxide.

12. The artificial pulmonary capillary of claim 11, wherein said carbon dioxide is removed from the blood.

13. The artificial pulmonary capillary of claim 1, wherein the photo-reactive surface comprises a light transparent substrate and a photolytic coating.

14. The artificial pulmonary capillary of claim 13, wherein said photolytic coating comprises a layer of a light activated catalyst which converts, when photolytically irradiated, water in the blood to hydrogen ions, electrons and active oxygen.

15. The artificial pulmonary capillary of claim 14, wherein said photolytic coating further comprises a disproportionation catalyst which converts active oxygen to dissolved oxygen.

16. The artificial pulmonary capillary of claim 1, wherein said capillary has an internal diameter of 10µ or more.

17. The artificial pulmonary capillary of claim 1, wherein said capillary has an internal diameter of 10-200µ.

18. The artificial pulmonary capillary of claim 1, wherein the photolytic cell comprises a mesoporous material.

19. The artificial pulmonary capillary of claim 8, wherein said disproportionation catalyst includes at least one of $Fe^{II}$, $Fe^{III}$, $Cu^{I}$, $Cu^{II}$, $Co^{II}$, $Co^{III}$, $Mn^{II}$, $Mn^{III}$, $Mn^{IV}$, and $MnO_2$.

20. The photolytic cell of claim 18, wherein said cell is constructed of SAMMS.

* * * * *